(12) United States Patent
Harding et al.

(10) Patent No.: US 9,169,313 B2
(45) Date of Patent: *Oct. 27, 2015

(54) METHOD OF TREATMENT OF CANCERS CHARACTERIZED BY LIGAND-DEPENDENT ACTIVATING MUTATIONS IN FGFR2 WITH FGFR1 ECD PROTEINS

(71) Applicant: Five Prime Therapeutics, Inc., South San Francisco, CA (US)

(72) Inventors: Thomas Harding, San Francisco, CA (US); W. Michael Kavanaugh, Orinda, CA (US)

(73) Assignee: Five Prime Therapeutics, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/079,742

(22) Filed: Nov. 14, 2013

(65) Prior Publication Data

US 2014/0227263 A1 Aug. 14, 2014

Related U.S. Application Data

(63) Continuation of application No. 13/509,068, filed as application No. PCT/US2010/056627 on Nov. 12, 2010, now Pat. No. 8,614,183.

(60) Provisional application No. 61/261,291, filed on Nov. 13, 2009.

(51) Int. Cl.
| | |
|---|---|
| A61K 39/00 | (2006.01) |
| A61K 38/18 | (2006.01) |
| C07K 14/475 | (2006.01) |
| C07K 14/50 | (2006.01) |
| C07K 14/71 | (2006.01) |
| A61K 38/17 | (2006.01) |

(52) U.S. Cl.
CPC ............. *C07K 14/71* (2013.01); *A61K 38/179* (2013.01); *A61K 38/1825* (2013.01)

(58) Field of Classification Search
CPC ............. C07K 14/71; C07K 16/2863; C07K 2319/30; C07K 2317/732; C07K 16/22; C07K 2319/00; G01N 2333/71; A61K 38/179; A61K 38/1825; A61K 2300/00; A61K 2800/86; A61K 8/64

See application file for complete search history.

(56) References Cited

U.S. PATENT DOCUMENTS

| | | | |
|---|---|---|---|
| 5,229,501 A | 7/1993 | Keifer et al. | |
| 5,288,855 A | 2/1994 | Bergonzoni et al. | |
| 5,474,914 A | 12/1995 | Spaete | |
| 5,486,462 A | 1/1996 | Rutter et al. | |
| 5,707,632 A | 1/1998 | Williams et al. | |
| 5,750,371 A | 5/1998 | Senoo et al. | |
| 5,767,250 A | 6/1998 | Spaete | |
| 5,863,888 A | 1/1999 | Dionne et al. | |
| 6,255,454 B1 | 7/2001 | Keifer et al. | |
| 6,344,546 B1 | 2/2002 | Dionne et al. | |
| 6,350,593 B1 | 2/2002 | Williams et al. | |
| 6,355,440 B1 | 3/2002 | Williams et al. | |
| 6,384,191 B1 | 5/2002 | Williams et al. | |
| 6,517,872 B1 | 2/2003 | Yayon et al. | |
| 6,656,728 B1 | 12/2003 | Kavanaugh et al. | |
| 6,844,168 B1 | 1/2005 | Keifer et al. | |
| 7,135,311 B1 | 11/2006 | David et al. | |
| 7,297,493 B2 | 11/2007 | Lorenzi et al. | |
| 7,297,774 B2 | 11/2007 | Ullrich et al. | |
| 7,645,609 B2 | 1/2010 | Follstad | |
| 7,678,890 B2 | 3/2010 | Bosch et al. | |
| 7,982,014 B2 | 7/2011 | Williams et al. | |
| 8,119,770 B2 | 2/2012 | Blanche et al. | |
| 8,173,134 B2 | 5/2012 | Bosch et al. | |
| 8,338,569 B2 | 12/2012 | Marshall et al. | |
| 8,481,038 B2 | 7/2013 | Keer | |
| 2004/0063910 A1 | 4/2004 | Kavanaugh et al. | |
| 2004/0115768 A1 | 6/2004 | Follstad | |
| 2005/0187150 A1 | 8/2005 | Mohammadi et al. | |
| 2006/0234347 A1 | 10/2006 | Harding et al. | |
| 2006/0286102 A1 | 12/2006 | Jin et al. | |
| 2007/0248604 A1 | 10/2007 | Desnoyers et al. | |
| 2007/0248605 A1 | 10/2007 | Hestir et al. | |
| 2008/0171689 A1 | 7/2008 | Williams et al. | |

(Continued)

FOREIGN PATENT DOCUMENTS

| | | |
|---|---|---|
| EP | 0 545 343 A1 | 6/1993 |
| EP | 1910542 B2 | 2/2009 |

(Continued)

OTHER PUBLICATIONS

Adam et al., "Toward optimized front-line therapeutic strategies in patients with metastatic colorectal cancer-an expert review from the International Congress on Anti-cancer Treatment (ICACT) 2009," Annals of Oncology, 21: 1579-1584 (2010).

Akimoto et al., "Fibroblast growth factor 2 promotes microvessel formation from mouse embryonic aorta" Am. J. Physiol. Cell Physiol., vol. 284, No. 2, 2003, pp. C371-C377.

Anderson et al., "Apert syndrome mutations in fibroblast growth factor receptor 2 exhibit increased affinity for FGF ligand" Human Molecular Genetics, vol. 7, No. 9, 1998, pp. 1475-1483.

Andre et al., "Molecular Characterization of Breast Cancer with High-Resolution Oligonucleotide Comparative Genomic Hybridization Array," Clin Cancer Res, 2009, 15(2): 441-451.

(Continued)

*Primary Examiner* — Elly-Gerald Stoica

(74) *Attorney, Agent, or Firm* — McNeill Baur PLLC

(57) ABSTRACT

The present invention relates to the use of Fibroblast Growth Factor Receptor I (FGFR1) extracellular domain (ECD) polypeptides for treatment of cancers characterized by ligand dependent activating mutations in Fibroblast Growth Factor Receptor 2 (FGFR2). For example, the present invention relates to the treatment of endometrial cancers and other cancers wherein tumor cells express FGFR2 mutants in the IgII-IgIII hinge region or IgIII domain of the protein, such as at amino acid positions 252 and/or 253.

22 Claims, 10 Drawing Sheets

(56) References Cited

U.S. PATENT DOCUMENTS

| | | | |
|---|---|---|---|
| 2012/0128672 A1 | 5/2012 | Keer | |
| 2012/0183541 A1 | 7/2012 | Brennan et al. | |
| 2012/0237511 A1 | 9/2012 | Long et al. | |
| 2012/0251538 A1 | 10/2012 | Harding et al. | |
| 2012/0301921 A1 | 11/2012 | Williams et al. | |
| 2013/0004492 A1 | 1/2013 | Marshall et al. | |
| 2013/0136740 A1 | 5/2013 | Harding et al. | |

FOREIGN PATENT DOCUMENTS

| | | |
|---|---|---|
| EP | 2083081 A1 | 7/2009 |
| WO | WO 91/00916 | 1/1991 |
| WO | WO 91/11459 | 8/1991 |
| WO | WO 02/094852 | 11/2002 |
| WO | WO 2004/110487 A1 | 12/2004 |
| WO | WO 2005/113596 A2 | 12/2005 |
| WO | WO 2005/115363 A2 | 12/2005 |
| WO | WO 2006/081430 A2 | 8/2006 |
| WO | WO 2006/113277 A2 | 10/2006 |
| WO | WO 2007/014123 A2 | 2/2007 |
| WO | WO 2007/059574 A1 | 5/2007 |
| WO | WO 2007/134210 A2 | 11/2007 |
| WO | WO 2008/065543 A2 | 6/2008 |
| WO | WO 2008/118877 A2 | 10/2008 |
| WO | WO 2008/133873 | 11/2008 |
| WO | WO 2010/017198 | 2/2010 |
| WO | WO 2011/034940 | 3/2011 |
| WO | WO 2011/060333 A1 | 5/2011 |
| WO | WO 2011/084711 | 7/2011 |
| WO | WO 2012/125812 | 9/2012 |
| WO | WO 2012/177481 | 12/2012 |
| WO | WO 2013/074492 | 5/2013 |

OTHER PUBLICATIONS

Auguste et al., "Inhibition of fibroblast growth factor-fibroblast growth factor receptor activity in glioma cells impedes tumor growth by both angiogenesis-dependent and—independent mechanisms" Cancer Research, vol. 61, Feb. 15, 2001, pp. 1717-1726.

Baker et al., "Metabolic control of recombinant protein N-glycan processing in NSO and CHO cells" Biotechnology and Bioengineering, vol. 73, No. 3, May 5, 2001, pp. 188-202.

Ballinger et al., "Semirational design of a potent, artificial agonist of fibroblast growth factor receptors" Nature Biotechnology, vol. 17, Dec. 1999, pp. 1199-1204.

Bansal et al., "The Molecular Biology of Endometrial Cancers and the Implications for Pathogenesis, Classification, and Targeted Therapies," Cancer Control, 2009, 16(1):8-13.

Bass et al., "SOX2 Is an Amplified Lineage Survival Oncogene in Lung and Esophageal Squamous Cell Carcinomas," Nat. Genet., 2009, 41(11): 1238-1242, including supplemental information (15 pages).

Beroukhim et al., "The landscape of somatic copy-number alteration across human cancers," Nature, 2010, 463: 899-905.

Bjornsson et al., Pharmacokinetics of Heparin. II. Studies of Time Dependence in Rats, the Journal of Pharmacology and Experimental Therapeutics, vol. 210, No. 2, Apr. 1979, pp. 243-246.

Byron and Pollock, "FGFR2 as a molecular target in endometrial cancer," Future Oncol, 2009, 5(1):27-32.

Byron et al., "Inhibition of Activated Fibroblast Growth Factor Receptor 2 in Endometrial Cancer Cells Induces Cell Death Despite PTEN Abrogation," Cancer Res, 2008, 68(17):6902-6907.

Byron et al., "FGFR2 mutations are rare across histologic subtypes of ovarian cancer," Gynecologic Oncology, 2010, 117(1):125-129.

Celli et al., "Soluble dominant-negative receptor uncovers essential roles for fibroblast growth factors in multi-organ induction and patterning" The EMBO Journal, vol. 17, No. 6, Mar. 16, 1998, pp. 1642-1655.

Chellaiah et al., "Mapping ligand binding domains in chimeric fibroblast growth factor receptor molecules" J. Biol. Chem., vol. 274, No. 49, Dec. 3, 1999, pp. 34785-34794.

Cheon et al., "High-affinity binding sites for related fibroblast growth factor ligands reside within different receptor immunoglobulin-like domains" Proc. Natl. Acad. Sci., vol. 91, Feb. 1994, pp. 989-993.

Choo et al., SPdb—a Signal Peptide Database, BMC Bioinformatics, vol. 6, No. 249, Oct. 2005, pp. 1-8.

Compagni et al., "Fibroblast growth factors are required for efficient tumor angiogenesis" Cancer Research, vol. 60, Dec. 15, 2000, pp. 7163-7169.

Coughlin et al., "Acidic and basic fibroblast growth factors stimulate tyrosine kinase activity in vivo" J. Biol. Chem., vol. 263, No. 2, Jan. 15, 1988, pp. 988-993.

Courjal et al., "Comparative Genomic Hybridization Analysis of Breast Tumors with Predetermined Profiles of DNA Amplification," Cancer Res. 1997, 57(19):4368-77.

Cuny et al., "Relating genotype and phenotype in breast cancer: an analysis of the prognostic significance of amplification at eight different genes or loci and of p53 mutations," Cancer Res. 2000; 60(4):1077-83.

Dutt et al., "Drug-sensitive FGFR2 mutations in endometrial carcinoma," PNAS, 2008, 105(25):8713-8717.

Dutt et al., "Inhibitor-Sensitive FGFR1 Amplification in Human Non-Small Cell Lung Cancer," 2011, PLoS One, 6(6): e20351, 10 pages.

Elbauomy Elsheikh et al., "FGFR1 amplification in breast carcinomas: a chromogenic in situ hybridisation analysis," Breast Cancer Research 2007, 9:R23, 12 pages.

Ezzat et al., "A soluble dominant negative fibroblast growth factor receptor 4 isoform in human MCF-7 breast cancer cells" Biochem. Biophys. Res. Comm., vol. 287, No. 1, 2001, pp. 60-65.

Feige et al., "Glycosylation of the basic fibroblast growth factor receptor" J. Biol. Chem., vol. 263, No. 28, Oct. 5, 1988, pp. 14023-14029.

Gatius et al., "FGFR2 alterations in endometrial carcinoma," Modern Pathology, 2011, 24:1500-1510.

Gelsi-Boyer et al., "Comprehensive Profiling of 8p. 11-12 Amplification in Breast Cancer," Mol Cancer Res 2005;3(12): 655-667.

Genbank Accession No. X76885, 1994, 2 pages.

Genbank Accession No. Q90330, Nov. 1, 1996, 6 pages.

Gowardhan et al., "Evaluation of the fibroblast growth factor system as a potential target for therapy in human prostate cancer" British Journal of Cancer, vol. 92, Jan. 18, 2005, pp. 320-327.

Grossman et al., "Expression of human thyrotropin in cell lines with different glycosylation patterns combined with mutagenesis of specific glycosylation sites" J. Biol. Chem., vol. 270, No. 49, Dec. 8, 1995, pp. 29378-29385.

Guillonneau et al., "Fibroblast growth factor (FGF) soluble receptor 1 acts as a natural inhibitor of FGF2 neurotrophic activity during retinal degeneration" Molecular Biology of the Cell, vol. 9, Oct. 1998, pp. 2785-2802.

Hanneken et al., "Identification of soluble forms of the fibroblast growth factor receptor in blood" Proc. Natl. Acad. Sci., vol. 91, Sep. 1994, pp. 9170-9174.

Hanneken et al., "Soluble forms of the high-affinity fibroblast growth factor receptor in human vitreous fluid" Investigative Opthalmology & Visual Science, vol. 36, No. 6, May 1995, pp. 1192-1196.

Hanneken et al., "Structural characterization of the circulating soluble FGF receptors reveals multiple isoforms generated by secretion and ectodomain shedding" FEBS Letters, vol. 489, 2001, pp. 176-181.

Harding et al., "Role of VEGF, PDGF and FGF in glioblastoma progression as determined by soluble decoy receptor expression in preclinical models" Cell Genesys, Inc., Abstract No. 3030, presented at the AACR Annual Meeting, Apr. 16-20, 2005, 1 page.

Harding et al., "Preclinical Efficacy of FP-1039 (FGFR1:Fc) in Endometrical Carcinoma Models with Activating Mutations in FGFR2," AACR 101$^{st}$ Annual Meeting Poster (Apr. 17-21, 2010).

Harding et al., "Preclinical efficacy of fibroblast growth factor ligand trap HGS1036 in lung carcinoma models with genomic amplification of FGFR1" Poster from AACR Annual Meeting, Mar. 31-Apr. 4, 2012. 1 page.

Harding et al., "Blockade of Nonhormonal Fibroblast Growth Factors by FP-1039 Inhibits Growth of Multiple Types of Cancer," Science Translational Medicine, Mar. 2013, 5:178ra39 , pp. 1-9.

(56) References Cited

OTHER PUBLICATIONS

Harding et al., "Blockade of Nonhormonal Fibroblast Growth Factors by FP-1039 Inhibits Growth of Multiple Types of Cancer," Sci Transl Med, 2013, 5:178ra39, Supplemental Materials, 28 pages.
Ibrahimi et al., "Structural basis for fibroblast growth factor receptor 2 activation in Apert syndrome," PNAS, 2001, 98(13):7182-7187.
Ibrahimi et al., "Biochemical analysis of pathogenic ligand-dependent FGFR2 mutations suggests distinct pathophysiological mechanisms for craniofacial, and limb abnormalities," Human Molecular Genetics, 2004, 13(19):2313-2324.
Ibrahimi et al., "Proline to arginine mutations in FGF receptors 1 and 3 result in Pfeiffer and Muenke craniosynostosis syndromes through enhancement of FGF binding affinity," Hum. Mol. Genet., 13: 69-78 (2004).
Ibrahimi et al., "Analysis of Mutations in Fibroblast Growth Factor (FGF) and a Pathogenic Mutation in FGF Receptor (FGRF) Provides Direct Evidence for the Symmetric Two-End Model for FGFR Dimerization," Mol. Cell. Biol., 25(2): 671-684 (2005).
Jang et al., "FGFR1 is amplified during the progression of in situ to invasive breast carcinoma," Breast Cancer Research, 2012, 14:R115, pp. 1-12.
Johnson et al., "Diverse forms of a receptor for acidic and basic fibroblast growth factors" Molecular and Cellular Biology, vol. 10, No. 9, Sep. 1990, pp. 4728-4736.
Johnson et al, "The human fibroblast growth factor receptor genes: a common structural arrangement underlies the mechanisms for generating receptor forms that differ in their third immunoglobulin domain" Molecular and Cellular Biology, vol. 11, No. 9, Sep. 1991, pp. 4627-4634.
Kan et al., "Divalent cations and heparin-heparan sulfate cooperate to control assembly and activity of the fibroblast growth factor receptor complex" J. Biol. Chem., vol. 271, No. 42, Oct. 18, 1996, pp. 26143-26148.
Katoh, "Cancer genomics and genetics of FGFR2 (Review)," International Journal of Oncology, 2008, 33:233-237.
Katoh, "FGFR2 Abnormalities Underlie a Spectrum of Bone, Skin, and Cancer Pathologies," Journal of Investigative Dermatology, 2009, 129:1861-1867.
Kaufman et al., "Characterization of ligand binding to immobilized biotinylated extracellular domains of three growth factor receptors" Anal. Biochem., vol. 211, No. 2, Jun. 1993, pp. 261-266.
Keer et al., "Enrolling a Rare Patient Population: Establishing Proof of Concept for FP-1039, an FGF 'Trap,' in Endometrial Cancer Patients with the S252W FGFR2 Mutation," American Society of Clinical Oncology 2010, Annual Meeting, Jun. 4-8, 2010, Chicago, IL.
Keifer et al., "Molecular cloning of a human basic fibroblast growth factor receptor cDNA and expression of a biologically active extracellular domain in a baculovirus system" Growth Factors, vol. 5, 1991, pp. 115-127.
Kleeff et al., "Adenovirus-mediated transfer of a truncated fibroblast growth factor (FGF) type I receptor blocks FGF-2 signaling in multiple pancreatic cancer cell lines" Pancreas, vol. 28, No. 1, Jan. 2004, pp. 25-30.
Knights & Cook, "De-regulated FGF receptors as therapeutic targets in cancer," Pharmacol Ther, 2010, 125(1):105-117.
Kwabi-Addo et al., "The role of fibroblast growth factors and their receptors in prostate cancer" Endocrine-Related Cancer, vol. 11, No. 4, Dec. 2004, pp. 709-724.
Lazar et al., "Transforming Growth Factor alpha: Mutation of Aspartic Acid 47 and Leucine 48 Results Different Biological Activities," Mol Cell Biol, 1988, 8(3):1247-1252.
Lee et al., "Purification and complementary DNA cloning of a receptor for basic fibroblast growth factor" Science, vol. 245, No. 4913, Jul. 7, 1989, pp. 57-60.
Lee et al., "Molecular profiles of EGFR, K-ras, c-met, and FGFR in pulmonary pleomorphic carcinoma, a rare lung malignancy," J. Cancer Res. Clin. Oncol., May 28, 2011, 9 pages.
Levi et al., "Matrix metalloproteinase 2 releases active soluble ectodomain of fibroblast growth factor receptor 1", XP-002413740, Proc. Natl. Acad. Sci., USA, vol. 93, pp. 7069-7074, (Jul. 1996).
Li et al., "Cell transformation by fibroblast growth factors can be suppressed by truncated fibroblast growth factor receptors" Molecular and Cellular Biology, vol. 14, No. 11, Nov. 1994, pp. 7660-7669.
Liu et al, "Utilization of Unlabeled Probes for the Detection of Fibroblast Growth Factor Receptor 2 Exons 7 and 12 Mutations in Endometrial Carcinoma," Appl Immunohistochem Mol Morphol, 2011, 19(4):341-346.
Liuzzo et al., "Human leukemia cell lines bind basic fibroblast growth factor (FGF) on FGF receptors and heparin sulfates: downmodulation of FGF receptors by phorbol ester" Blood, vol. 87, No. 1, Jan. 1, 1996, pp. 245-255.
Long et al. "Abstract #2789: Antitumor efficacy of FP-1039, a soluble FGF receptor 1:Fc conjugate, as a single agent or in combination with anticancer drugs," Proceedings of the American Association for Cancer Research, Apr. 18-22, 2009 Denver, CO.
Long et al. "Preclinical antitumor efficacy of FP-1039, a soluble FGF receptor 1:Fc conjugate, as a single agent or in combination with anticancer drugs," Proceedings of the American association for Cancer Research, Apr. 17-22, 2009 Denver, CO.
Loo et al., "Production and characterization of the extracellular domain of recombinant human fibroblast growth factor receptor 4," Intl. J. Biochem. Cell Biol., 32: 489-497 (2000).
Lopez et al., "A novel type I fibroblast growth factor receptor activates mitogenic signaling in the absence of detectable tyrosine phosphorylation of FRS2" J. Biol. Chem., vol. 275, No. 21, May 26, 2000, pp. 15933-15939.
Lundin et al., "Selectively desulfated heparin inhibits fibroblast growth factor-induced mitogenicity and angiogenesis" J. Biol. Chem., vol. 275, No. 32, Aug. 11, 2000, pp. 24653-24660.
Ma et al., "Combination of antiangiogenesis with chemotherapy for more effective cancer treatment," Mol Cancer Ther, 7: 3670-3684 (2008).
Mansukhani et al., "A murine fibroblast growth factor (FGF) receptor expressed in CHO cells is activated by basic FGF and Kaposi FGF" Proc. Natl. Acad. Sci., vol. 87, Jun. 1990, pp. 4378-4382.
Marics et al., "FGFR4 signaling is a necessary step in limb muscle differentiation," Development, 2002, 129:4559-4569.
Marshall et al., "Fibroblast Growth Factor Receptors Are Components of Autocrine Signaling Networks in Head and Neck Squamous Cell Carcinoma Cells," 2011, 17(15): 5016-5025.
Mayer et al., "Ratiometric dosing of anticancer drug combinations: Controlling drug ratios after systemic administration regulates therapeutic activity in tumor-bearing mice," Mol Cancer Ther, 5(7): 1854-1863 (2006).
Meijer et al., Fibroblast Growth Factor Receptor 4 Predicts Failure on Tamoxifen Therapy in Patients with Recurrent Breast Cancer, Endocrine-Related Cancer, vol. 15, 2008, pp. 101-111.
Moloney et al., "Exclusive paternal origin of new mutations in Apert syndrome," Nature Genetics, 1996, 13:48-53.
Ogawa et al., "Anti-tumor angiogenesis therapy using soluble receptors: enhanced inhibition of tumor growth when soluble fibroblast growth factor receptor-1 is used with soluble vascular endothelial growth factor receptor" Cancer Gene Therapy, vol. 9, Aug. 2002, pp. 633-640.
Olsen et al., "Insights into the molecular basis for fibroblast growth factor receptor autoinhibition and ligand-binding promiscuity" Proc. Natl. Acad. Sci., vol. 101, No. 4 Jan. 27, 2004, pp. 935-940.
Ornitz et al., "Heparin is required for cell-free binding of basic fibroblast growth factor to a soluble receptor and for mitogenesis in whole cells" Molecular and Cellular Biology, vol. 12, Jan. 1992, pp. 240-247.
Ornitz et al., "Receptor specificity of the fibroblast growth factor family" J. Biol. Chem., vol. 271, No. 25, Jun. 21, 1996, pp. 15292-15297.
Otto et al., "Sialylated complex-type N-glycans enhance the signaling activity of soluble intercellular adhesion molecule-1 in mouse astrocytes" J. Biol. Chem., vol. 279, No. 34, Aug. 20, 2004, pp. 35201-35209.

(56) References Cited

OTHER PUBLICATIONS

Pasquale et al., "Identification of a developmentally regulated protein-tyrosine kinase by using anti-phosphotyrosine antibodies to screen a cDNA expression library" Proc. Natl. Acad. Sci., vol. 86, Jul. 1989, pp. 5449-5453.
Pellegrini et al., "Crystal structure of fibroblast growth factor receptor ectodomain bound to ligand and heparin," Nature, 407: 1029-1034 (2000).
Plotnikov et al., "Structural basis for FGF receptor dimerization and activation" Cell, vol. 98, Sep. 3, 1999, pp. 641-650.
Plotnikov et al., "Crystal structures of two FGF-FGFR complexes reveal the determinants of ligand-receptor specificity" Cell, vol. 101, May 12, 2000, pp. 413-424.
Pollock et al., "Frequent activating FGFR2 mutations in endometrial carcinomas parallel germline mutations associated with craniosynostosis and skeletal dysplasia syndromes," Oncogene, 2007, 26:7158-7162.
Powell et al., "Fibroblast growth factor receptors 1 and 2 interact differently with heparin-heparan sulfate" J. Biol. Chem., vol. 277, No. 32, Aug. 9, 2002, pp. 28554-28563.
Powers et al., "Fibroblast growth factors, their receptors and signaling", XP-002165147, Endocrine-Related Cancer, 7, pp. 165-197, (2000).
Rang et al, "Cancer chemotherapy," *Rang and Dale's Pharmacology*, Churchill Linvingston Elsevier, 2008, pp. 718-735.
Reis-Filho et al., "FGFR1Emerges as a PotentialTherapeuticTarget for Lobular Breast Carcinomas," 2006, Clin. Cancer Res. 12(22): 6652-6662.
Reynolds et al., "Evaluating Response to Antineoplastic Drug Combinations in Tissue Culture Models," from Methods in Molecular Medicine, vol. 110: Chemosensitivity: vol. 1: In Vitro Assays, Edited by R.D. Blumenthal, Humana Press Inc., Totowa, NJ, pp. 173-183, 2005.
Robertson et al., "Activating mutations in the extracellular domain of the fibroblast growth factor receptor 2 function by disruption of the disulfide bond in the third immunoglobulin-like domain," Proc. Natl. Acad. Sci., USA, 95: 4567-4572 (1998).
Roghani et al., "Heparin increases the affinity of basic fibroblast growth factor for its receptor but is not required for binding" J. Biol. Chem., vol. 269, No. 6, Feb. 11, 1994, pp. 3976-3984.
Ruta et al., "A novel protein tyrosine kinase gene whose expression is modulated during endothelial cell differentiation" Oncogene, 1988, vol. 3, pp. 9-15.
Sahadevan et al., Selective Over-expression of Fibroblast Growth Factor Receptors I and 4 in Clinical Prostate Cancer, Journal of Pathology, vol. 213, Jul. 2007, pp. 82-90.
Sanchez-Heras et al., "The fibroblast growth factor receptor acid box is essential for interactions with N-cadherin and all of the major isoforms of neural cell adhesion molecules," J Biol Chem, 2006, 281(46):35208-16.
Schlessinger et al., "Crystal Structure of the Ternary FGF-FGFR-Herparin Complex Reveals a Dual Role for Heparin in FGFR Binding and Dimerization," Molecular Cell, 6: 743-750 (2000).
Seshacharyulu et al., "Targeting the EGFR signaling pathway in cancer therapy," Expert Opin Ther Targets, 16(1): 15-31 (2012).
Shamim et al., "Sequential roles for Fgf4, En1 and Fgf8 in specification and regionalization of the midbrain" Development, vol. 126, Feb. 1999, pp. 945-959.
Smith et al., "The asparagine-linked oligosaccharides on tissue factor pathway inhibitor terminate with ( $SO_4$-4GalNAcβ1,4GIcNAcβ1,2Manα" J. Biol. Chem., vol. 267, No. 27, Sep. 25, 1992, pp. 19140-19146.
St. Bernard et al., "Fibroblast growth factor receptors as molecular targets in thyroid carcinoma" Endocrinology, vol. 146, No. 3, 2005, pp. 1145-1153.
St. Bernard et al., "Fibroblast growth factor receptors as molecular targets in thyroid carcinoma" Endocrinology, vol. 10, Nov. 24, 2004, pp. 1-26 and 6 pgs. figures.
Stauber et al., "Structural interaction of fibroblast growth factor receptor with its ligands," Proc. Natl. Acad. Sci., USA, 97(1): 49-54 (2000).
Sugiura et al., "Co-expression of aFGF and FGFR-1 is predictive of a poor prognosis in patients with esophageal squamous cell carcinoma," Oncology Reports, 2007, 17: 557-564.
Tacer et al., "Research Resource: Comprehensive Expression Atlas of the Fibroblast Growth Factor System in Adult Mouse," Mol Endocrinol., 2010, 24(10):2050-2064, incl Supplemental Files, 23 pages total.
Taraboletti et al., "Potential Antagonism of Tubulin-Binding Anticancer Agents in Combination Therapies," Clin Cancer Res 11(7): 2720-2726 (2005).
Tolcher et al., "Preliminary Results of a Phase 1 Study of FP-1039 (FGFR1:Fc), A Novel Antagonist of Multiple Fibroblast Growth Factor (FGF) Ligands, In Patients With Advanced Malignancies," 2009 AACR-EORTC-NCI Molecular Targets and Cancer Therapeutics Conference Poster (Nov. 15-18, 2009).
Tolcher et al., "Preliminary Results of a Dose Escalation Study of the Fibroblast Growth Factor (FGF) "trap" FP-1039 (FGFR1:Fc) In Patients With Advanced Malignancies," 22nd EORTC-NCI-AACR Symposium on Molecular Targets and Cancer Therapeutics Poster (Nov. 16-19, 2010).
Tolcher et al., "Preliminary results of a dose escalation study of the Fibroblast Growth Factor (FGF) "trap" FP-1039 (FGFR1:Fc) in patients with advanced malignancies," *European Journal of Cancer, Supplement*, 8(7): 121, Abstract No. 381 (Nov. 18, 2010).
Tomlinson et al., "Alternative splicing of fibroblast growth factor receptor 3 produces a secreted isoform that inhibits fibroblast growth factor-induced proliferation and is repressed in urothelial carcinoma cell lines" Cancer Research, vol. 65, No. 22, Nov. 15, 2005, pp. 10441-10449.
Trueb et al., "Characterization of FGFRL1, a novel fibroblast growth factor (FGF) receptor preferentially expressed in skeletal tissues" J. Biol. Chem., vol. 278, No. 36, Sep. 5, 2003, pp. 33857-33865.
Tucker et al., "A novel approach for inhibiting growth factor signalling in murine tooth development" Eur. J. Oral Sci., vol. 106 (suppl. 1), 1998, pp. 122-125.
Tuominen et al., "Expression and glycosylation studies of human FGF Receptor 4" Protein Expression and Purification, vol. 21, Mar. 2001, pp. 275-285.
Turner et al., "FGFR1 Amplification Drives Endocrine Therapy Resistance and Is a Therapeutic Target in Breast Cancer," 2010, 70(5): 2085-2094.
Turner et al., "A Therapeutic Target for Smoking-Associated Lung Cancer," 2010, Science Trans. Med. 2(62): 62ps56, 4 pages.
Ueno et al., "A truncated form of fibroblast growth factor receptor 1 inhibits signal transduction by multiple types of fibroblast growth factor receptor" J. Biol. Chem., vol. 267, No. 3, Jan. 25, 1992, pp. 1470-1476.
Van Den Nieuwenhof et al., "Recombinant glycodelin carrying the same type of glycan structures as contraceptive glycodelin-A can be produced in human kidney 293 cells but not in Chinese hamster ovary cells" Eur. J. Biochem., vol. 267, Aug. 2000, pp. 4753-4762.
Voortman et al., "Array comparative genomic hybridization-based characterization of genetic alterations in pulmonary neuroendocrine tumors," 2010, PNAS, 107(29): 13040-13045.
Wagner et al., "Suppression of fibroblast growth factor receptor signaling inhibits pancreatic cancer growth in vitro and in vivo" Gastroenterology, vol. 114, Apr. 1998, pp. 798-807.
Wang et al., "Purification and characterization of a functional soluble fibroblast growth factor receptor 1" Biochem. Biophys. Res. Comm., vol. 203, No. 3, Sep. 30, 1994, pp. 1781-1788.
Wang et al., "A natural kinase-deficient variant of fibroblast growth factor receptor 1" Biochemistry, Vo. 35, 1996, pp. 10134-10142.
Wang et al., "Alternately Spliced NH2-terminallmmunoglobulin-like Loop I in the Ectodomain of the Fibroblast Growth Factor (FGF) Receptor 1 Lowers Affinity for both Heparin and FGF-1," J. Biol. Chem, 270(17): 10231-10235 (1995).
Weiss et al., "Frequent and Focal FGFR1 Amplification Associates with Therapeutically Tractable FGFR1 Dependency in Squamous Cell Lung Cancer," Science Trans. Med., 2010, 2(62): 62ra93, 8 pages.

(56) References Cited

OTHER PUBLICATIONS

Wells, "Additivity of Mutational Effects in Proteins," Biochemistry, 1990, 29(37):8509-8517.
Werner et al., "Differential splicing in the extracellular region of fibroblast growth factor receptor 1 generates receptor variants with different ligand-binding specificities" Molecular and Cellular Biology, vol. 12, No. 1, Jan. 1992, pp. 82-88.
Williams et al., "Activation of the FGF receptor underlies neurite outgrowth stimulated by L1, N-CAM, and N-Cadherin" Neuron, vol. 13, Sep. 1994, pp. 583-594.
Ye et al., "FGF and Shh signals control dopaminergic and serotonergic cell fate in the anterior neural plate" Cell, vol. 93, May 29, 1998, pp. 755-766.
Yoo et al., "Docetaxel Associated Pathways in Cisplatin Resistant Head and Neck Squamous Cell Carcinoma: A Pilot Study," Laryngoscope, 115: 1938-1946 (2005.
Yu et al., "Loss of fibroblast growth factor receptor 2 ligand-binding specificity in Apert syndrome," PNAS, 2000, 97(26):14536-14541.
Zhang et al., Receptor Specificity of the Fibroblast Growth Factor Family: The Complete Mammalian FGF Family, The Journal of Biological Chemistry, vol. 281, No. 23, Jun. 9, 2006, pp. 15694-15700.
Zhang et al., "FP-1039 (FGFR1:Fc), A Soluble FGFR1 Receptor Antagonist, Inhibits Tumor Growth and Angiogenesis," AACR-NCI-EORTC International Conference, Oct. 22-26, 2007, San Francisco, CA.
Zheng et al. "Enhanced efficacy in anti-tumour activity by combined therapy of recombinant FGFR-1 related angiogenesis and low-dose cytotoxic agent," European Journal of Cancer, vol. 43, No. 14, Sep. 14, 2007, pp. 2134-2139.
Zytovision GmbH, Catalogue 2011, 1st Edition, 84 pages.
File History for U.S. Appl. No. 11/791,889, filed May 30, 2007.
File History for U.S. Appl. No. 12/535,479, filed Aug. 4, 2009.
File History for U.S. Appl. No. 12/652,720, filed Jan. 5, 2010.
File History for U.S. Appl. No. 13/157,712, filed Jun. 10, 2011.
File history for U.S. Appl. No. 13/227,398, filed Sep. 7, 2011.
File History for U.S. Appl. No. 13/296,161, filed Nov. 14, 2011.
File History for U.S. Appl. No. 13/296,168, filed Nov. 14, 2011.
File History for U.S. Appl. No. 13/496,182, filed Mar. 14, 2012.
File History for U.S. Appl. No. 13/438,638, filed Apr. 3, 2012.
File History for U.S. Appl. No. 13/509,068, filed Jun. 13, 2012.
File History for U.S. Appl. No. 13/612,044, filed Sep. 12, 2012.
File History for U.S. Appl. No. 13/675,255, filed Nov. 13, 2012.
File History for U.S. Appl. No. 13/515,429, filed Nov. 21, 2012.
File History for U.S. Appl. No. 13/905,042, filed May 29, 2013.
International Search Report and Written Opinion of the International Searching Authority, mailed Sep. 18, 2007, for International Application No. PCT/US2006/028597, 23 pages.
International Preliminary Report on Patentability, mailed Jan. 22, 2008, for International Application No. PCT/US2006/028597, 14 pages.
International Search Report and written Opinion, mailed Mar. 8, 2010, for PCT/US2009/052704, filed Aug. 4, 2009, 14 pages.
International Search Report and Written Opinion, mailed Feb. 4, 2011, for International Patent Application PCT/US2010/056627, 15 pages.
International Search Report and Written Opinion of the International Searching Authority, mailed Jan. 31, 2012, for International Application No. PCT/US2011/060661, 16 pages.
International Search Report and Written Opinion of the International Searching Authority, mailed Apr. 12, 2012, for International Application No. PCT/US2011/060666, 20 pages.
International Search Report and Written Opinion mailed Apr. 1, 2013 for PCT/US2012/064772, 16 pages.
European Search Report, mailed Jun. 5, 2009, in European Application No. 09075061.3, 2 pages.
European Search Report, mailed May 2, 2013, in European Patent Application No. 10817774.2, 8 pages.
Invitation to Pay Additional Fees and, Where Applicable, Protest Fee, mailed Dec. 31, 2012, in international Application No. PCT/US2012/64772, 2 pages.

SEQUENCE LISTING

<160> NUMBER OF SEQ ID NOS: 25

<210> SEQ ID NO 1
<211> LENGTH: 353
<212> TYPE: PRT
<213> ORGANISM: artificial sequence
<220> FEATURE:
<223> OTHER INFORMATION: FGFR1 IIIc ECD

<400> SEQUENCE: 1

```
Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
            20                  25                  30

Arg Cys Arg Leu Arg Asp Asp Val Gln Ser Ile Asn Trp Leu Arg Asp
        35                  40                  45

Gly Val Gln Leu Ala Glu Ser Asn Arg Thr Arg Ile Thr Gly Glu Glu
    50                  55                  60

Val Glu Val Gln Asp Ser Val Pro Ala Asp Ser Gly Leu Tyr Ala Cys
65                  70                  75                  80

Val Thr Ser Ser Pro Ser Gly Ser Asp Thr Thr Tyr Phe Ser Val Asn
                85                  90                  95

Val Ser Asp Ala Leu Pro Ser Ser Glu Asp Asp Asp Asp Asp Asp Asp
            100                 105                 110

Ser Ser Ser Glu Glu Lys Glu Thr Asp Asn Thr Lys Pro Asn Pro Val
        115                 120                 125

Ala Pro Tyr Trp Thr Ser Pro Glu Lys Met Glu Lys Lys Leu His Ala
    130                 135                 140

Val Pro Ala Ala Lys Thr Val Lys Phe Lys Cys Pro Ser Ser Gly Thr
145                 150                 155                 160

Pro Asn Pro Thr Leu Arg Trp Leu Lys Asn Gly Lys Glu Phe Lys Pro
                165                 170                 175

Asp His Arg Ile Gly Gly Tyr Lys Val Arg Tyr Ala Thr Trp Ser Ile
            180                 185                 190

Ile Met Asp Ser Val Val Pro Ser Asp Lys Gly Asn Tyr Thr Cys Ile
        195                 200                 205

Val Glu Asn Glu Tyr Gly Ser Ile Asn His Thr Tyr Gln Leu Asp Val
    210                 215                 220

Val Glu Arg Ser Pro His Arg Pro Ile Leu Gln Ala Gly Leu Pro Ala
225                 230                 235                 240

Asn Lys Thr Val Ala Leu Gly Ser Asn Val Glu Phe Met Cys Lys Val
                245                 250                 255
```

```
Tyr Ser Asp Pro Gln Pro His Ile Gln Trp Leu Lys His Ile Glu Val
            260                 265                 270

Asn Gly Ser Lys Ile Gly Pro Asp Asn Leu Pro Tyr Val Gln Ile Leu
            275                 280                 285

Lys Thr Ala Gly Val Asn Thr Thr Asp Lys Glu Met Glu Val Leu His
            290                 295                 300

Leu Arg Asn Val Ser Phe Glu Asp Ala Gly Glu Tyr Thr Cys Leu Ala
305                 310                 315                 320

Gly Asn Ser Ile Gly Leu Ser His His Ser Ala Trp Leu Thr Val Leu
                325                 330                 335

Glu Ala Leu Glu Glu Arg Pro Ala Val Met Thr Ser Pro Leu Tyr Leu
            340                 345                 350

Glu

<210> SEQ ID NO 2
<211> LENGTH: 374
<212> TYPE: PRT
<213> ORGANISM: artificial sequence
<220> FEATURE:
<223> OTHER INFORMATION: FGFR1 IIIc ECD w/ signal peptide

<400> SEQUENCE: 2

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
            35                  40                  45

Asp Leu Leu Gln Leu Arg Cys Arg Leu Arg Asp Asp Val Gln Ser Ile
        50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
            115                 120                 125

Asp Asp Asp Asp Asp Ser Ser Ser Glu Glu Lys Glu Thr Asp Asn Thr
        130                 135                 140

Lys Pro Asn Pro Val Ala Pro Tyr Trp Thr Ser Pro Glu Lys Met Glu
145                 150                 155                 160

Lys Lys Leu His Ala Val Pro Ala Ala Lys Thr Val Lys Phe Lys Cys
                165                 170                 175

Pro Ser Ser Gly Thr Pro Asn Pro Thr Leu Arg Trp Leu Lys Asn Gly
            180                 185                 190

Lys Glu Phe Lys Pro Asp His Arg Ile Gly Gly Tyr Lys Val Arg Tyr
            195                 200                 205

Ala Thr Trp Ser Ile Ile Met Asp Ser Val Val Pro Ser Asp Lys Gly
            210                 215                 220

Asn Tyr Thr Cys Ile Val Glu Asn Glu Tyr Gly Ser Ile Asn His Thr
225                 230                 235                 240

Tyr Gln Leu Asp Val Val Glu Arg Ser Pro His Arg Pro Ile Leu Gln
                245                 250                 255
```

Ala Gly Leu Pro Ala Asn Lys Thr Val Ala Leu Gly Ser Asn Val Glu
            260                 265                 270

Phe Met Cys Lys Val Tyr Ser Asp Pro Gln Pro His Ile Gln Trp Leu
    275                 280                 285

Lys His Ile Glu Val Asn Gly Ser Lys Ile Gly Pro Asp Asn Leu Pro
290                 295                 300

Tyr Val Gln Ile Leu Lys Thr Ala Gly Val Asn Thr Thr Asp Lys Glu
305                 310                 315                 320

Met Glu Val Leu His Leu Arg Asn Val Ser Phe Glu Asp Ala Gly Glu
                325                 330                 335

Tyr Thr Cys Leu Ala Gly Asn Ser Ile Gly Leu Ser His His Ser Ala
                340                 345                 350

Trp Leu Thr Val Leu Glu Ala Leu Glu Glu Arg Pro Ala Val Met Thr
                355                 360                 365

Ser Pro Leu Tyr Leu Glu
            370

<210> SEQ ID NO 3
<211> LENGTH: 349
<212> TYPE: PRT
<213> ORGANISM: artificial sequence
<220> FEATURE:
<223> OTHER INFORMATION: FGFR1 IIIc ECD delta4, (R1Mut1 ECD)

<400> SEQUENCE: 3

Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
                20                  25                  30

Arg Cys Arg Leu Arg Asp Asp Val Gln Ser Ile Asn Trp Leu Arg Asp
            35                  40                  45

Gly Val Gln Leu Ala Glu Ser Asn Arg Thr Arg Ile Thr Gly Glu Glu
        50                  55                  60

Val Glu Val Gln Asp Ser Val Pro Ala Asp Ser Gly Leu Tyr Ala Cys
65                  70                  75                  80

Val Thr Ser Ser Pro Ser Gly Ser Asp Thr Thr Tyr Phe Ser Val Asn
                85                  90                  95

Val Ser Asp Ala Leu Pro Ser Ser Glu Asp Asp Asp Asp Asp Asp Asp
            100                 105                 110

Ser Ser Ser Glu Glu Lys Glu Thr Asp Asn Thr Lys Pro Asn Pro Val
        115                 120                 125

Ala Pro Tyr Trp Thr Ser Pro Glu Lys Met Glu Lys Lys Leu His Ala
130                 135                 140

Val Pro Ala Ala Lys Thr Val Lys Phe Lys Cys Pro Ser Ser Gly Thr
145                 150                 155                 160

Pro Asn Pro Thr Leu Arg Trp Leu Lys Asn Gly Lys Glu Phe Lys Pro
                165                 170                 175

Asp His Arg Ile Gly Gly Tyr Lys Val Arg Tyr Ala Thr Trp Ser Ile
            180                 185                 190

Ile Met Asp Ser Val Val Pro Ser Asp Lys Gly Asn Tyr Thr Cys Ile
        195                 200                 205

Val Glu Asn Glu Tyr Gly Ser Ile Asn His Thr Tyr Gln Leu Asp Val
        210                 215                 220

Val Glu Arg Ser Pro His Arg Pro Ile Leu Gln Ala Gly Leu Pro Ala
225                 230                 235                 240

```
Asn Lys Thr Val Ala Leu Gly Ser Asn Val Glu Phe Met Cys Lys Val
            245                 250                 255

Tyr Ser Asp Pro Gln Pro His Ile Gln Trp Leu Lys His Ile Glu Val
        260                 265                 270

Asn Gly Ser Lys Ile Gly Pro Asp Asn Leu Pro Tyr Val Gln Ile Leu
            275                 280                 285

Lys Thr Ala Gly Val Asn Thr Thr Asp Lys Glu Met Glu Val Leu His
        290                 295                 300

Leu Arg Asn Val Ser Phe Glu Asp Ala Gly Glu Tyr Thr Cys Leu Ala
305                 310                 315                 320

Gly Asn Ser Ile Gly Leu Ser His His Ser Ala Trp Leu Thr Val Leu
            325                 330                 335

Glu Ala Leu Glu Glu Arg Pro Ala Val Met Thr Ser Pro
        340                 345

<210> SEQ ID NO 4
<211> LENGTH: 345
<212> TYPE: PRT
<213> ORGANISM: artificial sequence
<220> FEATURE:
<223> OTHER INFORMATION: FGFR1 IIIc ECD delta8; (R1Mut2 ECD)

<400> SEQUENCE: 4

Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
            20                  25                  30

Arg Cys Arg Leu Arg Asp Asp Val Gln Ser Ile Asn Trp Leu Arg Asp
        35                  40                  45

Gly Val Gln Leu Ala Glu Ser Asn Arg Thr Arg Ile Thr Gly Glu Glu
    50                  55                  60

Val Glu Val Gln Asp Ser Val Pro Ala Asp Ser Gly Leu Tyr Ala Cys
65                  70                  75                  80

Val Thr Ser Ser Pro Ser Gly Ser Asp Thr Thr Tyr Phe Ser Val Asn
            85                  90                  95

Val Ser Asp Ala Leu Pro Ser Ser Glu Asp Asp Asp Asp Asp Asp Asp
        100                 105                 110

Ser Ser Ser Glu Glu Lys Glu Thr Asp Asn Thr Lys Pro Asn Pro Val
    115                 120                 125

Ala Pro Tyr Trp Thr Ser Pro Glu Lys Met Glu Lys Lys Leu His Ala
130                 135                 140

Val Pro Ala Ala Lys Thr Val Lys Phe Lys Cys Pro Ser Ser Gly Thr
145                 150                 155                 160

Pro Asn Pro Thr Leu Arg Trp Leu Lys Asn Gly Lys Glu Phe Lys Pro
            165                 170                 175

Asp His Arg Ile Gly Gly Tyr Lys Val Arg Tyr Ala Thr Trp Ser Ile
        180                 185                 190

Ile Met Asp Ser Val Val Pro Ser Asp Lys Gly Asn Tyr Thr Cys Ile
    195                 200                 205

Val Glu Asn Glu Tyr Gly Ser Ile Asn His Thr Tyr Gln Leu Asp Val
210                 215                 220

Val Glu Arg Ser Pro His Arg Pro Ile Leu Gln Ala Gly Leu Pro Ala
225                 230                 235                 240

Asn Lys Thr Val Ala Leu Gly Ser Asn Val Glu Phe Met Cys Lys Val
            245                 250                 255
```

```
Tyr Ser Asp Pro Gln Pro His Ile Gln Trp Leu Lys His Ile Glu Val
            260                 265                 270

Asn Gly Ser Lys Ile Gly Pro Asp Asn Leu Pro Tyr Val Gln Ile Leu
            275                 280                 285

Lys Thr Ala Gly Val Asn Thr Thr Asp Lys Glu Met Glu Val Leu His
            290                 295                 300

Leu Arg Asn Val Ser Phe Glu Asp Ala Gly Glu Tyr Thr Cys Leu Ala
305                 310                 315                 320

Gly Asn Ser Ile Gly Leu Ser His His Ser Ala Trp Leu Thr Val Leu
            325                 330                 335

Glu Ala Leu Glu Glu Arg Pro Ala Val
            340                 345

<210> SEQ ID NO 5
<211> LENGTH: 344
<212> TYPE: PRT
<213> ORGANISM: artificial sequence
<220> FEATURE:
<223> OTHER INFORMATION: FGFR1 IIIc ECD delta9; (R1Mut3 ECD)

<400> SEQUENCE: 5

Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
            20                  25                  30

Arg Cys Arg Leu Arg Asp Asp Val Gln Ser Ile Asn Trp Leu Arg Asp
            35                  40                  45

Gly Val Gln Leu Ala Glu Ser Asn Arg Thr Arg Ile Thr Gly Glu Glu
        50                  55                  60

Val Glu Val Gln Asp Ser Val Pro Ala Asp Ser Gly Leu Tyr Ala Cys
65                  70                  75                  80

Val Thr Ser Ser Pro Ser Gly Ser Asp Thr Thr Tyr Phe Ser Val Asn
            85                  90                  95

Val Ser Asp Ala Leu Pro Ser Ser Glu Asp Asp Asp Asp Asp Asp Asp
            100                 105                 110

Ser Ser Ser Glu Glu Lys Glu Thr Asp Asn Thr Lys Pro Asn Pro Val
            115                 120                 125

Ala Pro Tyr Trp Thr Ser Pro Glu Lys Met Glu Lys Lys Leu His Ala
            130                 135                 140

Val Pro Ala Ala Lys Thr Val Lys Phe Lys Cys Pro Ser Ser Gly Thr
145                 150                 155                 160

Pro Asn Pro Thr Leu Arg Trp Leu Lys Asn Gly Lys Glu Phe Lys Pro
            165                 170                 175

Asp His Arg Ile Gly Gly Tyr Lys Val Arg Tyr Ala Thr Trp Ser Ile
            180                 185                 190

Ile Met Asp Ser Val Val Pro Ser Asp Lys Gly Asn Tyr Thr Cys Ile
            195                 200                 205

Val Glu Asn Glu Tyr Gly Ser Ile Asn His Thr Tyr Gln Leu Asp Val
            210                 215                 220

Val Glu Arg Ser Pro His Arg Pro Ile Leu Gln Ala Gly Leu Pro Ala
225                 230                 235                 240

Asn Lys Thr Val Ala Leu Gly Ser Asn Val Glu Phe Met Cys Lys Val
            245                 250                 255

Tyr Ser Asp Pro Gln Pro His Ile Gln Trp Leu Lys His Ile Glu Val
            260                 265                 270
```

```
Asn Gly Ser Lys Ile Gly Pro Asp Asn Leu Pro Tyr Val Gln Ile Leu
            275                 280                 285

Lys Thr Ala Gly Val Asn Thr Thr Asp Lys Glu Met Glu Val Leu His
    290                 295                 300

Leu Arg Asn Val Ser Phe Glu Asp Ala Gly Glu Tyr Thr Cys Leu Ala
305                 310                 315                 320

Gly Asn Ser Ile Gly Leu Ser His His Ser Ala Trp Leu Thr Val Leu
                325                 330                 335

Glu Ala Leu Glu Glu Arg Pro Ala
            340

<210> SEQ ID NO 6
<211> LENGTH: 339
<212> TYPE: PRT
<213> ORGANISM: artificial sequence
<220> FEATURE:
<223> OTHER INFORMATION: FGFR1 IIIc ECD delta14; (R1Mut4 ECD)

<400> SEQUENCE: 6

Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
            20                  25                  30

Arg Cys Arg Leu Arg Asp Asp Val Gln Ser Ile Asn Trp Leu Arg Asp
    35                  40                  45

Gly Val Gln Leu Ala Glu Ser Asn Arg Thr Arg Ile Thr Gly Glu Glu
    50                  55                  60

Val Glu Val Gln Asp Ser Val Pro Ala Asp Ser Gly Leu Tyr Ala Cys
65                  70                  75                  80

Val Thr Ser Ser Pro Ser Gly Ser Asp Thr Thr Tyr Phe Ser Val Asn
                85                  90                  95

Val Ser Asp Ala Leu Pro Ser Ser Glu Asp Asp Asp Asp Asp Asp Asp
            100                 105                 110

Ser Ser Ser Glu Glu Lys Glu Thr Asp Asn Thr Lys Pro Asn Pro Val
    115                 120                 125

Ala Pro Tyr Trp Thr Ser Pro Glu Lys Met Glu Lys Lys Leu His Ala
    130                 135                 140

Val Pro Ala Ala Lys Thr Val Lys Phe Lys Cys Pro Ser Ser Gly Thr
145                 150                 155                 160

Pro Asn Pro Thr Leu Arg Trp Leu Lys Asn Gly Lys Glu Phe Lys Pro
                165                 170                 175

Asp His Arg Ile Gly Gly Tyr Lys Val Arg Tyr Ala Thr Trp Ser Ile
            180                 185                 190

Ile Met Asp Ser Val Val Pro Ser Asp Lys Gly Asn Tyr Thr Cys Ile
    195                 200                 205

Val Glu Asn Glu Tyr Gly Ser Ile Asn His Thr Tyr Gln Leu Asp Val
    210                 215                 220

Val Glu Arg Ser Pro His Arg Pro Ile Leu Gln Ala Gly Leu Pro Ala
225                 230                 235                 240

Asn Lys Thr Val Ala Leu Gly Ser Asn Val Glu Phe Met Cys Lys Val
                245                 250                 255

Tyr Ser Asp Pro Gln Pro His Ile Gln Trp Leu Lys His Ile Glu Val
            260                 265                 270

Asn Gly Ser Lys Ile Gly Pro Asp Asn Leu Pro Tyr Val Gln Ile Leu
    275                 280                 285
```

```
Lys Thr Ala Gly Val Asn Thr Thr Asp Lys Glu Met Glu Val Leu His
        290                 295                 300

Leu Arg Asn Val Ser Phe Glu Asp Ala Gly Glu Tyr Thr Cys Leu Ala
305                 310                 315                 320

Gly Asn Ser Ile Gly Leu Ser His His Ser Ala Trp Leu Thr Val Leu
                325                 330                 335

Glu Ala Leu

<210> SEQ ID NO 7
<211> LENGTH: 334
<212> TYPE: PRT
<213> ORGANISM: artificial sequence
<220> FEATURE:
<223> OTHER INFORMATION: FGFR1 IIIc ECD delta19; (R1Mut5 ECD)

<400> SEQUENCE: 7

Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
            20                  25                  30

Arg Cys Arg Leu Arg Asp Asp Val Gln Ser Ile Asn Trp Leu Arg Asp
        35                  40                  45

Gly Val Gln Leu Ala Glu Ser Asn Arg Thr Arg Ile Thr Gly Glu Glu
    50                  55                  60

Val Glu Val Gln Asp Ser Val Pro Ala Asp Ser Gly Leu Tyr Ala Cys
65                  70                  75                  80

Val Thr Ser Ser Pro Ser Gly Ser Asp Thr Thr Tyr Phe Ser Val Asn
                85                  90                  95

Val Ser Asp Ala Leu Pro Ser Ser Glu Asp Asp Asp Asp Asp Asp Asp
            100                 105                 110

Ser Ser Ser Glu Glu Lys Glu Thr Asp Asn Thr Lys Pro Asn Pro Val
        115                 120                 125

Ala Pro Tyr Trp Thr Ser Pro Glu Lys Met Glu Lys Lys Leu His Ala
    130                 135                 140

Val Pro Ala Ala Lys Thr Val Lys Phe Lys Cys Pro Ser Ser Gly Thr
145                 150                 155                 160

Pro Asn Pro Thr Leu Arg Trp Leu Lys Asn Gly Lys Glu Phe Lys Pro
                165                 170                 175

Asp His Arg Ile Gly Gly Tyr Lys Val Arg Tyr Ala Thr Trp Ser Ile
            180                 185                 190

Ile Met Asp Ser Val Val Pro Ser Asp Lys Gly Asn Tyr Thr Cys Ile
        195                 200                 205

Val Glu Asn Glu Tyr Gly Ser Ile Asn His Thr Tyr Gln Leu Asp Val
    210                 215                 220

Val Glu Arg Ser Pro His Arg Pro Ile Leu Gln Ala Gly Leu Pro Ala
225                 230                 235                 240

Asn Lys Thr Val Ala Leu Gly Ser Asn Val Glu Phe Met Cys Lys Val
                245                 250                 255

Tyr Ser Asp Pro Gln Pro His Ile Gln Trp Leu Lys His Ile Glu Val
            260                 265                 270

Asn Gly Ser Lys Ile Gly Pro Asp Asn Leu Pro Tyr Val Gln Ile Leu
        275                 280                 285

Lys Thr Ala Gly Val Asn Thr Thr Asp Lys Glu Met Glu Val Leu His
    290                 295                 300

Leu Arg Asn Val Ser Phe Glu Asp Ala Gly Glu Tyr Thr Cys Leu Ala
```

Gly Asn Ser Ile Gly Leu Ser His His Ser Ala Trp Leu Thr
            325                 330

<210> SEQ ID NO 8
<211> LENGTH: 351
<212> TYPE: PRT
<213> ORGANISM: artificial sequence
<220> FEATURE:
<223> OTHER INFORMATION: FGFR1 IIIc ECD deltaP364 and A365; (R1Mut7 ECD)

<400> SEQUENCE: 8

Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
            20                  25                  30

Arg Cys Arg Leu Arg Asp Asp Val Gln Ser Ile Asn Trp Leu Arg Asp
        35                  40                  45

Gly Val Gln Leu Ala Glu Ser Asn Arg Thr Arg Ile Thr Gly Glu Glu
    50                  55                  60

Val Glu Val Gln Asp Ser Val Pro Ala Asp Ser Gly Leu Tyr Ala Cys
65                  70                  75                  80

Val Thr Ser Ser Pro Ser Gly Ser Asp Thr Thr Tyr Phe Ser Val Asn
                85                  90                  95

Val Ser Asp Ala Leu Pro Ser Ser Glu Asp Asp Asp Asp Asp Asp Asp
            100                 105                 110

Ser Ser Ser Glu Glu Lys Glu Thr Asp Asn Thr Lys Pro Asn Pro Val
        115                 120                 125

Ala Pro Tyr Trp Thr Ser Pro Glu Lys Met Glu Lys Lys Leu His Ala
    130                 135                 140

Val Pro Ala Ala Lys Thr Val Lys Phe Lys Cys Pro Ser Ser Gly Thr
145                 150                 155                 160

Pro Asn Pro Thr Leu Arg Trp Leu Lys Asn Gly Lys Glu Phe Lys Pro
                165                 170                 175

Asp His Arg Ile Gly Gly Tyr Lys Val Arg Tyr Ala Thr Trp Ser Ile
            180                 185                 190

Ile Met Asp Ser Val Val Pro Ser Asp Lys Gly Asn Tyr Thr Cys Ile
        195                 200                 205

Val Glu Asn Glu Tyr Gly Ser Ile Asn His Thr Tyr Gln Leu Asp Val
    210                 215                 220

Val Glu Arg Ser Pro His Arg Pro Ile Leu Gln Ala Gly Leu Pro Ala
225                 230                 235                 240

Asn Lys Thr Val Ala Leu Gly Ser Asn Val Glu Phe Met Cys Lys Val
                245                 250                 255

Tyr Ser Asp Pro Gln Pro His Ile Gln Trp Leu Lys His Ile Glu Val
            260                 265                 270

Asn Gly Ser Lys Ile Gly Pro Asp Asn Leu Pro Tyr Val Gln Ile Leu
        275                 280                 285

Lys Thr Ala Gly Val Asn Thr Thr Asp Lys Glu Met Glu Val Leu His
    290                 295                 300

Leu Arg Asn Val Ser Phe Glu Asp Ala Gly Glu Tyr Thr Cys Leu Ala
305                 310                 315                 320

Gly Asn Ser Ile Gly Leu Ser His His Ser Ala Trp Leu Thr Val Leu
                325                 330                 335

Glu Ala Leu Glu Glu Arg Val Met Thr Ser Pro Leu Tyr Leu Glu

<210> SEQ ID NO 9
<211> LENGTH: 353
<212> TYPE: PRT
<213> ORGANISM: artificial sequence
<220> FEATURE:
<223> OTHER INFORMATION: FGFR1 IIIc ECD P364G; (R1Mut8 ECD)

<400> SEQUENCE: 9

```
Arg Pro Ser Pro Thr Leu Pro Glu Gln Ala Gln Pro Trp Gly Ala Pro
1               5                   10                  15
Val Glu Val Glu Ser Phe Leu Val His Pro Gly Asp Leu Leu Gln Leu
                20                  25                  30
Arg Cys Arg Leu Arg Asp Asp Val Gln Ser Ile Asn Trp Leu Arg Asp
            35                  40                  45
Gly Val Gln Leu Ala Glu Ser Asn Arg Thr Arg Ile Thr Gly Glu Glu
    50                  55                  60
Val Glu Val Gln Asp Ser Val Pro Ala Asp Ser Gly Leu Tyr Ala Cys
65                  70                  75                  80
Val Thr Ser Ser Pro Ser Gly Ser Asp Thr Thr Tyr Phe Ser Val Asn
                85                  90                  95
Val Ser Asp Ala Leu Pro Ser Ser Glu Asp Asp Asp Asp Asp Asp Asp
            100                 105                 110
Ser Ser Ser Glu Glu Lys Glu Thr Asp Asn Thr Lys Pro Asn Pro Val
    115                 120                 125
Ala Pro Tyr Trp Thr Ser Pro Glu Lys Met Glu Lys Lys Leu His Ala
130                 135                 140
Val Pro Ala Ala Lys Thr Val Lys Phe Lys Cys Pro Ser Ser Gly Thr
145                 150                 155                 160
Pro Asn Pro Thr Leu Arg Trp Leu Lys Asn Gly Lys Glu Phe Lys Pro
                165                 170                 175
Asp His Arg Ile Gly Gly Tyr Lys Val Arg Tyr Ala Thr Trp Ser Ile
            180                 185                 190
Ile Met Asp Ser Val Val Pro Ser Asp Lys Gly Asn Tyr Thr Cys Ile
    195                 200                 205
Val Glu Asn Glu Tyr Gly Ser Ile Asn His Thr Tyr Gln Leu Asp Val
210                 215                 220
Val Glu Arg Ser Pro His Arg Pro Ile Leu Gln Ala Gly Leu Pro Ala
225                 230                 235                 240
Asn Lys Thr Val Ala Leu Gly Ser Asn Val Glu Phe Met Cys Lys Val
                245                 250                 255
Tyr Ser Asp Pro Gln Pro His Ile Gln Trp Leu Lys His Ile Glu Val
            260                 265                 270
Asn Gly Ser Lys Ile Gly Pro Asp Asn Leu Pro Tyr Val Gln Ile Leu
    275                 280                 285
Lys Thr Ala Gly Val Asn Thr Thr Asp Lys Glu Met Glu Val Leu His
290                 295                 300
Leu Arg Asn Val Ser Phe Glu Asp Ala Gly Glu Tyr Thr Cys Leu Ala
305                 310                 315                 320
Gly Asn Ser Ile Gly Leu Ser His His Ser Ala Trp Leu Thr Val Leu
                325                 330                 335
Glu Ala Leu Glu Glu Arg Gly Ala Val Met Thr Ser Pro Leu Tyr Leu
            340                 345                 350
Glu
```

<210> SEQ ID NO 10
<211> LENGTH: 353
<212> TYPE: PRT
<213> ORGANISM: artificial sequence
<220> FEATURE:
<223> OTHER INFORMATION: FGFR1 IIIc ECD P364M; (R1Mut9 ECD)

<400> SEQUENCE: 10

```
Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
            20                  25                  30

Arg Cys Arg Leu Arg Asp Asp Val Gln Ser Ile Asn Trp Leu Arg Asp
        35                  40                  45

Gly Val Gln Leu Ala Glu Ser Asn Arg Thr Arg Ile Thr Gly Glu Glu
    50                  55                  60

Val Glu Val Gln Asp Ser Val Pro Ala Asp Ser Gly Leu Tyr Ala Cys
65                  70                  75                  80

Val Thr Ser Ser Pro Ser Gly Ser Asp Thr Thr Tyr Phe Ser Val Asn
                85                  90                  95

Val Ser Asp Ala Leu Pro Ser Ser Glu Asp Asp Asp Asp Asp Asp Asp
            100                 105                 110

Ser Ser Ser Glu Glu Lys Glu Thr Asp Asn Thr Lys Pro Asn Pro Val
        115                 120                 125

Ala Pro Tyr Trp Thr Ser Pro Glu Lys Met Glu Lys Lys Leu His Ala
    130                 135                 140

Val Pro Ala Ala Lys Thr Val Lys Phe Lys Cys Pro Ser Ser Gly Thr
145                 150                 155                 160

Pro Asn Pro Thr Leu Arg Trp Leu Lys Asn Gly Lys Glu Phe Lys Pro
                165                 170                 175

Asp His Arg Ile Gly Gly Tyr Lys Val Arg Tyr Ala Thr Trp Ser Ile
            180                 185                 190

Ile Met Asp Ser Val Val Pro Ser Asp Lys Gly Asn Tyr Thr Cys Ile
        195                 200                 205

Val Glu Asn Glu Tyr Gly Ser Ile Asn His Thr Tyr Gln Leu Asp Val
    210                 215                 220

Val Glu Arg Ser Pro His Arg Pro Ile Leu Gln Ala Gly Leu Pro Ala
225                 230                 235                 240

Asn Lys Thr Val Ala Leu Gly Ser Asn Val Glu Phe Met Cys Lys Val
                245                 250                 255

Tyr Ser Asp Pro Gln Pro His Ile Gln Trp Leu Lys His Ile Glu Val
            260                 265                 270

Asn Gly Ser Lys Ile Gly Pro Asp Asn Leu Pro Tyr Val Gln Ile Leu
        275                 280                 285

Lys Thr Ala Gly Val Asn Thr Thr Asp Lys Glu Met Glu Val Leu His
    290                 295                 300

Leu Arg Asn Val Ser Phe Glu Asp Ala Gly Glu Tyr Thr Cys Leu Ala
305                 310                 315                 320

Gly Asn Ser Ile Gly Leu Ser His His Ser Ala Trp Leu Thr Val Leu
                325                 330                 335

Glu Ala Leu Glu Glu Arg Met Ala Val Met Thr Ser Pro Leu Tyr Leu
            340                 345                 350

Glu
```

<210> SEQ ID NO 11
<211> LENGTH: 353
<212> TYPE: PRT
<213> ORGANISM: artificial sequence
<220> FEATURE:
<223> OTHER INFORMATION: FGFR1 IIIc ECD M367N; (R1Mut10 ECD)

<400> SEQUENCE: 11

```
Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
            20                  25                  30

Arg Cys Arg Leu Arg Asp Asp Val Gln Ser Ile Asn Trp Leu Arg Asp
        35                  40                  45

Gly Val Gln Leu Ala Glu Ser Asn Arg Thr Arg Ile Thr Gly Glu Glu
    50                  55                  60

Val Glu Val Gln Asp Ser Val Pro Ala Asp Ser Gly Leu Tyr Ala Cys
65                  70                  75                  80

Val Thr Ser Ser Pro Ser Gly Ser Asp Thr Thr Tyr Phe Ser Val Asn
                85                  90                  95

Val Ser Asp Ala Leu Pro Ser Ser Glu Asp Asp Asp Asp Asp Asp Asp
            100                 105                 110

Ser Ser Ser Glu Glu Lys Glu Thr Asp Asn Thr Lys Pro Asn Pro Val
        115                 120                 125

Ala Pro Tyr Trp Thr Ser Pro Glu Lys Met Glu Lys Lys Leu His Ala
    130                 135                 140

Val Pro Ala Ala Lys Thr Val Lys Phe Lys Cys Pro Ser Ser Gly Thr
145                 150                 155                 160

Pro Asn Pro Thr Leu Arg Trp Leu Lys Asn Gly Lys Glu Phe Lys Pro
                165                 170                 175

Asp His Arg Ile Gly Gly Tyr Lys Val Arg Tyr Ala Thr Trp Ser Ile
            180                 185                 190

Ile Met Asp Ser Val Val Pro Ser Asp Lys Gly Asn Tyr Thr Cys Ile
        195                 200                 205

Val Glu Asn Glu Tyr Gly Ser Ile Asn His Thr Tyr Gln Leu Asp Val
    210                 215                 220

Val Glu Arg Ser Pro His Arg Pro Ile Leu Gln Ala Gly Leu Pro Ala
225                 230                 235                 240

Asn Lys Thr Val Ala Leu Gly Ser Asn Val Glu Phe Met Cys Lys Val
                245                 250                 255

Tyr Ser Asp Pro Gln Pro His Ile Gln Trp Leu Lys His Ile Glu Val
            260                 265                 270

Asn Gly Ser Lys Ile Gly Pro Asp Asn Leu Pro Tyr Val Gln Ile Leu
        275                 280                 285

Lys Thr Ala Gly Val Asn Thr Thr Asp Lys Glu Met Glu Val Leu His
    290                 295                 300

Leu Arg Asn Val Ser Phe Glu Asp Ala Gly Glu Tyr Thr Cys Leu Ala
305                 310                 315                 320

Gly Asn Ser Ile Gly Leu Ser His His Ser Ala Trp Leu Thr Val Leu
                325                 330                 335

Glu Ala Leu Glu Glu Arg Pro Ala Val Asn Thr Ser Pro Leu Tyr Leu
            340                 345                 350

Glu
```

```
<210> SEQ ID NO 12
<211> LENGTH: 355
<212> TYPE: PRT
<213> ORGANISM: artificial sequence
<220> FEATURE:
<223> OTHER INFORMATION: FGFR1 RM ECD

<400> SEQUENCE: 12

Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
            20                  25                  30

Arg Cys Arg Leu Arg Asp Asp Val Gln Ser Ile Asn Trp Leu Arg Asp
        35                  40                  45

Gly Val Gln Leu Ala Glu Ser Asn Arg Thr Arg Ile Thr Gly Glu Glu
    50                  55                  60

Val Glu Val Gln Asp Ser Val Pro Ala Asp Ser Gly Leu Tyr Ala Cys
65                  70                  75                  80

Val Thr Ser Ser Pro Ser Gly Ser Asp Thr Thr Tyr Phe Ser Val Asn
                85                  90                  95

Val Ser Asp Ala Leu Pro Ser Ser Glu Asp Asp Asp Asp Asp Asp Asp
            100                 105                 110

Ser Ser Ser Glu Glu Lys Glu Thr Asp Asn Thr Lys Pro Asn Arg Met
        115                 120                 125

Pro Val Ala Pro Tyr Trp Thr Ser Pro Glu Lys Met Glu Lys Lys Leu
    130                 135                 140

His Ala Val Pro Ala Ala Lys Thr Val Lys Phe Lys Cys Pro Ser Ser
145                 150                 155                 160

Gly Thr Pro Asn Pro Thr Leu Arg Trp Leu Lys Asn Gly Lys Glu Phe
                165                 170                 175

Lys Pro Asp His Arg Ile Gly Gly Tyr Lys Val Arg Tyr Ala Thr Trp
            180                 185                 190

Ser Ile Ile Met Asp Ser Val Val Pro Ser Asp Lys Gly Asn Tyr Thr
        195                 200                 205

Cys Ile Val Glu Asn Glu Tyr Gly Ser Ile Asn His Thr Tyr Gln Leu
    210                 215                 220

Asp Val Val Glu Arg Ser Pro His Arg Pro Ile Leu Gln Ala Gly Leu
225                 230                 235                 240

Pro Ala Asn Lys Thr Val Ala Leu Gly Ser Asn Val Glu Phe Met Cys
                245                 250                 255

Lys Val Tyr Ser Asp Pro Gln Pro His Ile Gln Trp Leu Lys His Ile
            260                 265                 270

Glu Val Asn Gly Ser Lys Ile Gly Pro Asp Asn Leu Pro Tyr Val Gln
        275                 280                 285

Ile Leu Lys Thr Ala Gly Val Asn Thr Thr Asp Lys Glu Met Glu Val
    290                 295                 300

Leu His Leu Arg Asn Val Ser Phe Glu Asp Ala Gly Tyr Thr Cys
305                 310                 315                 320

Leu Ala Gly Asn Ser Ile Gly Leu Ser His His Ser Ala Trp Leu Thr
                325                 330                 335

Val Leu Glu Ala Leu Glu Glu Arg Pro Ala Val Met Thr Ser Pro Leu
            340                 345                 350

Tyr Leu Glu
        355
```

```
<210> SEQ ID NO 13
<211> LENGTH: 21
<212> TYPE: PRT
<213> ORGANISM: artificial sequence
<220> FEATURE:
<223> OTHER INFORMATION: FGFR1 signal peptide

<400> SEQUENCE: 13

Met Trp Ser Trp Lys Cys Leu Leu Phe Trp Ala Val Leu Val Thr Ala
1               5                   10                  15

Thr Leu Cys Thr Ala
            20

<210> SEQ ID NO 14
<211> LENGTH: 21
<212> TYPE: PRT
<213> ORGANISM: artificial sequence
<220> FEATURE:
<223> OTHER INFORMATION: FGFR2 signal peptide

<400> SEQUENCE: 14

Met Val Ser Trp Gly Arg Phe Ile Cys Leu Val Val Val Thr Met Ala
1               5                   10                  15

Thr Leu Ser Leu Ala
            20

<210> SEQ ID NO 15
<211> LENGTH: 22
<212> TYPE: PRT
<213> ORGANISM: artificial sequence
<220> FEATURE:
<223> OTHER INFORMATION: FGFR3 signal peptide

<400> SEQUENCE: 15

Met Gly Ala Pro Ala Cys Ala Leu Ala Leu Cys Val Ala Val Ala Ile
1               5                   10                  15

Val Ala Gly Ala Ser Ser
            20

<210> SEQ ID NO 16
<211> LENGTH: 21
<212> TYPE: PRT
<213> ORGANISM: artificial sequence
<220> FEATURE:
<223> OTHER INFORMATION: FGFR4 signal peptide

<400> SEQUENCE: 16

Met Arg Leu Leu Leu Ala Leu Leu Gly Ile Leu Leu Ser Val Pro Gly
1               5                   10                  15

Pro Pro Val Leu Ser
            20

<210> SEQ ID NO 17
<211> LENGTH: 232
<212> TYPE: PRT
<213> ORGANISM: artificial sequence
<220> FEATURE:
<223> OTHER INFORMATION: Fc C237S

<400> SEQUENCE: 17

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30
```

```
Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
            165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys
225                 230

<210> SEQ ID NO 18
<211> LENGTH: 228
<212> TYPE: PRT
<213> ORGANISM: artificial sequence
<220> FEATURE:
<223> OTHER INFORMATION: Fc

<400> SEQUENCE: 18

Glu Arg Lys Cys Cys Val Glu Cys Pro Pro Cys Pro Ala Pro Pro Val
 1               5                  10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
            35                  40                  45

His Glu Asp Pro Glu Val Gln Phe Asn Trp Tyr Val Asp Gly Val Glu
 50                  55                  60

Val His Asn Ala Lys Thr Lys Pro Arg Glu Glu Gln Phe Asn Ser Thr
 65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
            115                 120                 125

Val Tyr Thr Leu Pro Pro Ser Arg Glu Glu Met Thr Lys Asn Gln Val
130                 135                 140

Ser Leu Thr Cys Leu Val Lys Gly Phe Tyr Pro Ser Asp Ile Ala Val
145                 150                 155                 160
```

```
Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
        180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
210                 215                 220

Ser Pro Gly Lys
225

<210> SEQ ID NO 19
<211> LENGTH: 229
<212> TYPE: PRT
<213> ORGANISM: artificial sequence
<220> FEATURE:
<223> OTHER INFORMATION: Fc

<400> SEQUENCE: 19

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 20
<211> LENGTH: 229
<212> TYPE: PRT
<213> ORGANISM: artificial sequence
<220> FEATURE:
<223> OTHER INFORMATION: Fc

<400> SEQUENCE: 20
```

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys
225

<210> SEQ ID NO 21
<211> LENGTH: 228
<212> TYPE: PRT
<213> ORGANISM: artificial sequence
<220> FEATURE:
<223> OTHER INFORMATION: Fc

<400> SEQUENCE: 21

Glu Arg Lys Ser Ser Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125
```

```
Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 22
<211> LENGTH: 562
<212> TYPE: PRT
<213> ORGANISM: artificial sequence
<220> FEATURE:
<223> OTHER INFORMATION: FGFR1 IIIc ECD delta14 + Fc; (R1Mut4)

<400> SEQUENCE: 22

Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
            20                  25                  30

Arg Cys Arg Leu Arg Asp Asp Val Gln Ser Ile Asn Trp Leu Arg Asp
        35                  40                  45

Gly Val Gln Leu Ala Glu Ser Arg Thr Arg Ile Thr Gly Glu Glu Val
    50                  55                  60

Glu Val Gln Asp Ser Val Pro Ala Asp Ser Gly Leu Tyr Ala Cys Val
65                  70                  75                  80

Thr Ser Ser Pro Ser Gly Ser Asp Thr Thr Tyr Phe Ser Val Val Ser
                85                  90                  95

Asp Ala Leu Pro Ser Ser Glu Asp Asp Asp Asp Asp Asp Asp Ser Ser
            100                 105                 110

Ser Glu Glu Lys Glu Thr Asp Asn Thr Lys Pro Asn Pro Val Ala Pro
        115                 120                 125

Tyr Trp Thr Ser Pro Glu Lys Met Glu Lys Lys Leu His Ala Val Pro
    130                 135                 140

Ala Ala Lys Thr Val Lys Phe Lys Cys Pro Ser Ser Gly Thr Pro Asn
145                 150                 155                 160

Pro Thr Leu Arg Trp Leu Lys Asn Gly Lys Glu Phe Lys Pro Asp His
                165                 170                 175

Arg Ile Gly Gly Tyr Lys Val Arg Tyr Ala Thr Trp Ser Ile Ile Met
            180                 185                 190

Asp Ser Val Val Pro Ser Asp Lys Gly Tyr Thr Cys Ile Val Glu Asn
        195                 200                 205

Glu Tyr Gly Ser Ile His Thr Tyr Gln Leu Asp Val Val Glu Arg Ser
    210                 215                 220

Pro His Arg Pro Ile Leu Gln Ala Gly Leu Pro Ala Lys Thr Val Ala
225                 230                 235                 240

Leu Gly Ser Asn Val Glu Phe Met Cys Lys Val Tyr Ser Asp Pro Gln
                245                 250                 255
```

```
Pro His Ile Gln Trp Leu Lys His Ile Glu Val Gly Ser Lys Ile Gly
            260                 265                 270

Pro Asp Asn Leu Pro Tyr Val Gln Ile Leu Lys Thr Ala Gly Val Thr
            275                 280                 285

Thr Asp Lys Glu Met Glu Val Leu His Leu Arg Val Ser Phe Glu Asp
            290                 295                 300

Ala Gly Glu Tyr Thr Cys Leu Ala Gly Asn Ser Ile Gly Leu Ser His
305                 310                 315                 320

His Ser Ala Trp Leu Thr Val Leu Glu Ala Leu Glu Pro Lys Ser Ser
                325                 330                 335

Asp Lys Thr His Thr Cys Pro Pro Cys Pro Ala Pro Glu Leu Leu Gly
                340                 345                 350

Gly Pro Ser Val Phe Leu Phe Pro Pro Lys Pro Lys Asp Thr Leu Met
            355                 360                 365

Ile Ser Arg Thr Pro Glu Val Thr Cys Val Val Val Asp Val Ser His
            370                 375                 380

Glu Asp Pro Glu Val Lys Phe Asn Trp Tyr Val Asp Gly Val Glu Val
385                 390                 395                 400

His Asn Ala Lys Thr Lys Pro Arg Glu Glu Gln Tyr Ser Thr Tyr Arg
                405                 410                 415

Val Val Ser Val Leu Thr Val Leu His Gln Asp Trp Leu Asn Gly Lys
                420                 425                 430

Glu Tyr Lys Cys Lys Val Ser Asn Lys Ala Leu Pro Ala Pro Ile Glu
            435                 440                 445

Lys Thr Ile Ser Lys Ala Lys Gly Gln Pro Arg Glu Pro Gln Val Tyr
            450                 455                 460

Thr Leu Pro Pro Ser Arg Asp Glu Leu Thr Lys Asn Gln Val Ser Leu
465                 470                 475                 480

Thr Cys Leu Val Lys Gly Phe Tyr Pro Ser Asp Ile Ala Val Glu Trp
                485                 490                 495

Glu Ser Asn Gly Gln Pro Glu Asn Asn Tyr Lys Thr Thr Pro Pro Val
            500                 505                 510

Leu Asp Ser Asp Gly Ser Phe Phe Leu Tyr Ser Lys Leu Thr Val Asp
            515                 520                 525

Lys Ser Arg Trp Gln Gln Gly Asn Val Phe Ser Cys Ser Val Met His
            530                 535                 540

Glu Ala Leu His Asn His Tyr Thr Gln Lys Ser Leu Ser Leu Ser Pro
545                 550                 555                 560

Gly Lys

<210> SEQ ID NO 23
<211> LENGTH: 822
<212> TYPE: PRT
<213> ORGANISM: artificial sequence
<220> FEATURE:
<223> OTHER INFORMATION: FGFR2 IIIb precursor (i.e. with signal
      peptide); GenBank Acc. No. NP_075259.2

<400> SEQUENCE: 23

Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
                20                  25                  30

Leu Glu Pro Glu Glu Pro Pro Thr Lys Tyr Gln Ile Ser Gln Pro Glu
            35                  40                  45
```

```
Val Tyr Val Ala Ala Pro Gly Glu Ser Leu Glu Val Arg Cys Leu Leu
 50                  55                  60
Lys Asp Ala Ala Val Ile Ser Trp Thr Lys Asp Gly Val His Leu Gly
 65                  70                  75                  80
Pro Asn Asn Arg Thr Val Leu Ile Gly Glu Tyr Leu Gln Ile Lys Gly
                 85                  90                  95
Ala Thr Pro Arg Asp Ser Gly Leu Tyr Ala Cys Thr Ala Ser Arg Thr
            100                 105                 110
Val Asp Ser Glu Thr Trp Tyr Phe Met Val Asn Val Thr Asp Ala Ile
        115                 120                 125
Ser Ser Gly Asp Asp Glu Asp Asp Thr Asp Gly Ala Glu Asp Phe Val
    130                 135                 140
Ser Glu Asn Ser Asn Asn Lys Arg Ala Pro Tyr Trp Thr Asn Thr Glu
145                 150                 155                 160
Lys Met Glu Lys Arg Leu His Ala Val Pro Ala Ala Asn Thr Val Lys
                165                 170                 175
Phe Arg Cys Pro Ala Gly Gly Asn Pro Met Pro Thr Met Arg Trp Leu
            180                 185                 190
Lys Asn Gly Lys Glu Phe Lys Gln Glu His Arg Ile Gly Gly Tyr Lys
        195                 200                 205
Val Arg Asn Gln His Trp Ser Leu Ile Met Glu Ser Val Val Pro Ser
    210                 215                 220
Asp Lys Gly Asn Tyr Thr Cys Val Val Glu Asn Glu Tyr Gly Ser Ile
225                 230                 235                 240
Asn His Thr Tyr His Leu Asp Val Val Glu Arg Ser Pro His Arg Pro
                245                 250                 255
Ile Leu Gln Ala Gly Leu Pro Ala Asn Ala Ser Thr Val Val Gly Gly
            260                 265                 270
Asp Val Glu Phe Val Cys Lys Val Tyr Ser Asp Ala Gln Pro His Ile
        275                 280                 285
Gln Trp Ile Lys His Val Glu Lys Asn Gly Ser Lys Tyr Gly Pro Asp
    290                 295                 300
Gly Leu Pro Tyr Leu Lys Val Leu Lys His Ser Gly Ile Asn Ser Ser
305                 310                 315                 320
Asn Ala Glu Val Leu Ala Leu Phe Asn Val Thr Glu Ala Asp Ala Gly
                325                 330                 335
Glu Tyr Ile Cys Lys Val Ser Asn Tyr Ile Gly Gln Ala Asn Gln Ser
            340                 345                 350
Ala Trp Leu Thr Val Leu Pro Lys Gln Gln Ala Pro Gly Arg Glu Lys
        355                 360                 365
Glu Ile Thr Ala Ser Pro Asp Tyr Leu Glu Ile Ala Ile Tyr Cys Ile
    370                 375                 380
Gly Val Phe Leu Ile Ala Cys Met Val Val Thr Val Ile Leu Cys Arg
385                 390                 395                 400
Met Lys Asn Thr Thr Lys Lys Pro Asp Phe Ser Ser Gln Pro Ala Val
                405                 410                 415
His Lys Leu Thr Lys Arg Ile Pro Leu Arg Arg Gln Val Thr Val Ser
            420                 425                 430
Ala Glu Ser Ser Ser Ser Met Asn Ser Asn Thr Pro Leu Val Arg Ile
        435                 440                 445
Thr Thr Arg Leu Ser Ser Thr Ala Asp Thr Pro Met Leu Ala Gly Val
    450                 455                 460
```

```
Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
            485                 490                 495

Val Met Ala Glu Ala Val Gly Ile Asp Lys Asp Lys Pro Lys Glu Ala
        500                 505                 510

Val Thr Val Ala Val Lys Met Leu Lys Asp Asp Ala Thr Glu Lys Asp
    515                 520                 525

Leu Ser Asp Leu Val Ser Glu Met Glu Met Met Lys Met Ile Gly Lys
530                 535                 540

His Lys Asn Ile Ile Asn Leu Leu Gly Ala Cys Thr Gln Asp Gly Pro
545                 550                 555                 560

Leu Tyr Val Ile Val Glu Tyr Ala Ser Lys Gly Asn Leu Arg Glu Tyr
            565                 570                 575

Leu Arg Ala Arg Arg Pro Pro Gly Met Glu Tyr Ser Tyr Asp Ile Asn
        580                 585                 590

Arg Val Pro Glu Glu Gln Met Thr Phe Lys Asp Leu Val Ser Cys Thr
    595                 600                 605

Tyr Gln Leu Ala Arg Gly Met Glu Tyr Leu Ala Ser Gln Lys Cys Ile
610                 615                 620

His Arg Asp Leu Ala Ala Arg Asn Val Leu Val Thr Glu Asn Asn Val
625                 630                 635                 640

Met Lys Ile Ala Asp Phe Gly Leu Ala Arg Asp Ile Asn Asn Ile Asp
            645                 650                 655

Tyr Tyr Lys Lys Thr Thr Asn Gly Arg Leu Pro Val Lys Trp Met Ala
        660                 665                 670

Pro Glu Ala Leu Phe Asp Arg Val Tyr Thr His Gln Ser Asp Val Trp
    675                 680                 685

Ser Phe Gly Val Leu Met Trp Glu Ile Phe Thr Leu Gly Gly Ser Pro
690                 695                 700

Tyr Pro Gly Ile Pro Val Glu Glu Leu Phe Lys Leu Leu Lys Glu Gly
705                 710                 715                 720

His Arg Met Asp Lys Pro Ala Asn Cys Thr Asn Glu Leu Tyr Met Met
            725                 730                 735

Met Arg Asp Cys Trp His Ala Val Pro Ser Gln Arg Pro Thr Phe Lys
        740                 745                 750

Gln Leu Val Glu Asp Leu Asp Arg Ile Leu Thr Leu Thr Thr Asn Glu
    755                 760                 765

Glu Tyr Leu Asp Leu Ser Gln Pro Leu Glu Gln Tyr Ser Pro Ser Tyr
770                 775                 780

Pro Asp Thr Arg Ser Ser Cys Ser Ser Gly Asp Asp Ser Val Phe Ser
785                 790                 795                 800

Pro Asp Pro Met Pro Tyr Glu Pro Cys Leu Pro Gln Tyr Pro His Ile
            805                 810                 815

Asn Gly Ser Val Lys Thr
            820

<210> SEQ ID NO 24
<211> LENGTH: 822
<212> TYPE: PRT
<213> ORGANISM: artificial sequence
<220> FEATURE:
<223> OTHER INFORMATION: FGFR2 IIIb precursor S252W

<400> SEQUENCE: 24
```

```
Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Trp Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
                325                 330                 335

Glu Tyr Ile Cys Lys Val Ser Asn Tyr Ile Gly Gln Ala Asn Gln Ser
            340                 345                 350

Ala Trp Leu Thr Val Leu Pro Lys Gln Gln Ala Pro Gly Arg Glu Lys
        355                 360                 365

Glu Ile Thr Ala Ser Pro Asp Tyr Leu Glu Ile Ala Ile Tyr Cys Ile
    370                 375                 380

Gly Val Phe Leu Ile Ala Cys Met Val Val Thr Val Ile Leu Cys Arg
385                 390                 395                 400

Met Lys Asn Thr Thr Lys Lys Pro Asp Phe Ser Ser Gln Pro Ala Val
                405                 410                 415

His Lys Leu Thr Lys Arg Ile Pro Leu Arg Arg Gln Val Thr Val Ser
```

```
                420             425             430
Ala Glu Ser Ser Ser Met Asn Ser Asn Thr Pro Leu Val Arg Ile
            435             440             445

Thr Thr Arg Leu Ser Ser Thr Ala Asp Thr Pro Met Leu Ala Gly Val
            450             455             460

Ser Glu Tyr Glu Leu Pro Glu Asp Pro Lys Trp Glu Phe Pro Arg Asp
465             470             475             480

Lys Leu Thr Leu Gly Lys Pro Leu Gly Glu Gly Cys Phe Gly Gln Val
            485             490             495

Val Met Ala Glu Ala Val Gly Ile Asp Lys Asp Lys Pro Lys Glu Ala
            500             505             510

Val Thr Val Ala Val Lys Met Leu Lys Asp Asp Ala Thr Glu Lys Asp
            515             520             525

Leu Ser Asp Leu Val Ser Glu Met Glu Met Met Lys Met Ile Gly Lys
530             535             540

His Lys Asn Ile Ile Asn Leu Leu Gly Ala Cys Thr Gln Asp Gly Pro
545             550             555             560

Leu Tyr Val Ile Val Glu Tyr Ala Ser Lys Gly Asn Leu Arg Glu Tyr
            565             570             575

Leu Arg Ala Arg Arg Pro Pro Gly Met Glu Tyr Ser Tyr Asp Ile Asn
            580             585             590

Arg Val Pro Glu Glu Gln Met Thr Phe Lys Asp Leu Val Ser Cys Thr
            595             600             605

Tyr Gln Leu Ala Arg Gly Met Glu Tyr Leu Ala Ser Gln Lys Cys Ile
            610             615             620

His Arg Asp Leu Ala Ala Arg Asn Val Leu Val Thr Glu Asn Asn Val
625             630             635             640

Met Lys Ile Ala Asp Phe Gly Leu Ala Arg Asp Ile Asn Asn Ile Asp
            645             650             655

Tyr Tyr Lys Lys Thr Thr Asn Gly Arg Leu Pro Val Lys Trp Met Ala
            660             665             670

Pro Glu Ala Leu Phe Asp Arg Val Tyr Thr His Gln Ser Asp Val Trp
            675             680             685

Ser Phe Gly Val Leu Met Trp Glu Ile Phe Thr Leu Gly Gly Ser Pro
            690             695             700

Tyr Pro Gly Ile Pro Val Glu Glu Leu Phe Lys Leu Leu Lys Glu Gly
705             710             715             720

His Arg Met Asp Lys Pro Ala Asn Cys Thr Asn Glu Leu Tyr Met Met
            725             730             735

Met Arg Asp Cys Trp His Ala Val Pro Ser Gln Arg Pro Thr Phe Lys
            740             745             750

Gln Leu Val Glu Asp Leu Asp Arg Ile Leu Thr Leu Thr Thr Asn Glu
            755             760             765

Glu Tyr Leu Asp Leu Ser Gln Pro Leu Glu Gln Tyr Ser Pro Ser Tyr
            770             775             780

Pro Asp Thr Arg Ser Ser Cys Ser Ser Gly Asp Asp Ser Val Phe Ser
785             790             795             800

Pro Asp Pro Met Pro Tyr Glu Pro Cys Leu Pro Gln Tyr Pro His Ile
            805             810             815

Asn Gly Ser Val Lys Thr
            820

<210> SEQ ID NO 25
```

<211> LENGTH: 822
<212> TYPE: PRT
<213> ORGANISM: artificial sequence
<220> FEATURE:
<223> OTHER INFORMATION: FGFR2 IIIb precursor P253R

<400> SEQUENCE: 25

```
Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Arg His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
                325                 330                 335

Glu Tyr Ile Cys Lys Val Ser Asn Tyr Ile Gly Gln Ala Asn Gln Ser
            340                 345                 350

Ala Trp Leu Thr Val Leu Pro Lys Gln Gln Ala Pro Gly Arg Glu Lys
        355                 360                 365

Glu Ile Thr Ala Ser Pro Asp Tyr Leu Glu Ile Ala Ile Tyr Cys Ile
    370                 375                 380
```

```
Gly Val Phe Leu Ile Ala Cys Met Val Val Thr Val Ile Leu Cys Arg
385                 390                 395                 400

Met Lys Asn Thr Thr Lys Lys Pro Asp Phe Ser Ser Gln Pro Ala Val
                405                 410                 415

His Lys Leu Thr Lys Arg Ile Pro Leu Arg Arg Gln Val Thr Val Ser
            420                 425                 430

Ala Glu Ser Ser Ser Ser Met Asn Ser Asn Thr Pro Leu Val Arg Ile
        435                 440                 445

Thr Thr Arg Leu Ser Ser Thr Ala Asp Thr Pro Met Leu Ala Gly Val
    450                 455                 460

Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
                485                 490                 495

Val Met Ala Glu Ala Val Gly Ile Asp Lys Asp Lys Pro Lys Glu Ala
                500                 505                 510

Val Thr Val Ala Val Lys Met Leu Lys Asp Asp Ala Thr Glu Lys Asp
            515                 520                 525

Leu Ser Asp Leu Val Ser Glu Met Glu Met Met Lys Met Ile Gly Lys
530                 535                 540

His Lys Asn Ile Ile Asn Leu Leu Gly Ala Cys Thr Gln Asp Gly Pro
545                 550                 555                 560

Leu Tyr Val Ile Val Glu Tyr Ala Ser Lys Gly Asn Leu Arg Glu Tyr
                565                 570                 575

Leu Arg Ala Arg Arg Pro Pro Gly Met Glu Tyr Ser Tyr Asp Ile Asn
                580                 585                 590

Arg Val Pro Glu Glu Gln Met Thr Phe Lys Asp Leu Val Ser Cys Thr
            595                 600                 605

Tyr Gln Leu Ala Arg Gly Met Glu Tyr Leu Ala Ser Gln Lys Cys Ile
    610                 615                 620

His Arg Asp Leu Ala Ala Arg Asn Val Leu Val Thr Glu Asn Asn Val
625                 630                 635                 640

Met Lys Ile Ala Asp Phe Gly Leu Ala Arg Asp Ile Asn Asn Ile Asp
                645                 650                 655

Tyr Tyr Lys Lys Thr Thr Asn Gly Arg Leu Pro Val Lys Trp Met Ala
                660                 665                 670

Pro Glu Ala Leu Phe Asp Arg Val Tyr Thr His Gln Ser Asp Val Trp
            675                 680                 685

Ser Phe Gly Val Leu Met Trp Glu Ile Phe Thr Leu Gly Gly Ser Pro
    690                 695                 700

Tyr Pro Gly Ile Pro Val Glu Glu Leu Phe Lys Leu Leu Lys Glu Gly
705                 710                 715                 720

His Arg Met Asp Lys Pro Ala Asn Cys Thr Asn Glu Leu Tyr Met Met
                725                 730                 735

Met Arg Asp Cys Trp His Ala Val Pro Ser Gln Arg Pro Thr Phe Lys
                740                 745                 750

Gln Leu Val Glu Asp Leu Asp Arg Ile Leu Thr Leu Thr Thr Asn Glu
            755                 760                 765

Glu Tyr Leu Asp Leu Ser Gln Pro Leu Glu Gln Tyr Ser Pro Ser Tyr
    770                 775                 780

Pro Asp Thr Arg Ser Ser Cys Ser Ser Gly Asp Asp Ser Val Phe Ser
785                 790                 795                 800
```

```
Pro Asp Pro Met Pro Tyr Glu Pro Cys Leu Pro Gln Tyr Pro His Ile
            805             810                 815
Asn Gly Ser Val Lys Thr
            820
```

METHOD OF TREATMENT OF CANCERS CHARACTERIZED BY LIGAND-DEPENDENT ACTIVATING MUTATIONS IN FGFR2 WITH FGFR1 ECD PROTEINS

This application is a continuation of U.S. application Ser. No. 13/509,068, now U.S. Pat. No. 8,614,183, which is a national stage of PCT Application No. PCT/US2010/56627, filed Nov. 12, 2010, which claims the benefit of U.S. Provisional Application No. 61/261,291, filed Nov. 13, 2009. Each of those applications is incorporated by reference herein in its entirety for any purpose.

FIELD OF THE INVENTION

The present invention relates to the use of Fibroblast Growth Factor Receptor I (FGFR1) extracellular domain (ECD) proteins for treatment of cancers characterized by ligand-dependent activating mutations in Fibroblast Growth Factor Receptor 2 (FGFR2).

BACKGROUND AND SUMMARY OF THE INVENTION

The Fibroblast Growth Factor (FGF) and Fibroblast Growth Factor Receptor (FGFR) proteins are involved in a number of cell signalling events. There are 4 different FGFRs (FGFR1, FGFR2, FGFR3, and FGFR4), each with different specificities for the 22 different FGFs. In addition, some of the FGFRs are alternatively spliced, giving rise to further patterns of ligand specificity. For example, FGFR2 IIIb is generally expressed in epithelial tissue and is activated upon binding by one set of FGFs whereas FGFR2 IIIc is generally expressed in mesenchymal tissue and is activated by a different set of FGFs.

Certain cancers and genetic disorders are characterized by activating mutations in the FGFR2 amino acid sequence. For example, subsets of patients with various cancers, such as endometrial, breast, lung, gastric, and ovarian cancers, show mutations in FGFR2. (See, for example, the Catalog of Somatic Mutations in Cancer (COSMIC) at www.sanger.ac.uk/genetics/CGP/cosmic/ providing a repository of somatic changes reported in the FGFR family.) These FGFR2 activating mutations may occur in the extracellular domain, for example, at the hinge region between the IgII and IgIII domains or within the IgIII domain, or in the intracellular tyrosine kinase domain. (See FIG. 1.) In general, mutations in the IgII-IgIII hinge region and IgIII domain may alter the ligand specificity of the receptor, for example, increasing the affinity of the receptor for its normal ligands and/or increasing the promiscuity of the receptor for various other ligands. Thus, these mutations are ligand dependent, meaning that their effects depend on the binding of FGFR2 to one or more of its ligands. In some instances, an alteration in the RNA splicing pattern of the mutant FGFR2 may be observed. In contrast, mutations in the tyrosine kinase domain are thought to be generally ligand independent, meaning that the FGFR2 is active in both the presence and the absence of its ligands.

Endometrial cancer, for example, is a common cancer in industrialized countries but has poor survival rates for those who cannot be treated surgically. Currently the majority of patients are treated with hysterectomy, while there are no curative treatments for patients whose cancers either cannot be surgically resected or whose cancers recur after surgery. Hence, there is a need for non-surgical treatments for this cancer. Several publications have reported that FGFR2 mutations are present in about 15-16% of endometrial carcinomas. (See, e.g., P. M. Pollock et al., *Oncogene* 26: 7158-7162 (2007); A. Dutt et al., *Proc. Nat'l. Acad. Sci. USA* 105(25): 8713-8717 (2008); M. Katoh, *Int. J. Oncol.* 33: 233-237 (2008); WO2008/118877; WO2005/115363.) Several such mutations are located in the IgII-IgIII hinge region and IgIII domain of FGFR2. A commonly observed FGFR2 mutation in endometrial tumor cells is S252W, found in about 7% of cases. In addition, a P253R mutation was found in about 2% of endometrial cancer cases. (See Id.; FIG. 1.)

These S252W and P253R mutations are the same mutations found in the germline of patients with the genetic disease Apert Syndrome, which causes craniosynostosis and syndactyl). Structural and biochemical studies of the FGFR2S252W mutant receptor suggest that S252W and P253R mutants may cause the FGFR2 protein to bind more tightly to its normal FGF ligands as well as to bind other FGF ligands to which it normally does not bind. (See K. Yu et al., *Proc. Natl. Acad. Sci. USA* 97: 14536-41 (2000); O. A. Ibrahimi et al., *Proc. Natl. Acad. Sci. USA* 98: 7182-87 (2001).) In addition, FGFR2 is alternatively spliced and its function is regulated in part through the expression of different splice isoforms with different ligand specificities in different tissues. For example, Yu et al. (*Proc. Natl. Acad. Sci. USA* 97: 14536-41 (2000)) reported that the FGFR2 Mb form is expressed in epithelial cells and may be activated upon binding to FGF7 and FGF10 whereas the FGFR2 IIIc form is expressed in mesenchymal cells and may be activated by binding to FGF2, FGF4, FGF6, FGF8, and FGF9. (See also FIG. 1.) Yu et al. also reported that the S252W mutation may disrupt this splicing-based regulation of FGFR2 function. The S252W FGFR2 IIIb form not only may bind more tightly to its normal ligands such as FGF7 and FGF10, but it may also be activated by the FGFR2 IIIc ligands FGF2, FGF6, and FGF9.

The present invention relates to the use of R1Mut4 to treat cancers, for example endometrial cancers, characterized by expression of an FGFR2 IIIb protein with a point mutation at position 252 and/or position 253, such as S252W or P253R. The present invention also relates to the use of other FGFR1ECDs to treat cancers characterized by ligand-dependent activating mutations of FGFR2, such as, for example, endometrial cancer.

The present inventors have found that an FGFR1ECD fusion molecule called R1Mut4 (SEQ ID NO:22) inhibits the growth of endometrial carcinoma cells expressing an S252W mutant FGFR2 IIIb protein, both in vitro and in a mouse xenograft model. (See FIGS. 2-7.) In the mouse xenograft model, R1Mut4 dramatically inhibited growth of a tumor derived from endometrial carcinoma cells carrying the FGFR2S252W mutation. (See FIG. 7.) The present inventors have also found that R1Mut4 inhibits tumor growth in a dose-dependent fashion in a therapeutic (or established) xenograft endometrial cancer model using human endometrial carcinoma MFE-280 cells with a S252W mutated FGFR2 genomic locus. (See FIG. 8.) Furthermore, R1Mut4 partially inhibited cell growth in the HCC1143 breast carcinoma cell line carrying the FGFR2 R203C mutation. (See FIGS. 9 and 10.)

The present invention also relates to inhibiting the growth of tumor cells expressing either the point mutation serine 252 to tryptophan of the FGFR2 protein or the point mutation proline 253 to arginine of the FGFR2 protein, comprising exposing the tumor cells to an amount of an FGFR1 ECD fusion molecule comprising the amino acid sequence of SEQ ID NO:22 effective to inhibit growth of the tumor cells.

The present invention further relates to treating a cancer in a subject, comprising administering a therapeutically effective amount of an FGFR1 ECD fusion molecule comprising the amino acid sequence of SEQ ID NO:22 to the subject, wherein the cancer is characterized by having tumor cells expressing either the point mutation serine 252 to tryptophan of the FGFR2 protein or the point mutation proline 253 to arginine of the FGFR2 protein.

BRIEF DESCRIPTION OF THE DRAWINGS

The accompanying drawings, which are incorporated in and constitute a part of this specification, illustrate several aspects of the invention and are not to be treated as limiting the invention.

DETAILED DESCRIPTION OF THE EMBODIMENTS

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

The terms "polypeptide" and "protein" are used interchangeably to refer to a polymer of amino acid residues, comprising natural or non-natural amino acid residues, and are not limited to a minimum length. Thus, peptides, oligopeptides, dimers, multimers, and the like are included within the definition. Both full-length proteins and fragments thereof are encompassed by the definition. The terms also include post-translational modifications of the polypeptide, including, for example, glycosylation, sialylation, acetylation, and phosphorylation.

An "FGF ligand" or "FGF" is a fibroblast growth factor, or variant or fragment thereof, which binds to an FGFR.

An "extracellular domain" ("ECD") is the portion of a polypeptide that extends beyond the transmembrane domain into the extracellular space.

A "fibroblast growth factor receptor" ("FGFR") polypeptide, as used herein, is a polypeptide comprising the entirety or a portion of FGFR1, FGFR2, FGFR3, or FGFR4 including all naturally occurring isoforms or allelic variants. "FGFR1," for example, refers to a polypeptide having the amino acid sequence of any one of the known FGFR1 polypeptides, such as FGFR1-IIIb and FGFR1-IIIc, and any variant, precursor, or fragment thereof, including those described in U.S. Pat. Nos. 6,656,728; 6,384,191; 5,229,501; 6,255,454; 6,344,546; 5,474,914; and 5,288,855. FGFR1-IIIb and FGFR1-IIIc differ from each other in their IgIII domains (defined below). "FGFR2," as used herein, refers to a polypeptide having the amino acid sequence of any known FGFR2 polypeptide, for example, FGFR2-IIIb and FGFR2-IIIc, and any variants and precursors thereof. Splice isoforms FGFR2-IIIb and FGFR2-IIIc, for example, differ from each other in the IgIII domains. Exemplary FGFR2 precursor sequences are shown in Table 4, SEQ ID NOs:23-25.

The "FGFR2 IgII-IgIII hinge region" encompasses the portion of the FGFR2 ECD polypeptide sequence between the IgII and IgIII domain portions. The IgII-IgIII hinge region includes, for example, amino acid positions 252 and 253. (See FIG. 1.)

Figure 1:
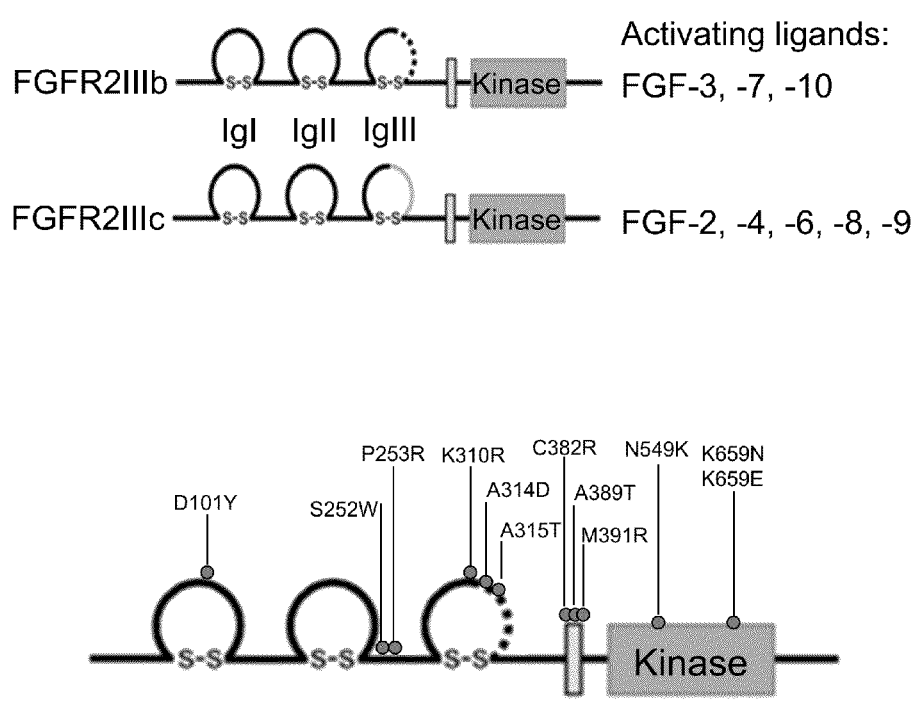
FIG. 1 illustrates the structure and domain organization of FGFR2 and shows the positions of mutations identified by Dutt et al. (*Proc. Nat'l. Acad. Sci. USA* 105(25): 8713-8717 (2008)) in endometrial cancer cell lines. The upper portion depicts the domain structure of FGFR2 as well as the IIIb and IIIc splice variants. The IIIb form is generally expressed in epithelial tissues and may be activated by one or more of FGFs 3, 7, and 10, for example, whereas the IIIc form is generally expressed in mesenchymal tissues and may be activated by one or more of FGFs 2, 4, 6, 8, and 9, for example. The three Ig domains are depicted IgI, IgII, and IgIII, while the transmembrane region is shown as a shaded bar after the three Ig domains and the tyrosine kinase domain is denoted "kinase."

The "FGFR2 IgIII domain" refers to the third Ig domain in the ECD of FGFR2 (See FIG. 1). The IgIII domain encompasses, for example, amino acids 290, 310, 314, and 315.

"Wildtype" refers to a non-mutated version of a gene, allele, genotype, polypeptide, or phenotype, or a fragment of any of these. It may occur in nature or be produced recombinantly.

A "mutant" or "mutation" used herein may encompass one or more amino acid exchanges within the amino acid sequence of the polypeptide, e.g. point mutations. It may also encompass deletions or insertions of amino acids at the N-terminal or C-terminal end or within the amino acid sequence.

FGFR2 mutants herein include allelic variants naturally occurring in tumor cells or the germline of patients with genetic disease.

The term "signal peptide" refers to a sequence of amino acid residues that facilitates secretion of a polypeptide from a mammalian cell. A signal peptide is typically cleaved upon export of the polypeptide from the mammalian cell. A "precursor" FGFR protein sequence includes a signal peptide. Certain exemplary signal peptides include, but are not limited to, the signal peptides of FGFR1, FGFR2, FGFR3, and FGFR4, such as, for example, the amino acid sequences depicted in Table 4, SEQ ID NOs: 13-16. Certain exemplary signal peptides also include signal peptides from heterologous proteins. Proteins according to this invention are typically without a signal peptide, although certain embodiments may optionally comprise a signal peptide.

An "FGFR2 activating mutant" as used herein refers to a mutation that increases the biological activity of FGFR2, for example, a mutation causing FGFR2 to become activated more readily in comparison to the wildtype FGFR2 in response to certain stimuli. A "ligand independent" activating mutant is one in which the biological effect of the mutation is observed regardless of the presence and absence of its ligands, such as a mutation that causes activation of the receptor in the absence of ligand binding. Examples include mutations in the FGFR2 tyrosine kinase domain that result in the kinase being constitutively switched on, as well as examples in which a cysteine is substituted for another amino acid, causing a disulfide bridge to form between two FGFR2 receptors, resulting in dimerization in the absence of a ligand. A "ligand dependent activating mutant" is one whose biological effects depend on the binding of FGFR2 to one or more of its ligands, such as a mutation that causes alterations in the ligand binding properties of FGFR2.

"FGFR1 ECD" refers to a genus consisting of the following sub-genuses: native FGFR1 ECDs, FGFR1 ECD variants, FGFR1 ECDs comprising an Ig domain III chosen from IIIb and IIIc (the FGFR1 ECDs are also referred to as FGFR1-IIIb ECDs or FGFR1-IIIc ECDs), native FGFR1-IIIb ECD, native FGFR1-IIIc ECD, FGFR1-IIIb ECD variants, FGFR1-IIIc ECD variants, FGFR1 ECD fragments, native FGFR1 ECD fragments, variants of FGFR1 ECD fragments, FGFR1 ECD glycosylation mutants, and FGFR1 ECD fusion molecules, as well as non-human FGFR1 ECDs. In some embodiments, the FGFR1 ECD comprises a signal peptide whereas in others it does not. (See, e.g. SEQ ID NOs: 1 and 2.) All FGFR1 ECDs all are able to bind FGF2.

As used herein, the terms "native FGFR1 ECD" and "wildtype FGFR1 ECD" are used interchangeably to refer to an FGFR1 ECD with a naturally occurring amino acid sequence. Native FGFR1 ECDs and wildtype FGFR1 ECDs also include FGFR1 ECD splice variants or isoforms. As used herein, the terms FGFR1 ECD "splice variants" or "splice isoforms" are used interchangeably to refer to alternative splice forms of FGFR1 ECD, such as FGFR1-IIIb and FGFR1-IIIc ECD. Exemplary native FGFR1 ECDs are SEQ ID NOs:1, 2, and 12 depicted in Table 4.

As used herein, the term "FGFR1-IIIb ECD" refers to the FGFR1 ECD with an Ig domain III chosen from native IIIb and IIIb variants. The term "FGFR1-IIIc ECD" refers to the FGFR1 ECD with an Ig domain III chosen from native IIIc and IIIc variants.

As set forth above, native FGFR1-IIIb and native FGFR1-IIIc ECDs are FGFR1 ECDs wherein the polypeptide sequence contains the splice isoform of IIIb or IIIc of the third Ig domain (Ig domain III) in the C-terminal region of the ECD. As used herein, the terms "native IIIb" and "native IIIc" refer to the native sequence of the Ig domain III of the splice isoforms IIIb and IIIc, respectively.

As used herein, the term "FGFR1 ECD variants" refers to FGFR1 ECDs containing amino acid additions, deletions, and/or substitutions in comparison to the native FGFR1 ECDs. FGFR1 ECD variants retain the ability to bind FGF2 Amino acid additions and deletions may be made at the amino-terminus, at the carboxy-terminus, and/or within the ECD sequence. Exemplary FGFR1 ECD variants that contain amino acid deletions have the amino acid sequences of SEQ ID NOs: 3-7. FGFR1 ECD variants may include amino acid substitutions within the FGFR1 ECD that inhibit N-glycosylation, referred to interchangeably herein as "FGFR1 ECD glycosylation mutants" and "FGFR1 ECD N-glycan mutants." Exemplary FGFR1 ECD variants are depicted in SEQ ID NOs: 3-11.

As used herein, "FGFR1-IIIb ECD variant" refers to FGFR1-IIIb ECD containing amino acid additions, deletions, and/or substitutions in comparison to native FGFR1-IIIb ECD. FGFR1-IIIb ECD variants retain the ability to bind FGF2. The term "FGFR1-IIIc ECD variant" refers to FGFR1-IIIc ECD containing amino acid additions, deletions, and/or substitutions in comparison to native FGFR1-IIIc ECD. FGFR1-IIIc ECD variants retain the ability to bind FGF2. As used herein, the terms "IIIb variant" and "IIIc variant" refer to a variant sequence of the Ig domain III of the splice isoforms IIIb and IIIc, respectively, said variant sequence containing amino acid additions, deletions, and/or substitutions.

As used herein, the term "native FGFR1 ECD fragment" refers to an FGFR1 ECD having an amino acid sequence modified in that amino acid residues have been deleted from the amino-terminus and/or from the carboxy-terminus of the polypeptide, wherein the fragment retains the ability to bind FGF2. Examples are shown in SEQ ID NOs: 3-7.

As used herein, the terms "FGFR1 ECD fragment variant" and "variant of FGFR1 ECD fragment" are used interchangeably to refer to FGFR1 ECDs containing, not only amino acid deletions from the amino- and/or carboxy-terminus of native FGFR1 ECD, but also amino acid additions, deletions, and/or substitutions within the retained portion of the FGFR1 ECD. FGFR1 ECD fragment variants retain the ability to bind FGF2.

Collectively, "native FGFR1 ECD fragments" and "FGFR1 ECD fragment variants" form the genus of "FGFR1 ECD fragments."

FGFR1 ECD variants may include amino acid substitutions within the FGFR1 ECD sequence that inhibit N-glycosylation, referred to interchangeably herein as "FGFR1 ECD glycosylation mutants" and "FGFR1 ECD N-glycan mutants." In certain embodiments, one or more amino acids are mutated to prevent glycosylation at that site in the polypeptide. FGFR1 ECD glycosylation mutants retain the ability to bind FGF2.

The terms "FGFR1 ECD fusion molecule," "FGFR1 ECD fusion protein," and "FGFR1 ECD fusion" are used interchangeably herein to refer to an FGFR1 ECD comprising an FGFR1 ECD polypeptide and a fusion partner. FGFR1 ECD fusions retain the ability to bind FGF2. FGFR1 ECD fusions may be constructed based upon any of the FGFR1 ECD genera defined above or any of the FGFR1 ECD species described elsewhere herein. The fusion partner may be linked to either the amino-terminus or the carboxy-terminus of the polypeptide. In certain embodiments, the polypeptide and the fusion partner are covalently linked. If the fusion partner is also a polypeptide, the polypeptide and the fusion partner may be part of a continuous amino acid sequence. In such cases, the polypeptide and the fusion partner may be translated as a single polypeptide from a coding sequence that encodes both the polypeptide and the fusion partner. In certain embodiments, the polypeptide and the fusion partner are covalently linked through other means, such as, for example, a chemical linkage other than a peptide bond. Methods of covalently linking polypeptides to other molecules (for example, fusion partners) are known in the art. In certain embodiments, the polypeptide and the fusion partner are non-covalently linked. In certain such embodiments, they may be linked, for example, using binding pairs. Exemplary binding pairs include, but are not limited to, biotin and avidin or streptavidin, an antibody and its antigen, etc.

A "fusion partner" is any component of a fusion molecule in addition to the FGFR1 ECD. A fusion partner may comprise a polypeptide, such as a fragment of an immunoglobulin molecule, or a non-polypeptide moiety, for example, polyethylene glycol. The fusion partner may comprise an oligomerization domain such as an Fc domain of a heavy chain immunoglobulin. Certain exemplary fusion partners include, but are not limited to, an immunoglobulin Fc domain, albumin, and polyethylene glycol. The amino acid sequences of certain exemplary Fc domains are shown in SEQ ID NOs: 17-21. Exemplary FGFR1 ECD Fc fusions include, for example, R1Mut4, which has the sequence of SEQ ID NO:22.

A "fragment crystallizable (Fc) polypeptide" is the portion of an antibody molecule that interacts with effector molecules and cells. It comprises the C-terminal portions of the immunoglobulin heavy chains. As used herein, an Fc polypeptide comprises a fragment of the Fc domain with one or more biological activity of an entire Fc polypeptide. An "effector function" of the Fc polypeptide is an action or activity performed in whole or in part by an antibody in response to a stimulus and may include complement fixation or ADCC (antibody-dependent cellular cytotoxicity) induction. Exemplary Fc sequences are provided in Table 4, SEQ ID NOs:17-21.

The terms "antibody" and "immunoglobulin" refer to a protein, generated by the immune system, made synthetically, or made recombinantly, that is capable of recognizing and binding to a specific antigen; antibodies are commonly known in the art. They can be polyclonal antibodies, monoclonal antibodies, single chain antibodies or antigen binding fragments thereof.

In certain embodiments, the FGFR1 ECD amino acid sequence is derived from that of a non-human mammal. Such FGFR1 ECDs are termed "non-human FGFR1 ECDs." In such embodiments, the FGFR1 ECD sequence may be derived from mammals including, but not limited to, rodents, simians, felines, canines, equines, bovines, porcines, ovines, caprines, mammalian laboratory animals, mammalian farm animals, mammalian sport animals, and mammalian pets. In other words, non-human FGFR1 ECD includes the corresponding native FGFR1 ECD, FGFR1 ECD variants, FGFR1 ECD fragments, native FGFR1 ECD fragments, variants of FGFR1 ECD fragments, and FGFR1 ECD fusion molecules.

The terms "subject" and "patient" are used interchangeably herein to refer to mammals, including, but not limited to, rodents, simians, humans, felines, canines, equines, bovines, porcines, ovines, caprines, mammalian laboratory animals, mammalian farm animals, mammalian sport animals, and mammalian pets.

"Treatment" or "treat" as used herein, covers any administration or application of a therapeutic for disease in a mammal, including a human, and includes inhibiting the disease, arresting its development, or relieving the disease, for example, by causing regression, or restoring or repairing a lost, missing, or defective function; or stimulating an inefficient process. Treatment may achieved with surgery, radiation, and/or administration of one or more molecules, including, but not limited to, small molecules and polymers, such as polypeptides.

The terms "inhibition" and "inhibit" used herein in reference to cell or tumor growth, encompass, for example, a partial or complete reduction of the rate with which tumor size or cell number is increasing compared to the rate prior to the start of treatment. The terms also encompass reductions in tumor size and cell number compared to the tumor size or cell number prior to the start of treatment. Inhibition of cell growth or tumor size may occur, for example, by cell death, apoptosis, and inhibition of further cell division.

A "therapeutically effective amount" of a molecule according to the invention means an amount that is sufficient to treat a condition and/or to inhibit growth of tumor cells in at least a subset of subjects when given alone or in combination with other treatments.

"Cancer" and "tumor" are interchangeable terms that refer to any abnormal cell or tissue growth or proliferation in an animal. As used herein, the terms "cancer" and "tumor" encompass solid and hematological/lymphatic cancers and also encompass malignant, pre-malignant, and benign growth, such as dysplasia.

A "pharmaceutically acceptable carrier" refers to a non-toxic solid, semisolid, or liquid filler, diluent, encapsulating material, formulation auxiliary, or carrier conventional in the art for use with a therapeutic agent for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. For example, if the therapeutic agent is to be administered orally, the carrier may be a gel capsule. If the therapeutic agent is to be administered subcutaneously, the carrier ideally is not irritable to the skin and does not cause injection site reaction.

A "vector" refers to a polynucleotide that is used to express a polypeptide of interest in a host cell. A vector may include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that can be used in colorimetric assays, e.g., β-galactosidase). One skilled in the art can select suitable vector elements for the particular host cell and application at hand.

A "host cell" refers to a cell that can be or has been a recipient of a vector or isolated polynucleotide. Host cells may be prokaryotic cells or eukaryotic cells. Exemplary eukaryotic cells include mammalian cells, such as primate or non-primate animal cells; fungal cells; plant cells; and insect cells. Certain exemplary mammalian cells include, but are not limited to, 293 and CHO cells.

The term "isolated" as used herein refers to a molecule that has been separated from at least some of the components with which it is typically found in nature. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide.

Exemplary Methods of the Invention

The present invention provides, inter alia, a method of treating a cancer characterized by a ligand dependent activating mutation in FGFR2 in a subject, comprising administering a therapeutically effective amount of an FGFR1 ECD to the subject.

The present invention also provides a method of inhibiting the growth of tumor cells expressing a ligand dependent activating mutation in FGFR2, comprising administering a therapeutically effective amount of an FGFR1 ECD to a subject in need thereof.

The present invention also provides a method of administering an FGFR1 ECD to a subject in need thereof, comprising:

(a) determining if tumor cells from the subject express a ligand dependent activating mutation in FGFR2; and
(b) if the tumor cells do express the ligand dependent activating mutation in FGFR2, then administering a therapeutically effective amount of an FGFR1 ECD to the subject.

And the present invention provides a method of inhibiting the growth of tumor cells expressing a ligand dependent activating mutation in FGFR2, comprising exposing the tumor cells, in vitro, in vivo, or in a subject, to an amount of an FGFR1 ECD effective to inhibit growth of the tumor cells.

Within any of those methods, the cancer or tumor cells may be endometrial, gastric, lung, or ovarian cancer or tumor cells. Furthermore, the ligand dependent activating mutation in FGFR2 may comprise at least one substitution, insertion, or deletion in the IgIII domain of the FGFR2 protein, and/or at least one substitution, insertion, or deletion in the IgII-IgIII hinge region of the FGFR2 protein.

The mutation may be, for example, a point mutation of the serine residue at amino acid position 252 of the FGFR2 protein, such as a serine 252 to tryptophan substitution, or a serine to phenylalanine or serine to leucine substitution. Alternatively, the mutation may be a point mutation of the proline residue at amino acid position 253 of the FGFR2 protein, such as a proline 253 to arginine substitution. In addition, the mutation may comprise any one or more of the specific set of FGFR2 IgII-IgIII hinge region and IgIII domain mutations mentioned below. In some embodiments, the mutation in the IgII-IgIII hinge region or IgIII domain does not include a substitution of a wildtype amino acid for a cysteine residue.

In some embodiments of the methods above, the FGFR1 ECD is a native FGFR1 ECD or an FGFR1 ECD variant. FGFR1 ECD variants retain the ability to bind FGF2. In some embodiments, the FGFR1 ECD comprises the amino acid sequence of any one of SEQ ID NOs: 1-22, such as, for example, any one of SEQ ID NOs: 1-12 or 1 and 3-12 or SEQ ID NO:22. In certain embodiments, the FGFR1 ECD is an FGFR1 ECD splice variant. In certain embodiments, the FGFR1 ECD is a FGFR1-IIIb ECD or FGFR1-IIIc ECD. In certain embodiments, the FGFR1 ECD is an FGFR1 ECD fragment. FGFR1 ECD fragments retain the ability to bind FGF2. In certain embodiments, the FGFR1 ECD is a native FGFR1 ECD fragment. In certain embodiments, the FGFR1 ECD is a variant of an FGFR1 ECD fragment. In certain embodiments, the FGFR1 ECD is a splice variant of an FGFR1 ECD fragment. In certain embodiments, the FGFR1 ECD is an FGFR1 ECD glycosylation mutant.

In the claimed methods, the FGFR1 ECD may also be an FGFR1 ECD fusion molecule, such as one in which the FGFR1 ECD is fused to an Fc polypeptide, PEG, albumin, or another fusion partner described herein. In some embodiments, the FGFR1 ECD fusion molecule comprises an Fc, wherein the Fc comprises one of SEQ ID NOs: 17-21. In some embodiments the FGFR1 ECD fusion molecule comprises SEQ ID NO:22 and in others the FGFR1 ECD fusion molecule is R1Mut4, which consists of SEQ ID NO:22.

In some embodiments, the FGFR1 ECD lacks a signal peptide. In other embodiments, the FGFR1 ECD includes a signal peptide, such as a signal peptide from FGFR1, FGFR2, FGFR3, FGFR4, or a heterologous protein. Exemplary signal peptides are depicted in SEQ ID NOs:13-16 of Table 4.

In some embodiments the FGFR1 ECD is a non-human FGFR1 ECD.

In some embodiments, the FGFR1 ECD is administered before, after, or substantially contemporaneously with another treatment such as chemotherapy, radiation therapy, biologic therapy, or surgery. In some embodiments, the FGFR1 ECD is administered with a pharmaceutically acceptable carrier.

In some embodiments of the methods above, the FGFR1 ECD fusion molecule may be R1Mut4 and the mutation may be, for example, a point mutation of the serine residue at amino acid position 252 of the FGFR2 protein, such as a serine 252 to tryptophan substitution, or a serine to phenylalanine or serine to leucine substitution. Alternatively, the mutation may be a point mutation of the proline residue at amino acid position 253 of the FGFR2 protein, such as a proline 253 to arginine substitution.

FGFR2 Ligand Dependent Activating Mutations and Cancers Characterized by Such Mutations FGFR2 activating mutations have been identified in endometrial, breast, lung, gastric, and ovarian cancers, for example. In some embodiments, the ligand dependent activating mutant in FGFR2 is located at the IgII-IgIII hinge region of the FGFR2 protein while in others it is located in the IgIII domain. For example, amino acid substitutions at positions 252, 253 and 315 are encompassed within the scope of this invention, such as S252W, S252F, and S252L, P253R, and A315T mutations found in endometrial cancer cell lines. (See, e.g. Pollock et al. and Dutt et al., cited above, and Ibrahimi et al. (2004) *Hum Mol. Genet.* 13(19):2313-24.) Amino acid substitutions K310R and A314D, identified in endometrial cancer cell lines, as well as S267P, found in gastric cancers, D293N, found in lung cancers, and G272V, found in ovarian cancers are also proposed to be ligand dependent mutations and thus are also encompassed within this invention. Substitutions C383R, A390T, M392 R, also found in endometrial tumor cell lines, are in the transmembrane-spanning region of FGFR2. They are also proposed to be ligand dependent. These amino acid positions are defined based upon the precursor FGFR2 sequence NP_075259.2, also depicted in SEQ ID NO: 23 of Table 4, wherein the first amino acid of the signal peptide is assigned the amino acid number 1. (See, e.g. Pollock et al. and Dutt et al., cited above, and also WO2008/118877; WO2005/115363; Katoh M. (2008) *Int J. Oncol.* 33(2):233-7; Ibrahimi et al. (2004) *Hum Mol. Genet.* 13(19):2313-24; Monsonego-Ornan E et al. (2000) *Mol Cell Biol.* 20(2):516-22; Davies et al. (2005) *Cancer Res.* 65:7591-7595; and Jang et al. (2001) *Cancer Res.* 61:3541-3543, for descriptions of these and other ligand dependent activating mutations in FGFR2 previously identified that are within the scope of this invention.) Substitutions in the IgII-IgIII hinge and IgIII domain from a wildtype amino acid to a cysteine residue may be ligand independent and are excluded in some embodiments of the invention. An example is W290C. Substitutions at amino acid 203 of FGFR2 are also in the scope of the invention. An example is R203C. Substitutions at amino acid 212 of FGFR2 are also in the scope of the invention. An example is Q212K. Substitutions at amino acid 659 of FGFR2 are also in the scope of the invention. An example is K659M. Substitutions at amino acid 770 of FGFR2 are also in the scope of the invention. An example is L770V. Substitutions at amino acid 211 of FGFR2 are also in the scope of the invention. An example is N211I. Substitutions at amino acid 283 of FGFR2 are also in the scope of the invention. An example is D283N. Substitutions at amino acid 29 of FGFR2 are also in the scope of the invention. An example is W29C. Substitutions at amino acid 380 of FGFR2 are also in the scope of the invention. An example is I380V. Substitutions at amino acid 544 of FGFR2 are also in the scope of the invention. An example is H544Q. Substitutions at amino acid 612 of FGFR2 are also in the scope of the invention. An example is R612T. Substitutions at amino acid 375 of FGFR2 are also in the scope of the invention. An example is Y375C. Substitutions at amino acid 267 of FGFR2 are also in the scope of the invention. An example is S267P.

In some embodiments, the FGFR2 ligand dependent activating mutation is a point mutation at amino acid position 252 and/or at 253. (Compare, e.g. SEQ ID NOs: 23-25 showing FGFR2 wildtype precursor, S252W, and P253R amino acid sequences, respectively.) For example, the mutation may be an S252W, S252F, S252L, P253R, or S252F-P253S mutation or a combination of the above. The S252W and P253R mutations have been found in 7% and 2% of endometrial carcinomas in humans, for example.

In some embodiments, a disruption of the normal tissue-specific splicing patterns of FGFR2 is observed, such as, for example, tumor cells in mesenchymal tissue expressing an epithelial splice variant of FGFR2, or tumor cells in epithelial tissue expressing a mesenchymal splice variant. The present inventors, for example, examined three endometrial cancer cell lines, HEC-1-B, expressing wildtype FGFR2, MFE-280, which appears to be homozygous for FGFR2 S252W, and MFE-319, which is heterozygous for FGFR2S252W. The mutation status and splicing pattern of the FGFR2RNAs were found to be as follows:

TABLE 1

FGFR2 RNA Status of Endometrial Tumor Cell Lines

| Cell line | No. clones analyzed | S252W mutation status | FGFR2 IIIb RNA | FGFR2 IIIc RNA |
|---|---|---|---|---|
| HEC-1-B | 15 | 15/15 (100%) wildtype | 1/15 (7%) | 14/15 (93%) |
| MFE-280 | 16 | 16/16 (100%) S252W | 15/15 (100%) | 0/15 (0%) |
| MFE-319 | 15 | 9/15 S252W 6/16 wildtype (40% S252W) | 15/15 (100%) | 0/15 (0%) |

Hence, the MFE-280 and MFE-319 cells expressing the S252W mutation also produced FGFR2 in the IIIb epithelial-specific splice form whereas the HEC-1-B tumor cell line expressing wildtype FGFR2 expressed the protein in the IIIc mesenchymal-specific splice form. Moreover, the HEC-1-B cells were found to express low levels of the epithelial protein marker E-cadherin protein, consistent with their expression of predominantly mesenchymal FGFR2, whereas MFE-280 and MFE-319 cells were found to express higher levels of E-cadherin, which correlates with the FGFR2 splicing data.

Structural and biochemical studies of the FGFR2 S252W mutant receptor suggest that S252W FGFR2 IIIb, the form expressed in the endometrial cell lines MFE-280 and MFE-319, not only may bind more tightly to normal FGFR2 IIIb ligands such as FGF7 and FGF10, but may also be activated by FGFR2 IIIc ligands such as FGF2, FGF6, and FGF9. (See K. Yu et al., *Proc. Natl. Acad. Sci. USA* 97: 14536-41 (2000); O. A. Ibrahimi et al., *Proc. Natl. Acad. Sci. USA* 98: 7182-87 (2001).)

FGFR1 ECDs

FGFR1 ECD molecules are provided. In certain embodiments, an FGFR1 ECD molecule is isolated. FGFR1 ECDs consist of native FGFR1 ECDs, FGFR1 ECD variants, FGFR1 ECDs comprising an Ig domain III chosen from IIIb and IIIc, native FGFR1-IIIb ECD, native FGFR1-IIIc ECD, FGFR1-IIIb ECD variants, FGFR1-IIIc ECD variants, FGFR1 ECD fragments, native FGFR1 ECD fragments, variants of FGFR1 ECD fragments, FGFR1 ECD glycosylation mutants, and FGFR1 ECD fusion molecules, as well as non-human FGFR1 ECDs. All FGFR1 ECDs all are able to bind FGF2. In some embodiments, the FGFR1 ECD includes a signal peptide, either from FGFR1, or from another FGFR, or from another protein. In other embodiments, no signal peptide is included.

The FGFR1 ECD proteins of the invention can comprise an entire FGFR1 ECD, including that of wildtype FGFR1-IIIb or wildtype FGFR1-IIIc ECD, or for example a variant or fragment of the FGFR1 ECD that retains the ability to bind FGF2. A native FGFR1-IIIc ECD is depicted in SEQ ID NOs:1-2, for example, with and without its signal sequence, and in SEQ ID NO:12. In some embodiments, a variant of the native FGFR1 ECD, for example, having a deletion of one or more and up to 22 amino acid residues counting from the C-terminus of the native FGFR1 ECD of SEQ ID NO:1, is provided. In some embodiments, the FGFR1 ECD has the final 22 amino acids of the C-terminus deleted, while in others, the FGFR1 ECD has the final 19, 14, 9, 8, or 4 C-terminal amino acids deleted in comparison to SEQ ID NO:1. (See, e.g., SEQ ID NOs:3-7 in Table 4 below.)

Examples of such variants include those having the C-terminal amino acid residues LYLE or MTSPLYLE or VMTSPLYLE or AVMTSPLYLE or EERPAVMTSPLYLE or LEERPAVMTSPLYLE or ALEERPAVMTSPLYLE deleted as compared to either a native FGFR1-IIIb or FGFR1-IIIc. Further examples include those having the C-terminal amino acid residues KALEERPAVMTSPLYLE or RPVAKALEERPAVMTSPLYLE deleted as compared to a native FGFR1-IIIb or EALEERPAVMTSPLYLE deleted as compared to a native FGFR1-IIIc. Point mutations or internal deletions or insertions within the ECD amino acid sequence may also be made within the FGFR1 ECD so long as FGF2 binding activity is retained. Examples include point mutations, for example, but not limited to amino acids P364 and A365 or P364G, P364M, and M367N mutations compared to native FGFR1 IIIb and FGFR1 IIIc sequences.

FGFR1 ECD Fusion Molecules

FGFR1 ECD fusion molecules herein refer to a protein comprising a sequence of amino acids corresponding to an FGFR1 ECD and a fusion partner. The fusion partner may be joined to either the N-terminus or the C-terminus of the FGFR1 ECD polypeptide and the FGFR1 ECD may be joined to either the N-terminus or the C-terminus of the fusion partner.

Fusion Partners and Conjugates

In certain embodiments, a fusion partner is selected that imparts favorable pharmacokinetics and/or pharmacodynamics on the FGFR1 ECD protein. For example, in certain embodiments, a fusion partner is selected that increases the half-life of the FGFR1 ECD fusion molecule relative to the corresponding FGFR1 ECD without the fusion partner. By increasing the half-life of the molecule, a lower dose and/or less-frequent dosing regimen may be required in therapeutic treatment. Further, the resulting decreased fluctuation in FGFR1 ECD serum levels may improve the safety and tolerability of the FGFR1 ECD-based therapeutics.

Many different types of fusion partners are known in the art. One skilled in the art can select a suitable fusion partner according to the intended use. Non-limiting exemplary fusion partners include polymers, polypeptides, lipophilic moieties, and succinyl groups. Exemplary polypeptide fusion partners include serum albumin and an antibody Fc domain. Exemplary polymer fusion partners include, but are not limited to, polyethylene glycol, including polyethylene glycols having branched and/or linear chains.

Oligomerization Domain Fusion Partners

In various embodiments, oligomerization offers certain functional advantages to a fusion protein, including, but not limited to, multivalency, increased binding strength, and the combined function of different domains. Accordingly, in certain embodiments, a fusion partner comprises an oligomerization domain, for example, a dimerization domain. Exemplary oligomerization domains include, but are not limited to, coiled-coil domains, including alpha-helical coiled-coil domains; collagen domains; collagen-like domains, and certain immunoglobulin domains. Certain exemplary coiled-coil polypeptide fusion partners include the tetranectin coiled-coil domain; the coiled-coil domain of cartilage oligomeric matrix protein; angiopoietin coiled-coil domains; and leucine zipper domains. Certain exemplary collagen or collagen-like oligomerization domains include, but are not limited to, those found in collagens, mannose binding lectin, lung surfactant proteins A and D, adiponectin, ficolin, conglutinin, macrophage scavenger receptor, and emilin.

Antibody Fc Immunoglobulin Domain Fusion Partners

Many Fc domains that could be used as fusion partners are known in the art. One skilled in the art can select an appropriate Fc domain fusion partner according to the intended use. In certain embodiments, a fusion partner is an Fc immunoglobulin domain. An Fc fusion partner may be a wildtype Fc found in a naturally occurring antibody, a variant thereof, or a fragment thereof. Non-limiting exemplary Fc fusion partners include Fcs comprising a hinge and the CH2 and CH3 constant domains of a human IgG, for example, human IgG1, IgG2, IgG3, or IgG4. Certain additional Fc fusion partners include, but are not limited to, human IgA and IgM. In certain embodiments, an Fc fusion partner comprises a C237S mutation. In certain embodiments, an Fc fusion partner comprises a hinge, CH2, and CH3 domains of human IgG2 with a P331S mutation, as described in U.S. Pat. No. 6,900,292. Certain exemplary Fc domain fusion partners are shown in Table 4.

Albumin Fusion Partners and Albumin-Binding Molecule Fusion Partners

In certain embodiments, a fusion partner is an albumin. Certain exemplary albumins include, but are not limited to, human serum album (HSA) and fragments of HSA that are capable of increasing the serum half-life and/or bioavailability of the polypeptide to which they are fused. In certain embodiments, a fusion partner is an albumin-binding molecule, such as, for example, a peptide that binds albumin or a molecule that conjugates with a lipid or other molecule that binds albumin. In certain embodiments, a fusion molecule comprising HSA is prepared as described, e.g., in U.S. Pat. No. 6,686,179.

Polymer Fusion Partners

In certain embodiments, a fusion partner is a polymer, for example, polyethylene glycol (PEG). PEG may comprise branched and/or linear chains. In certain embodiments, a fusion partner comprises a chemically-derivatized polypeptide having at least one PEG moiety attached. Pegylation of a polypeptide may be carried out by any method known in the art. One skilled in the art can select an appropriate method of pegylating a particular polypeptide, taking into consideration the intended use of the polypeptide. Certain exemplary PEG attachment methods include, for example, EP 0 401 384; Malik et al., *Exp. Hematol.*, 20:1028-1035 (1992); Francis, *Focus on Growth Factors*, 3:4-10 (1992); EP 0 154 316; EP 0 401 384; WO 92/16221; and WO 95/34326. As non-limiting examples, pegylation may be performed via an acylation reaction or an alkylation reaction, resulting in attachment of one or more PEG moieties via acyl or alkyl groups. In certain embodiments, PEG moieties are attached to a polypeptide through the α- or ε-amino group of one or more amino acids, although any other points of attachment known in the art are also contemplated.

Pegylation by acylation typically involves reacting an activated ester derivative of a PEG moiety with a polypeptide. A non-limiting exemplary activated PEG ester is PEG esterified to N-hydroxysuccinimide (NHS). As used herein, acylation is contemplated to include, without limitation, the following types of linkages between a polypeptide and PEG: amide, carbamate, and urethane. See, e.g., Chamow, *Bioconjugate Chem.*, 5:133-140 (1994). Pegylation by alkylation typically involves reacting a terminal aldehyde derivative of a PEG moiety with a polypeptide in the presence of a reducing agent. Non-limiting exemplary reactive PEG aldehydes include PEG propionaldehyde, which is water stable, and mono C1-C10 alkoxy or aryloxy derivatives thereof. See, e.g., U.S. Pat. No. 5,252,714.

In certain embodiments, a pegylation reaction results in poly-pegylated polypeptides. In certain embodiments, a pegylation reaction results in mono-, di-, and/or tri-pegylated polypeptides. Further, desired pegylated species may be separated from a mixture containing other pegylated species and/or unreacted starting materials using various purification techniques known in the art, including among others, dialysis, salting-out, ultrafiltration, ion-exchange chromatography, gel filtration chromatography, and electrophoresis.

Exemplary Attachment of Fusion Partners

The fusion partner may be attached, either covalently or non-covalently, to the amino-terminus or the carboxy-terminus of the FGFR1 ECD. The attachment may also occur at a location within the FGFR1 ECD other than the amino-terminus or the carboxy-terminus, for example, through an amino acid side chain (such as, for example, the side chain of cysteine, lysine, histidine, serine, or threonine).

In either covalent or non-covalent attachment embodiments, a linker may be included between the fusion partner and the FGFR1 ECD. Such linkers may be comprised of amino acids and/or chemical moieties. Exemplary methods of covalently attaching a fusion partner to an FGFR1 ECD include, but are not limited to, translation of the fusion partner and the FGFR1 ECD as a single amino acid sequence and chemical attachment of the fusion partner to the FGFR1 ECD. When the fusion partner and the FGFR1 ECD are translated as single amino acid sequence, additional amino acids may be included between the fusion partner and the FGFR1 ECD as a linker. In certain embodiments, the linker is glycine-serine ("GS"). In certain embodiments, the linker is selected based on the polynucleotide sequence that encodes it, to facilitate cloning the fusion partner and/or FGFR1 ECD into a single expression construct (for example, a polynucleotide containing a particular restriction site may be placed between the polynucleotide encoding the fusion partner and the polynucleotide encoding the FGFR1 ECD, wherein the polynucleotide containing the restriction site encodes a short amino acid linker sequence).

When the fusion partner and the FGFR1 ECD are covalently coupled by chemical means, linkers of various sizes can typically be included during the coupling reaction. Several methods of covalent coupling of a polypeptide to another molecule (i.e. fusion partner) are known. The polypeptide and fusion partner can also be non-covalently coupled. Exemplary methods of non-covalently attaching a fusion partner to an FGFR1 ECD include, but are not limited to, attachment through a binding pair. Exemplary binding pairs include, but are not limited to, biotin and avidin or streptavidin, an antibody and its antigen, etc.

Nucleic Acid Molecules Encoding the Polypeptides of the Invention

Nucleic acid molecules comprising polynucleotides that encode FGFR1 ECDs can be constructed using known recombinant DNA techniques.

In certain embodiments, a polynucleotide encoding a polypeptide of the invention comprises a nucleotide sequence that encodes a signal peptide, which, when translated, will be fused to the amino-terminus of the FGFR1 polypeptide. In other embodiments, the nucleotide sequence does not include a sequence encoding a signal peptide. As discussed above, the signal peptide may be the native signal peptide, the signal peptide of FGFR1, FGFR2, FGFR3, or FGFR4, or may be another heterologous signal peptide. The amino acid sequences for certain exemplary FGFR signal peptides are shown, e.g., in Table 4. See also SEQ ID NOs:1 and 2, which depict an FGFR1 ECD with and without a signal peptide. Certain exemplary signal peptides are known in the art, and are described, e.g., in the online Signal Peptide Database maintained by the Department of Biochemistry, National University of Singapore, proline.bic.nus.edu.sg/spdb/index.html (see also Choo et al., *BMC Bioinformatics*, 6: 249 (2005)); and in PCT Publication No. WO 2006/081430.

In certain embodiments, the nucleic acid molecule comprising the polynucleotide encoding the gene of interest is an expression vector that is suitable for expression in a selected host cell.

Expression and Production of the Proteins of the Invention

The polypeptides may be expressed from a vector in a host cell. In certain embodiments, a vector is selected that is optimized for expression of polypeptides in CHO—S or CHO—S-derived cells. Exemplary such vectors are described, e.g., in Running Deer et al., *Biotechnol. Prog.* 20:880-889 (2004). In certain embodiments, a vector is chosen for in vivo expression of the polypeptides of the invention in animals, including humans. In certain such embodiments, expression of the polypeptide is under the control of a promoter that functions in a tissue-specific manner. For example, liver-specific promoters are described, e.g., in PCT Publication No. WO 2006/076288. Other methods of expression and purification are mentioned in WO2007/014123 and in U.S. patent application Ser. No. 12/535,479 and PCT Application PCT/US09/52704, each filed Aug. 4, 2009

The polypeptides of the invention can be expressed, in various embodiments, in prokaryotic cells, such as bacterial cells; or eukaryotic cells, such as fungal cells, plant cells, insect cells, and mammalian cells. Such expression may be carried out, for example, according to procedures known in the art. Certain exemplary eukaryotic cells that can be used to express polypeptides include, but are not limited to, Cos cells, including Cos 7 cells; 293 cells, including 293-6E and 293-T cells; CHO cells, including CHO—S and DG44 cells; and NS0 cells.

Introduction of a nucleic acid vector into a desired host cell can be accomplished by any method known in the art, including, but not limited to, calcium phosphate transfection, DEAE-dextran mediated transfection, cationic lipid-mediated transfection, electroporation, transduction, infection, etc. Certain exemplary methods are described, e.g., in Sambrook et al., *Molecular Cloning, A Laboratory Manual*, 3$^{rd}$ ed. Cold Spring Harbor Laboratory Press (2001). Nucleic acids may be transiently or stably transfected in the desired host cells, according to methods known in the art.

In certain embodiments, a polypeptide can be produced in vivo in an animal that has been engineered or transfected with a nucleic acid molecule encoding the polypeptide, according to methods known in the art.

Purification of FGFR1 ECD Polypeptides

The polypeptides of the invention can be purified by various methods known in the art. Such methods include, but are not limited to, the use of affinity matrices, ion exchange chromatography, and/or hydrophobic interaction chromatography. Suitable affinity ligands include any ligands of the FGFR1 ECD or of the fusion partner, or antibodies thereto. For example, in the case of a fusion protein, a Protein A, Protein G, Protein A/G, or an antibody affinity column may be used to bind to an Fc fusion partner to purify a polypeptide of the invention. Antibodies to the polypeptides of the invention may also be used to purify the polypeptides of the invention. Hydrophobic interactive chromatography, for example, a butyl or phenyl column, may also suitable for purifying certain polypeptides. Many methods of purifying polypeptides are known in the art.

Methods of constructing DNA coding sequences, vectors, and host cells for FGFR1 ECDs, as well as methods of expressing and purifying FGFR1 ECDs are also described, for example, in WO2007/014123 and in U.S. patent application Ser. No. 12/535,479 and PCT Application PCT/US09/52704, each filed Aug. 4, 2009.

Therapeutic Compositions

Routes of Administration and Carriers

In various embodiments, the FGFR1 ECDs of the invention can be administered in vivo by a variety of routes, including intravenous, intra-arterial, subcutaneous, parenteral, intranasal, intramuscular, intracardiac, intraventricular, intratracheal, buccal, rectal, intraperitoneal, intradermal, topical, transdermal, and intrathecal, or otherwise by implantation or inhalation. The subject compositions can be formulated into preparations in solid, semi-solid, liquid, or gaseous forms, such as tablets, capsules, powders, granules, ointments, solutions, suppositories, enemas, injections, inhalants, and aerosols. Nucleic acid molecules encoding the polypeptides of the invention can be coated onto gold microparticles and delivered intradermally by a particle bombardment device, or "gene gun," as described in the literature (see, e.g., Tang et al., *Nature* 356:152-154 (1992)).

In various embodiments, compositions comprising the polypeptides of the invention are provided in formulation with pharmaceutically acceptable carriers, a wide variety of which are known in the art (see, e.g., Gennaro, *Remington: The Science and Practice of Pharmacy with Facts and Comparisons: Drugfacts Plus*, 20th ed. (2003); Ansel et al., *Pharmaceutical Dosage Forms and Drug Delivery Systems*, 7$^{th}$ ed., a Lippencott Williams and Wilkins (2004); Kibbe et al., *Handbook of Pharmaceutical Excipients*, 3$^{rd}$ ed., Pharmaceutical Press (2000)). Various pharmaceutically acceptable carriers, which include vehicles, adjuvants, carriers, and diluents, are available to the public. Moreover, various pharmaceutically acceptable auxiliary substances, such as pH adjusting and buffering agents, tonicity adjusting agents, stabilizers, wetting agents and the like, are also available to the public. Certain non-limiting exemplary carriers include saline, buffered saline, dextrose, water, glycerol, ethanol, and combinations thereof.

In various embodiments, compositions comprising FGFR1 ECDs of the invention can be formulated for injection by dissolving, suspending, or emulsifying them in an aqueous or nonaqueous solvent, such as vegetable or other oils, synthetic aliphatic acid glycerides, esters of higher aliphatic acids, or propylene glycol; and if desired, with conventional additives such as solubilizers, isotonic agents, suspending agents, emulsifying agents, stabilizers and preservatives. In various embodiments, the compositions may be formulated for inhalation, for example, using pressurized acceptable propellants such as dichlorodifluoromethane, propane, nitrogen, and the like. The compositions may also be formulated, in various embodiments, into sustained release microcapsules, such as with biodegradable or non-biodegradable polymers. A non-limiting exemplary biodegradable formulation includes poly lactic acid-glycolic acid polymer. A non-limiting exemplary non-biodegradable formulation includes a polyglycerin fatty acid ester. Certain methods of making such formulations are described, for example, in EP 1 125 584 A1.

Pharmaceutical packs and kits comprising one or more containers, each containing one or more doses of the polypeptides of the invention are also provided. In certain embodiments, a unit dosage is provided wherein the unit dosage contains a predetermined amount of a composition comprising a polypeptide of the invention, with or without one or more additional agents. In certain embodiments, such a unit dosage is supplied in single-use prefilled syringe for injection. In various embodiments, the composition contained in the unit dosage may comprise saline, sucrose, or the like; a buffer, such as phosphate, or the like; and/or be formulated within a stable and effective pH range. Alternatively, in certain embodiments, the composition may be provided as a lyophilized powder that can be reconstituted upon addition of an appropriate liquid, for example, sterile water. In certain embodiments, the composition comprises one or more substances that inhibit protein aggregation, including, but not limited to, sucrose and arginine. In certain embodiments, a composition of the invention comprises heparin and/or a proteoglycan.

Pharmaceutical compositions are administered in an amount effective for treatment and/or prophylaxis of the specific indication. The effective amount is typically dependent on the weight of the subject being treated, his or her physical or health condition, the extensiveness of the condition to be treated, and/or the age of the subject being treated. In general, the polypeptides of the invention are to be administered in an amount in the range of about 50 µg/kg body weight to about 100 mg/kg body weight per dose. Optionally, the polypeptides of the invention can be administered in an amount in the range of about 100 µg/kg body weight to about 20 mg/kg body weight per dose. Further optionally, the polypeptides of the invention can be administered in an amount in the range of about 0.5 mg/kg body weight to about 20 mg/kg body weight per dose.

The compositions comprising the polypeptides of the invention can be administered as needed to subjects. Determination of the frequency of administration can be made by persons skilled in the art, such as an attending physician based on considerations of the condition being treated, age of the subject being treated, severity of the condition being treated, general state of health of the subject being treated and the like. In certain embodiments, an effective dose of the polypeptide of the invention is administered to a subject one or more times. In various embodiments, an effective dose of the polypeptide of the invention is administered to the subject at least once a month, at least twice a month, once a week, twice a week, or three times a week. In various embodiments, an effective dose of the polypeptide of the invention is administered to the subject for at least a week, at least a month, at least three months, at least six months, or at least a year.

Combination Therapy

FGFR1 ECDs may be administered alone or with other modes of treatment. They may be provided before, substantially contemporaneous with, or after other modes of treatment, for example, surgery, chemotherapy, radiation therapy, or the administration of a biologic, such as a therapeutic antibody.

EXAMPLES

Example 1

An FGFR1 ECD Fc Fusion Molecule Inhibits FGFR2S252W Mutant Endometrial Carcinoma Cell Lines in Tissue Culture The endometrial carcinoma cell line, HEC-1-B (Cat #HTB-113), encoding a wildtype genomic FGFR2 locus (Dutt et al. 2008; PNAS 105(25):8713-7) was obtained from American Type Culture Collection (ATCC; Manassas, Va.) and maintained in Minimum Essential Medium Eagle with Earle's balanced salt solution (ATCC) supplemented with 2 mM L-glutamine 0.1 mM non-essential amino acids, 10% fetal bovine serum (FBS; all from Mediatech, Inc. Manassas, Va.) and 1.0 mM Sodium Pyruvate (Sigma-Aldrich, Milwaukee, Wis.). Endometrial cell lines MFE-280 (DSMZ cat#. ACC 410) and MFE-319 (DSMZ cat# ACC 423) with a S252W mutation in the FGFR2 gene (Dutt et al. 2008; PNAS 105(25):8713-7) were obtained from Deutsche Sammlung von Mikroorganismen and Zellkulturen GmbH (DSMZ: Germany) and maintained in 40% RPMI 1640, 40% Minimum Essential Medium (with Earle's salts) supplemented with 2 mM L-glutamine, 20% FBS (all from Mediatech, Inc) and 1×ITS (Insulin, Transferrin and Sodium Selenite, from Sigma-Aldrich). Cells were incubated at 37° C. at 5% $CO_2$. Mutation status of the FGFR2 receptor in the cell lines was confirmed by PCR amplification and sequencing of exon 7 of the genomic FGFR2 gene using primer sequences described by Dutt et al. (2008). To determine the impact of an FGFR1 ECD Fc fusion molecule on endometrial carcinoma cell lines in tissue culture, cells were plated in a Microtest™ 96-well tissue culture plate (Becton Dickenson, Franklin Lakes, N.J.) at a density of 5×10$^3$ or 2.5×10$^4$ cells/well in medium containing 10%, 1% or 0.1% FBS in the presence or absence of 15 µg/ml R1Mut4 (SEQ ID NO:22) or a CSF1R-ECD Fc fusion protein (a negative control). Plates were then incubated at 37° C. at 5% $CO_2$ for 4 days and then assayed to determine the impact of R1Mut4 on cell number and proliferation.

To determine cell number, the CellTiter-Glo® Luminescent Cell Viability Assay (Promega, Madison, Wis.) was employed. CellTiter-Glo® is a homogeneous method of determining the number of viable cells in culture based on quantitation of the ATP present, an indicator of metabolically active cells. In brief, CellTiter-Glo® Reagent was added to each well of the tissue culture plate at a volume equal to the volume of cell culture medium present in each well (100 µl), the contents mixed for 2 minutes on an orbital shaker to induce cell lysis and then the plate incubated for 10 minutes at room temperature. Luminescence was then determined on an EnVision™ Multilabel Plate Reader (PerkinElmer, Boston, Mass.) with a 0.2 second integration time. Results were expressed as relative light units (RLU)/well.

Figure 2:
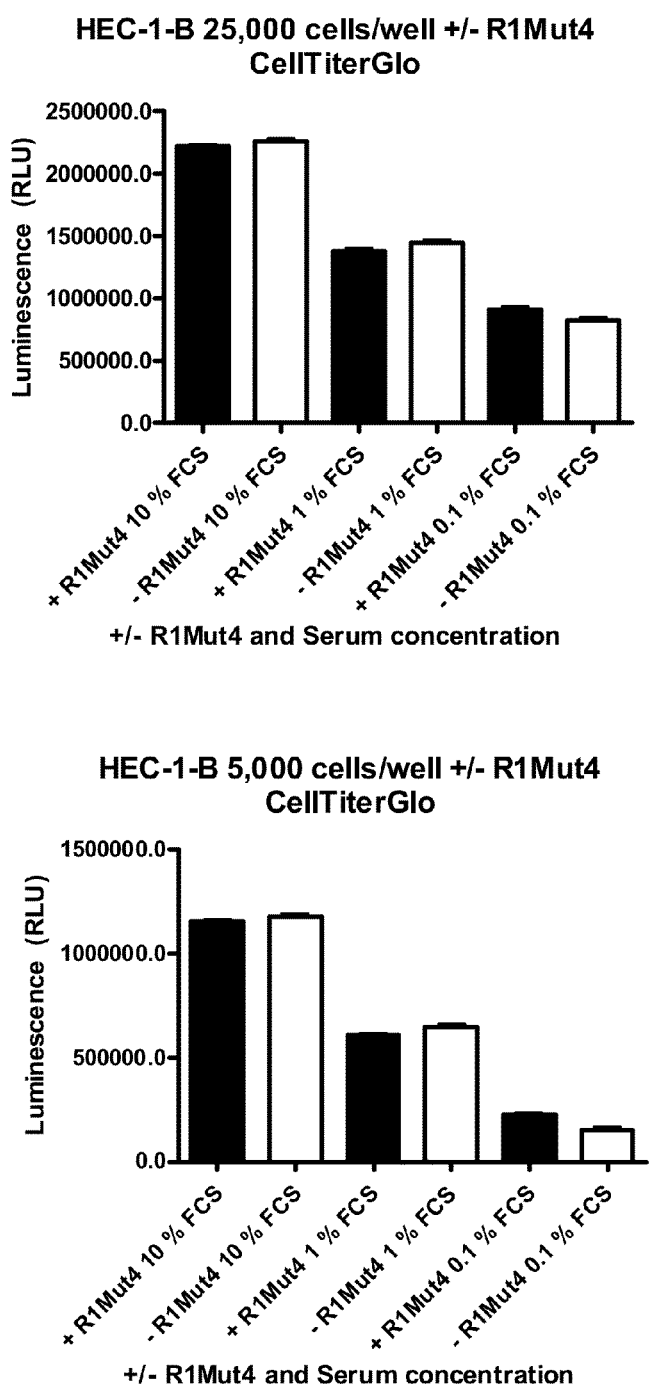
FIG. 2 shows the effect of R1Mut4, an FGFR1ECD Fc fusion molecule of (SEQ ID NO:22), on cell number in a cell line expressing wildtype FGFR2 protein (HEC-1-B) as measured using a CellTiter-Glo® assay. Black bars denote the presence of R1Mut4 while white bars denote the absence of R1Mut4. R1Mut4 did not affect the cell number in the FGFR2 wildtype expressing HEC-1-B cells.
Figure 3:
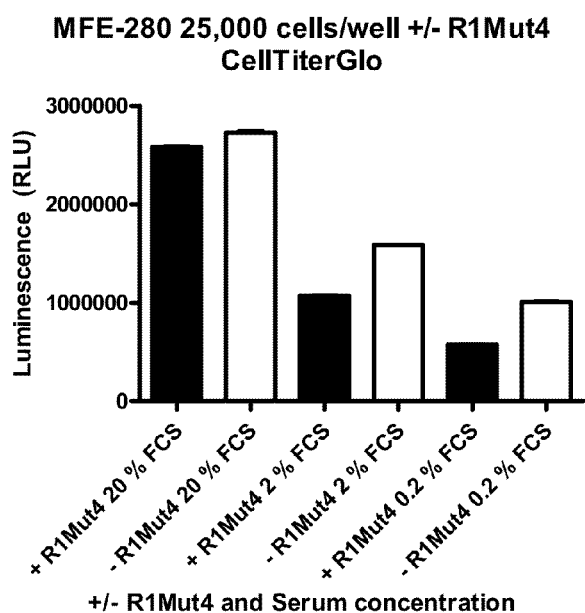
FIG. 3 shows the effect of R1Mut4 on cell number in a cell lines with the S252W FGFR2 mutation (MFE-280) as measured using a CellTiter-Glo® assay. R1Mut4 (black bars) significantly reduced cell number (P=>0.001) in MFE-280 cells.
Figure 3:
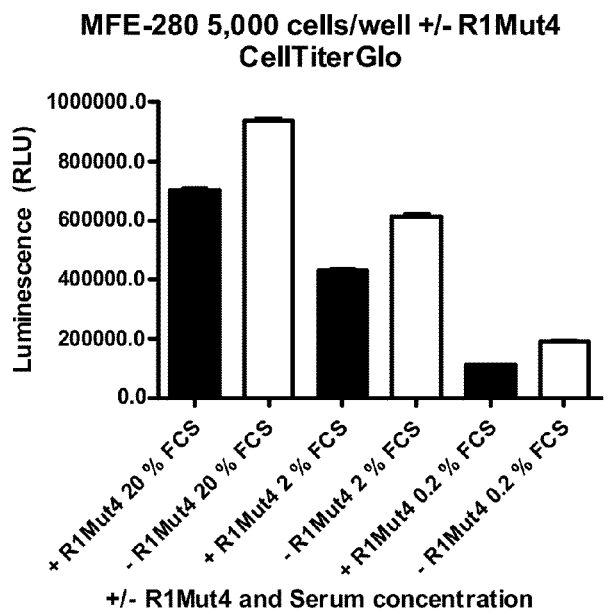

Results from the CellTiter-Glo® assay demonstrated that cell number in the HEC-1-B cell line expressing the wildtype FGFR2 protein was un-effected by R1Mut4 incubation in tissue culture (FIG. 2). In comparison, cell number of the MFE-280 (FIG. 3) and MFE-319 (data not shown) cell lines expressing the S252W mutated FGFR2 was significantly (P=>0.001) reduced by R1Mut4 incubation. P-values were determined using an unpaired t-test. (See *Mathematical Statistics and Data Analysis*, 1988, Wadsworth & Brooks, Pacific Grove, Calif.)

To determine the impact of R1Mut4 on cell proliferation the tritiated thymidine ([3H]-TdR) incorporation assay was employed. Following incubation of endometrial carcinoma cell lines with R1Mut4 or a CSF1R-ECD Fc negative control, tritiated thymidine ([3H]-TdR; PerkinElmer, Boston, Mass.) was added at activity of 1 µCi/well. After 16-h exposure, tritiated thymidine incorporation was assessed. Cells were washed with Dulbecco's phosphate-buffered saline (DPBS; Mediatech, Inc) and removed from cell culture surface by incubation with trypsin-EDTA (Mediatech, Inc). The cell suspension (200 p. 1) was then removed from the tissue culture plate using a FilterMate harvester (PerkinElmer) and filtered through a UniFilter-96 GF/B (PerkinElmer) plate. Cells were lysed using 95% ethanol and 40 p. 1 of Microscint 40 (PerkinElmer) scintillant fluid added per well. Thymidine incorporation was determined as counts per minute (cpm) on a Topcount NXT (PerkinElmer) scintillation counter. Results were expressed as cpm/well.

Figure 4:
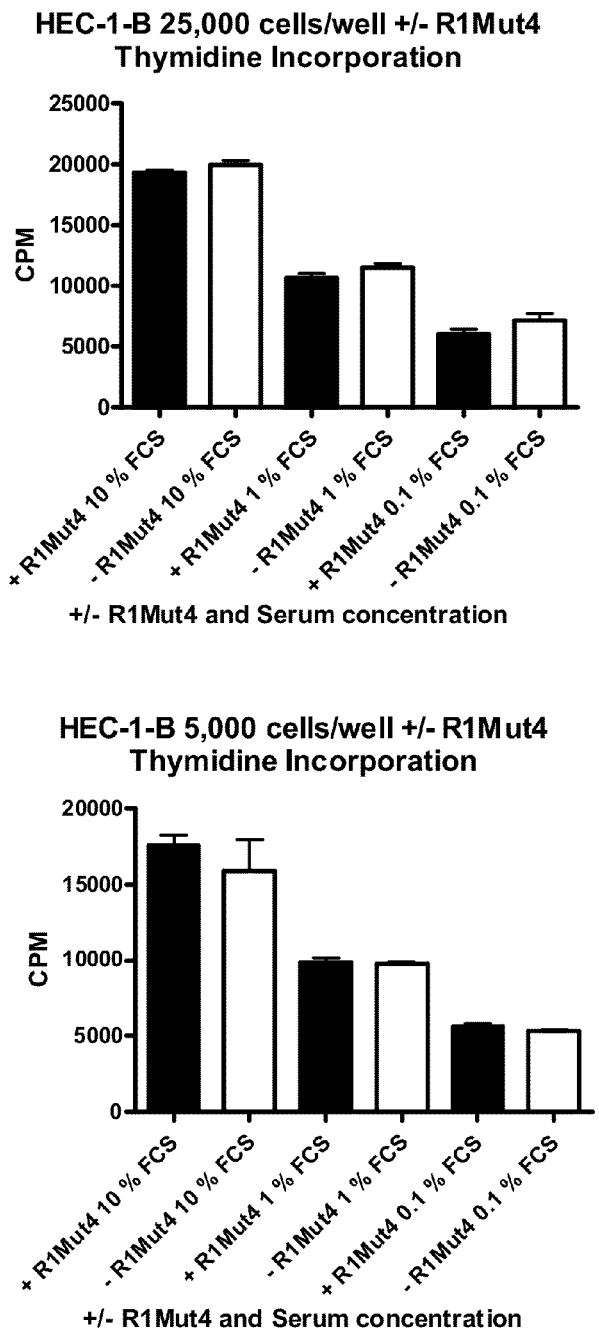
FIG. 4 shows the effect of R1Mut4 on cell number in a cell line expressing wildtype FGFR2 protein (HEC-1-B) as measured using a tritiated thymidine incorporation assay. R1Mut4 did not affect the cell number in the FGFR2 wildtype expressing HEC-1-B cells.
Figure 5:
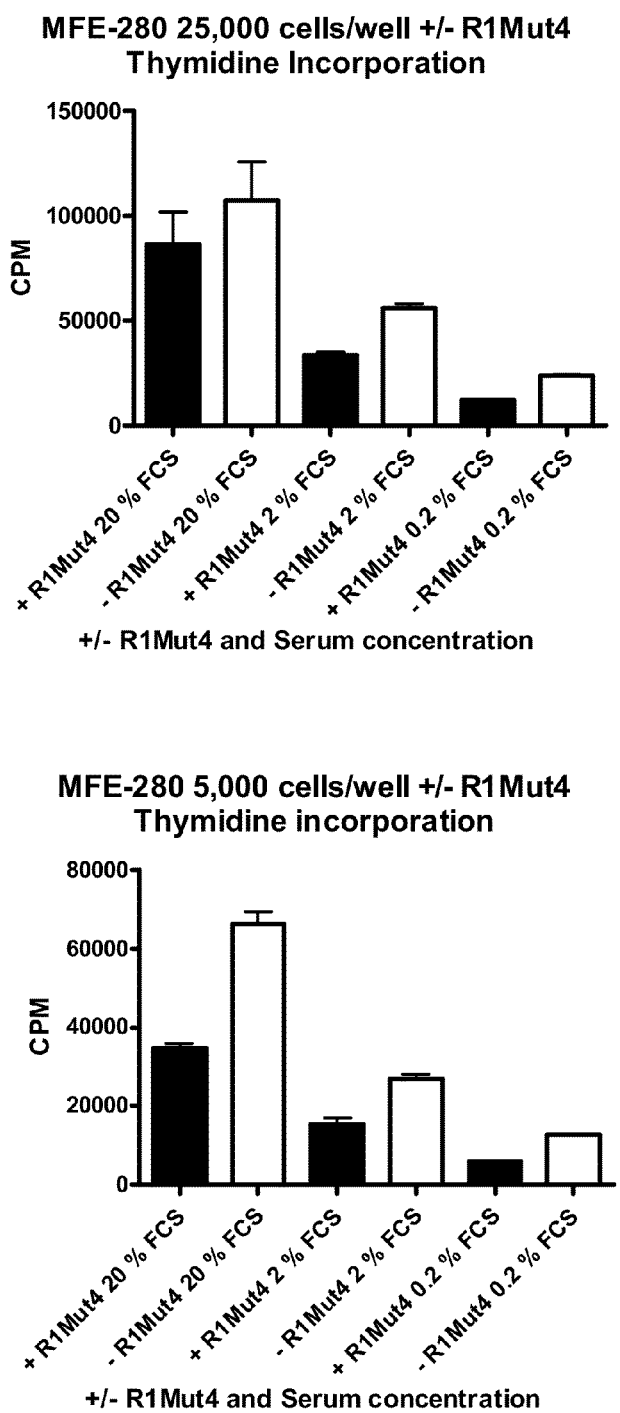
FIG. 5 shows the effect of R1Mut4 on cell number in a cell lines with the S252W FGFR2 mutation (MFE-280) as measured using a tritiated thymidine incorporation assay. R1Mut4 (black bars) led to at least a 50% reduction in cell number (P=>0.0001) in MFE-280 cells.
Figure 6:
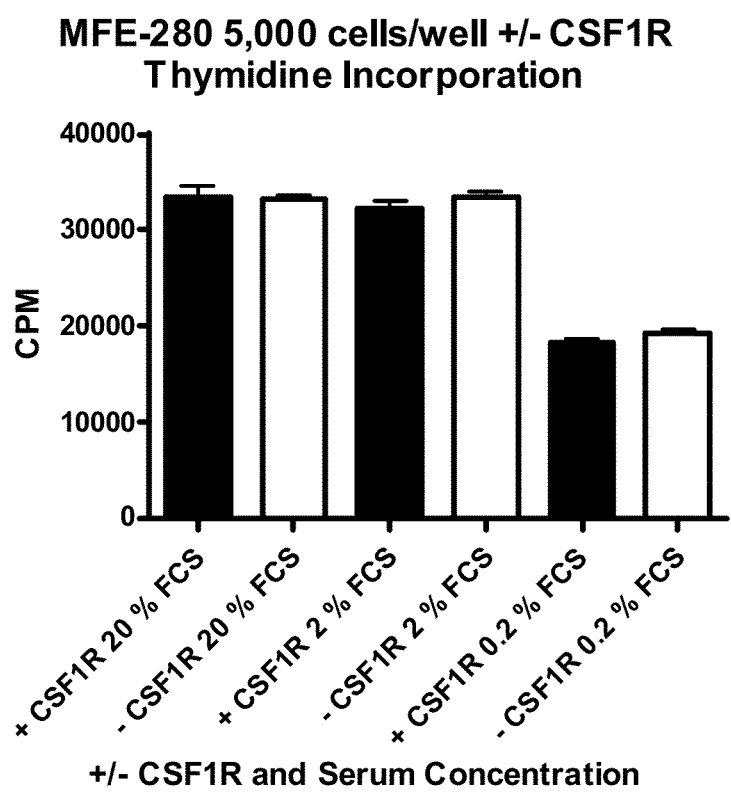
FIG. 6 shows the effect of a colony stimulating factor 1 receptor ECD Fc fusion (CSF1R-ECD Fc) negative control protein on cell number in MFE-280 cells homozygous for the S252W FGFR2 mutation using a tritiated thymidine incorporation assay. The control protein did not impact cell number.

In the tritiated thymidine incorporation assay, R1Mut4 had no impact on HEC-1-B proliferation in cell culture (FIG. 4). In comparison, the MFE-280 cell line displayed a ≥50% reduction in cell proliferation (FIG. 5; P=<0.0001). R1Mut4 mediated inhibition of cell proliferation (approximately 20% reduction) was also observed in the MFE-319 cell line (data not shown). The control protein CSF1R-ECD Fc demonstrated no impact on cell proliferation in any cell line (representative data shown for the MFE-280 model, FIG. 6)

Example 2

An FGFR1 ECD Fc Fusion Molecule Inhibits Endometrial Tumor Growth in an FGFR2S252W Murine Xenograft Model The anti-cancer activities of R1Mut4 were tested in a xenograft endometrial cancer model using human endometrial carcinoma MFE-280 cells with a S252W mutated FGFR2 genomic locus. MFE-280 cells were maintained in 40% RPMI 1640, 40% Minimum Essential Medium (with Earle's salts) supplemented with 2 mM L-glutamine, 20% FBS (all from Cellgro) and 1×ITS (Insulin, Transferrin and Sodium Selenite, from Sigma) at 37° C. in a humidified atmosphere with 5% $CO_2$. Semi-confluent cells (~80%) were re-suspended in PBS without calcium and magnesium (Cellgro) at a concentration of $1 \times 10^8$ cells per ml. Matrigel basement membrane matrix (BD Biosciences) was added to 50% (vol/vol) to give a final concentration of $5 \times 10^7$ cells per ml and the mixture stored on ice until implantation into mice.

For the xenograft experiments, twenty CB17 SCID mice (Charles River Laboratories) were used. On day 1, the body weight of each mouse was measured. The mice were randomly distributed into 2 groups of 10 mice based on their body weight. Once assigned to a treatment group, the mice were shaved on the right hind flank and then inoculated subcutaneously with $5 \times 10^6$ (100 nl) of the MFE-280 cells prepared as described above.

On the next day, animals were dosed with the test articles according to the dosing scheme shown in Table 2 below.

TABLE 2

| MFE-280 Xenograft Dosing Groups | | | |
|---|---|---|---|
| Group | Number of Animals | Test Article and Dose (mg test article per weight mouse) | Dosing Route and Schedule |
| 1 | 10 | Albumin | Intraperitoneal, 2X/week |
| 2 | 10 | R1Mut4, 15 mg/kg | Intraperitoneal, 2X/week |

Tumor sizes were measured in each mouse on days 7, 14, and 21, 28, 35, 39, 42, 49, and 57 following the day of tumor cell inoculation. The length and width of each tumor was measured using calipers and the tumor size calculated according to the formula:

Tumor size ($mm^3$)=(width (mm)×length $(mm))^2/2$

Figure 7:
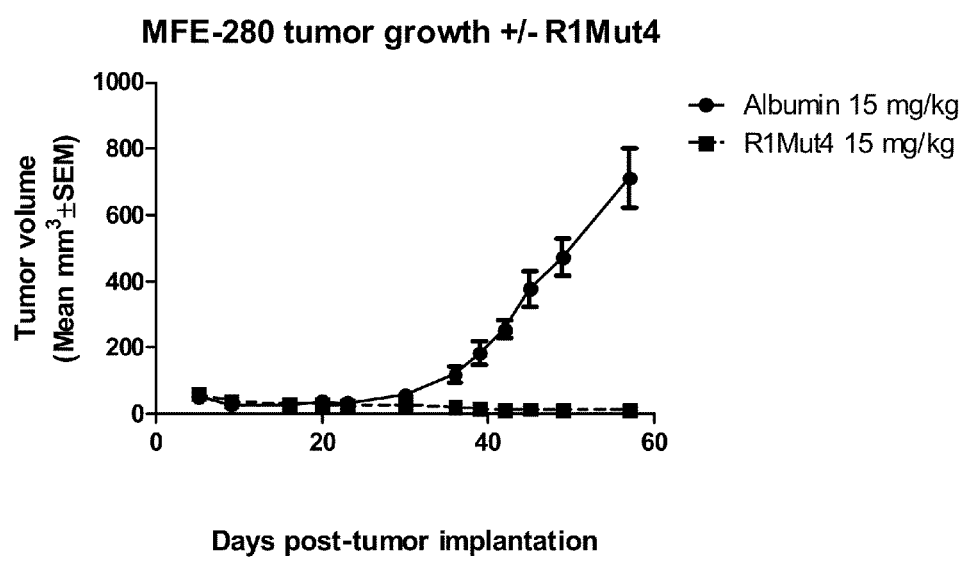
FIG. 7 shows the effect of R1Mut4 in an FGFR2S252W mouse xenograft assay in comparison to an albumin control.

FIG. 7 shows the results of this experiment. Mice that received R1Mut4 showed a dramatic inhibition of tumor growth compared to albumin-treated animals. Table 3 shows the average percent inhibition of tumor growth for each treatment group at days 39 and 57 compared to the vehicle treated group, and the corresponding P-values. P-values were calculated using an ANOVA analysis. (See, e.g., *Mathematical Statistics and Data Analysis*, 1988, Wadsworth & Brooks, Pacific Grove, Calif.) This analysis demonstrated that R1Mut4 significantly reduced tumor growth in an endometrial carcinoma cell line, MFE-280, expressing a mutated (S252W) FGFR2 receptor.

TABLE 3

| MFE-280 Xenograft Results | | |
|---|---|---|
| Group | Day 39: Percent inhibition; p-value | Day 57: Percent inhibition; p-value |
| R1Mut4, 15 mg/kg, IP | 90.4%, P-value = <0.0001 | 98.0%, P-value = <0.0001 |

Example 3

An FGFR1 ECD Fc Fusion Molecule Inhibits Endometrial Tumor Growth in a Therapeutic FGFR2S252W Murine Xenograft Model in a Dose-Dependent Manner The dose-dependent anti-cancer activities of R1Mut4 were tested in a therapeutic (or established) xenograft endometrial cancer model using human endometrial carcinoma MFE-280 cells with a S252W mutated FGFR2 genomic locus. MFE-280 cells were maintained as outlined in Example 2. For the xenograft experiments, forty CB17 SCID mice (Charles River Laboratories) were used. On day 1 mice were shaved on the right hind flank and then inoculated subcutaneously with $5 \times 10^6$ (100 µl) of the MFE-280 cells prepared as described in example 1. Following implantation tumor sizes were measured every 3 days until tumors reached the size of 150-200 mm$^3$ (average day 28 post-tumor implantation). The mice were then randomly distributed into 4 groups of 10 mice based on their body weight and tumor size. Animals were dosed with the test articles according to the dosing scheme shown in Table 4 below, starting on the day in which measurements showed that the tumor reached the size of 150-200 mm$^3$.

TABLE 4

MFE-280 Xenograft Dosing Groups

| Group | Number of Animals | Test Article and Dose (mg test article per weight mouse) | Dosing Route and Schedule |
|---|---|---|---|
| 1 | 10 | Albumin | Intraperitoneal, 2X/week |
| 2 | 10 | R1Mut4, 0.15 mg/kg | Intraperitoneal, 2X/week |
| 3 | 10 | R1Mut4, 1.5 mg/kg | Intraperitoneal, 2X/week |
| 4 | 10 | R1Mut4, 15 mg/kg | Intraperitoneal, 2X/week |

Figure 8:
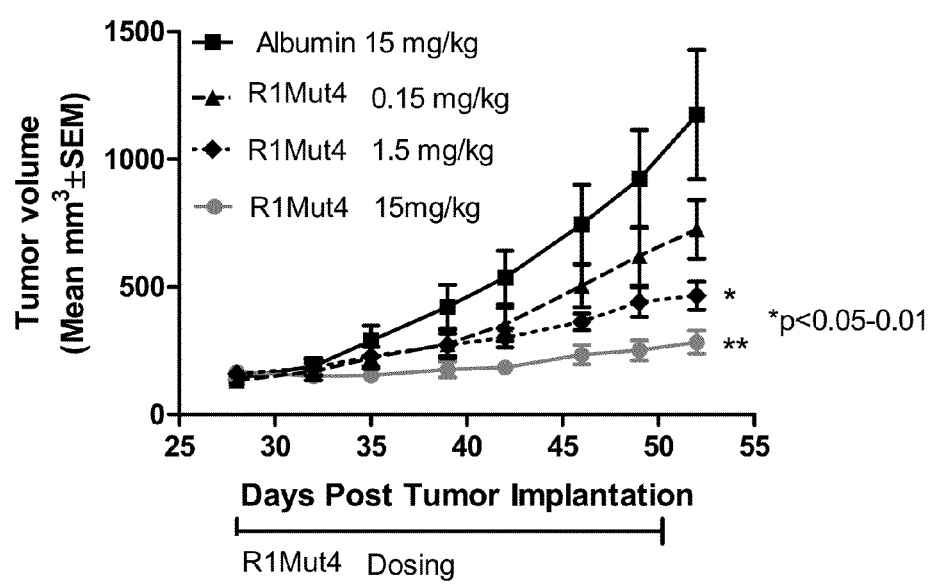
FIG. 8 shows the dose-dependent anti-cancer activities of R1Mut4 in a therapeutic (or established) xenograft endometrial cancer model using human endometrial carcinoma MFE-280 cells with a S252W mutated FGFR2 genomic locus.

Tumor sizes were measured in each mouse on days 32, 35, 39, 42, 46, 49 and 52 following the day of tumor cell inoculation. The length and width of each tumor was measured using calipers and the tumor size calculated according to the formula: Tumor size (mm$^3$)=(width (mm)×length (mm))$^2$/2. FIG. 8 shows the results of this experiment. Mice that received R1Mut4 showed a dose-dependent inhibition of tumor growth compared to albumin-treated animals.

Table 5 shows the average percent inhibition of tumor growth for each treatment group at day 52 compared to the vehicle treated group, and the corresponding P-values. This analysis demonstrated that R1Mut4 significantly reduced tumor growth in an FGFR2 mutant endometrial carcinoma model in a therapeutic (or established) mode and that tumor inhibition was dose-responsive.

TABLE 5

MFE-280 Xenograft Results in a therapeutic model

| Group | Tumor volume (Mean ± SD) | % TGI | P value |
|---|---|---|---|
| Albumin 15 mg/kg | 1175.0 ± 801 | — | — |
| R1Mut4 0.15 mg/kg | 725.4 ± 363.5 | 38.2 | >0.05 |
| R1Mut4 1.5 mg/kg | 465.7 ± 174.6 | 60.4 | <0.01 |
| R1Mut4 15 mg/kg | 283.7 ± 143.5 | 75.9 | <0.001 |

Example 4

Figure 9:
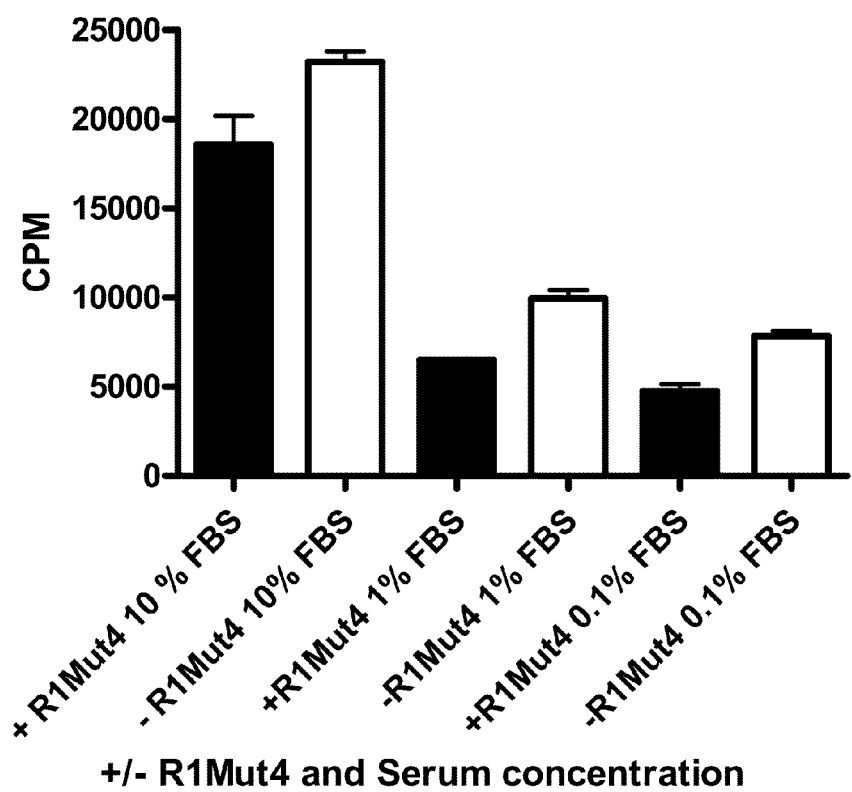
FIG. 9 shows the effect of R1Mut4 on HCC1143 cell proliferation using a tritiated thymidine incorporation assay. R1Mut4 reduced cell proliferation (P=<0.05 all conditions) in the HCC1143 cell line by 25 percent. The control protein CSF1R-ECD Fc demonstrated no impact on cell HCC1143 proliferation.
Figure 10:
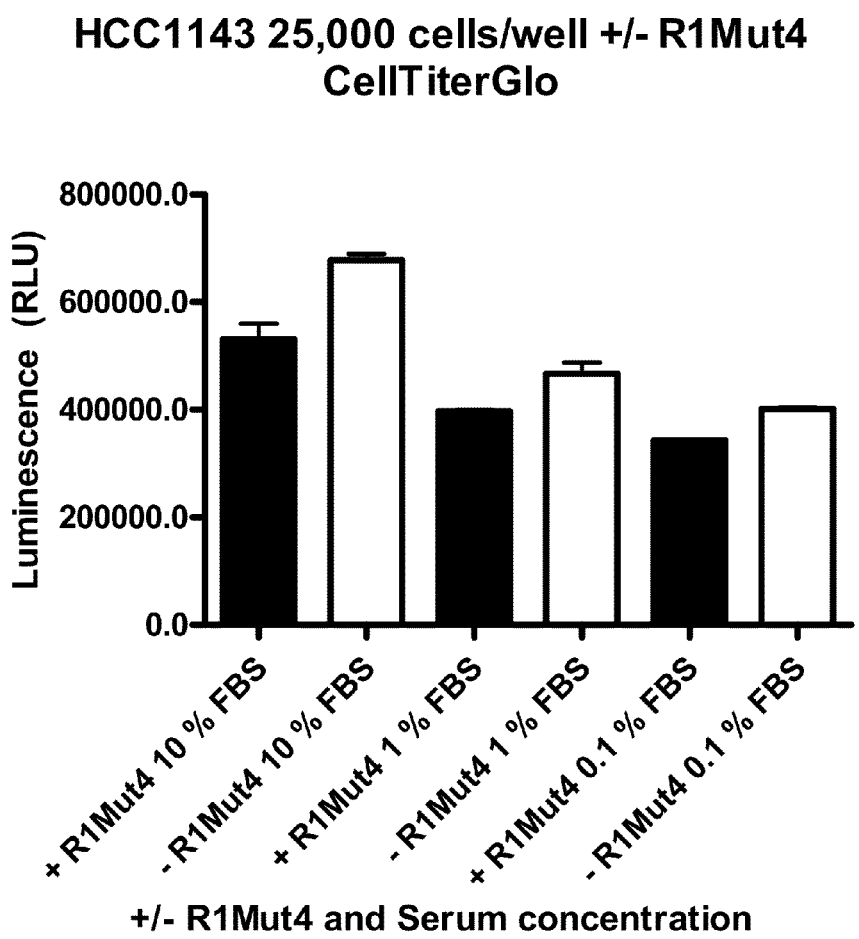
FIG. 10 shows the effect of R1Mut4 on HCC1143 cell proliferation using the CellTiter-Glo® assay. Incubation with R1Mut4 significantly reduced (P=<0.05 all conditions) cell number in the HCC1143 cell line expressing the R203C mutant FGFR2.

An FGFR1 ECD Fc Fusion Molecule Inhibits HCC1143 (FGFR2R203C) Breast Carcinoma Cell Lines in Tissue Culture The breast carcinoma cell line, HCC1143 (Cat #CRL-2321), which contains a R203C mutation in the FGFR2 locus (COSMIC database, Sanger Inst.,) was obtained from American Type Culture Collection (ATCC; Manassas, Va.) and maintained in 90% RPMI 1640 with 2 mM L-glutamine and 10% FBS (all from Mediatech, Inc). Cells were incubated at 37° C. at 5% CO$_2$. Mutation status of the FGFR2 receptor in the cell lines was confirmed by PCR amplification and sequencing of the genomic FGFR2 gene. To determine the impact of an FGFR1 ECD Fc fusion molecule on the HCC1143 cell line in tissue culture, the procedure described in Example 1 was used. In the tritiated thymidine incorporation assay, R1Mut4 reduced cell proliferation (FIG. 9; P=<0.05 all conditions) in the HCC1143 cell line by 25 percent. The control protein CSF1R-ECD Fc demonstrated no impact on cell HCC1143 proliferation. Results from the CellTiter-Glo® assay are shown in FIG. 10. These results demonstrated that cell number in the HCC1143 cell line expressing the R203C mutant FGFR2 gene was significantly (P=<0.05 all conditions) reduced by R1Mut4 incubation.

TABLE 6

Sequences and Descriptions

| SEQ. ID. NO. | Description | Sequence |
|---|---|---|
| 1 | FGFR1 IIIc ECD | RPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNPVA PYWTSPEKME KKLHAVPAAK TVKFKCPSSG TPNPTLRWLK NGKEFKPDHR IGGYKVRYAT WSIIMDSVVP SDKGNYTCIV ENEYGSINHT YQLDVVERSP HRPILQAGLP ANKTVALGSN VEFMCKVYSD PQPHIQWLKH IEVNGSKIGP DNLPYVQILK TAGVNTTDKE MEVLHLRNVS FEDAGEYTCL AGNSIGLSHH SAWLTVLEAL EERPAVMTSP LYLE |
| 2 | FGFR1 IIIc ECD w/ signal peptide | MWSWKCLLFW AVLVTATLCT A RPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNPVA PYWTSPEKME KKLHAVPAAK TVKFKCPSSG TPNPTLRWLK NGKEFKPDHR IGGYKVRYAT WSIIMDSVVP SDKGNYTCIV ENEYGSINHT YQLDVVERSP HRPILQAGLP ANKTVALGSN VEFMCKVYSD PQPHIQWLKH IEVNGSKIGP DNLPYVQILK TAGVNTTDKE MEVLHLRNVS FEDAGEYTCL AGNSIGLSHH SAWLTVLEAL EERPAVMTSP LYLE |

TABLE 6-continued

Sequences and Descriptions

| SEQ. ID. NO. | Description | Sequence |
|---|---|---|
| 3 | FGFR1 IIIc ECD Δ4 (R1Mut1 ECD) | RPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNPVA PYWTSPEKME KKLHAVPAAK TVKFKCPSSG TPNPTLRWLK NGKEFKPDHR IGGYKVRYAT WSIIMDSVVP SDKGNYTCIV ENEYGSINHT YQLDVVERSP HRPILQAGLP ANKTVALGSN VEFMCKVYSD PQPHIQWLKH IEVNGSKIGP DNLPYVQILK TAGVNTTDKE MEVLHLRNVS FEDAGEYTCL AGNSIGLSHH SAWLTVLEAL EERPAVMTSP |
| 4 | FGFR1 IIIc ECD Δ8 (R1Mut2 ECD) | RPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNPVA PYWTSPEKME KKLHAVPAAK TVKFKCPSSG TPNPTLRWLK NGKEFKPDHR IGGYKVRYAT WSIIMDSVVP SDKGNYTCIV ENEYGSINHT YQLDVVERSP HRPILQAGLP ANKTVALGSN VEFMCKVYSD PQPHIQWLKH IEVNGSKIGP DNLPYVQILK TAGVNTTDKE MEVLHLRNVS FEDAGEYTCL AGNSIGLSHH SAWLTVLEAL EERPAV |
| 5 | FGFR1 IIIc ECD Δ9 (R1Mut3 ECD) | RPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNPVA PYWTSPEKME KKLHAVPAAK TVKFKCPSSG TPNPTLRWLK NGKEFKPDHR IGGYKVRYAT WSIIMDSVVP SDKGNYTCIV ENEYGSINHT YQLDVVERSP HRPILQAGLP ANKTVALGSN VEFMCKVYSD PQPHIQWLKH IEVNGSKIGP DNLPYVQILK TAGVNTTDKE MEVLHLRNVS FEDAGEYTCL AGNSIGLSHH SAWLTVLEAL EERPA |
| 6 | FGFR1 IIIc ECD Δ14 (R1Mut4 ECD) | RPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNPVA PYWTSPEKME KKLHAVPAAK TVKFKCPSSG TPNPTLRWLK NGKEFKPDHR IGGYKVRYAT WSIIMDSVVP SDKGNYTCIV ENEYGSINHT YQLDVVERSP HRPILQAGLP ANKTVALGSN VEFMCKVYSD PQPHIQWLKH IEVNGSKIGP DNLPYVQILK TAGVNTTDKE MEVLHLRNVS FEDAGEYTCL AGNSIGLSHH SAWLTVLEAL |
| 7 | FGFR1 IIIc ECD Δ19 (R1Mut5 ECD) | RPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNPVA PYWTSPEKME KKLHAVPAAK TVKFKCPSSG TPNPTLRWLK NGKEFKPDHR IGGYKVRYAT WSIIMDSVVP SDKGNYTCIV ENEYGSINHT YQLDVVERSP HRPILQAGLP ANKTVALGSN VEFMCKVYSD PQPHIQWLKH IEVNGSKIGP DNLPYVQILK TAGVNTTDKE MEVLHLRNVS FEDAGEYTCL AGNSIGLSHH SAWLT |
| 8 | FGFR1 IIIc ECD ΔP364 and A365 (R1Mut7 ECD) | RPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNPVA PYWTSPEKME KKLHAVPAAK TVKFKCPSSG TPNPTLRWLK NGKEFKPDHR IGGYKVRYAT WSIIMDSVVP SDKGNYTCIV ENEYGSINHT YQLDVVERSP HRPILQAGLP ANKTVALGSN VEFMCKVYSD PQPHIQWLKH IEVNGSKIGP DNLPYVQILK TAGVNTTDKE MEVLHLRNVS FEDAGEYTCL AGNSIGLSHH SAWLTVLEAL EERVMTSPLY LE |
| 9 | FGFR1 IIIc ECD P364G (R1Mut8 ECD) | RPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNPVA PYWTSPEKME KKLHAVPAAK TVKFKCPSSG TPNPTLRWLK NGKEFKPDHR IGGYKVRYAT WSIIMDSVVP SDKGNYTCIV ENEYGSINHT YQLDVVERSP HRPILQAGLP ANKTVALGSN VEFMCKVYSD PQPHIQWLKH IEVNGSKIGP DNLPYVQILK TAGVNTTDKE MEVLHLRNVS FEDAGEYTCL AGNSIGLSHH SAWLTVLEAL EERGAVMTSP LYLE |
| 10 | FGFR1 IIIc ECD P364M (R1Mut9 ECD) | RPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNPVA PYWTSPEKME KKLHAVPAAK TVKFKCPSSG TPNPTLRWLK NGKEFKPDHR IGGYKVRYAT WSIIMDSVVP |

TABLE 6-continued

Sequences and Descriptions

| SEQ. ID. NO. | Description | Sequence |
|---|---|---|
| | | SDKGNYTCIV ENEYGSINHT YQLDVVERSP HRPILQAGLP ANKTVALGSN VEFMCKVYSD PQPHIQWLKH IEVNGSKIGP DNLPYVQILK TAGVNTTDKE MEVLHLRNVS FEDAGEYTCL AGNSIGLSHH SAWLTVLEAL EERMAVMTSP LYLE |
| 11 | FGFR1 IIIc ECD M367N (R1Mut10 ECD) | RPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNPVA PYWTSPEKME KKLHAVPAAK TVKFKCPSSG TPNPTLRWLK NGKEFKPDHR IGGYKVRYAT WSIIMDSVVP SDKGNYTCIV ENEYGSINHT YQLDVVERSP HRPILQAGLP ANKTVALGSN VEFMCKVYSD PQPHIQWLKH IEVNGSKIGP DNLPYVQILK TAGVNTTDKE MEVLHLRNVS FEDAGEYTCL AGNSIGLSHH SAWLTVLEAL EERPAVNTSP LYLE |
| 12 | FGFR1 RM ECD | RPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNRMP VAPYWTSPEK MEKKLHAVPA AKTVKFKCPS SGTPNPTLRW LKNGKEFKPD HRIGGYKVRY ATWSIIMDSV VPSDKGNYTC IVENEYGSIN HTYQLDVVER SPHRPILQAG LPANKTVALG SNVEFMCKVY SDPQPHIQWL KHIEVNGSKI GPDNLPYVQI LKTAGVNTTD KEMEVLHLRN VSFEDAGEYT CLAGNSIGLS HHSAWLTVLE ALEERPAVMT SPLYLE |
| 13 | FGFR1 signal peptide | MWSWKCLLFWAVLVTATLCTA |
| 14 | FGFR2 signal peptide | MVSWGRFICLVVVTMATLSLA |
| 15 | FGFR3 signal peptide | MGAPACALALCVAVAIVAGASS |
| 16 | FGFR4 signal peptide | MRLLLALLGI LLSVPGPPVL S |
| 17 | Fc C237S | EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 18 | Fc | ERKCCVECPP CPAPPVAGPS VFLFPPKPKD TLMISRTPEV TCVVVDVSHE DPEVQFNWYV DGVEVHNAKT KPREEQFNST FRVVSVLTVV HQDWLNGKEY KCKVSNKGLP APIEKTISKT KGQPREPQVY TLPPSREEMT KNQVSLTCLV KGFYPSDIAV EWESNGQPEN NYKTTPPMLD SDGSFFLYSK LTVDKSRWQQ GNVFSCSVMH EALHNHYTQK SLSLSPGK |
| 19 | Fc | ESKYGPPCPS CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |
| 20 | Fc | ESKYGPPCPP CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |
| 21 | Fc | ERKSSVECPP CPAPPVAGPS VFLFPPKPKD TLMISRTPEV TCVVVDVSHE DPEVQFNWYV DGVEVHNAKT KPREEQFNST FRVVSVLTVV HQDWLNGKEY KCKVSNKGLP APIEKTISKT KGQPREPQVY TLPPSREEMT KNQVSLTCLV KGFYPSDIAV EWESNGQPEN NYKTTPPMLD SDGSFFLYSK LTVDKSRWQQ GNVFSCSVMH EALHNHYTQK SLSLSPGK |
| 22 | FGFR1 Mc ECD Δ14 + Fc (R1Mut14) | RPSPTLPEQA QPWGAPVEVE SFLVHPGDLL QLRCRLRDD VQSINWLRDG VQLAES RTR ITGEEVEVQD SVPADSGLYA CVTSSPSGSD TTYFSV VSD ALPSSEDDDD DDDSSSEEKE |

TABLE 6-continued

Sequences and Descriptions

| SEQ. ID. NO. | Description | Sequence |
|---|---|---|
| | | TDNTKPNPVA PYWTSPEKME KKLHAVPAAK TVKFKCPSSG TPNPTLRWLK NGKEFKPDHR IGGYKVRYAT WSIIMDSVVP SDKG YTCIV ENEYGSI HT YQLDVVERSP HRPILQAGLP A KTVALGSN VEFMCKVYSD PQPHIQWLKH IEV GSKIGP DNLPYVQILK TAGV TTDKE MEVLHLR VS FEDAGEYTCL AGNSIGLSHH SAWLTVLEAL EPKSSDKTHT CPPCPAPELL GGPSVFLFPP KPKDTLMISR TPEVTCVVVD VSHEDPEVKF NWYVDGVEVH NAKTKPREEQ Y STYRVVSV LTVLHQDWLN GKEYKCKVSN KALPAPIEKT ISKAKGQPRE PQVYTLPPSR DELTKNQVSL TCLVKGFYPS DIAVEWESNGQPENNYKTTP PVLDSDGSFF LYSKLTVDKS RWQQGNVFSC SVMHEALHNH YTQKSLSLSP GK |
| 23 | FGFR2 IIIb precursor (i.e. with signal peptide) GenBank Acc. No. NP_075259.2 | MVSWGRFICL VVVTMATLSL ARPSFSLVED TTLEPEEPPT KYQISQPEVY VAAPGESLEV RCLLKDAAVI SWTKDGVHLG PNNRTVLIGE YLQIKGATPR DSGLYACTAS RTVDSETWYF MVNVTDAISS GDDEDDTGA EDFVSENSNN KRAPYWTNTE KMEKRLHAVP AANTVKFRCP AGGNPMPTMR WLKNGKEFKQ EHRIGGYKVR NQHWSLIMES VVPSDKGNYT CVVENEYGSI NHTYHLDVVE RSPHRPILQA GLPANASTVV GGDVEFVCKV YSDAQPHIQW IKHVEKNGSK YGPDGLPYLK VLKHSGINSS NAEVLALFNV TEADAGEYIC KVSNYIGQAN QSAWLTVLPK QQAPGREKEI TASPDYLEIA IYCIGVFLIA CMVVTVILCR MKNTTKKPDF SSQPAVHKLT KRIPLRRQVT VSAESSSSMN SNTPLVRITT RLSSTADTPM LAGVSEYELP EDPKWEFPRD KLTLGKPLGE GCFGQVVMAE AVGIDKDKPK EAVTVAVKML KDDATEKDLS DLVSEMEMMK MIGKHKNIIN LLGACTQDGP LYVIVEYASK GNLREYLRAR RPPGMEYSYD INRVPEEQMT FKDLVSCTYQ LARGMEYLAS QKCIHRDLAA RNVLVTENNV MKIADFGLAR DINNIDYYKK TTNGRLPVKW MAPEALFDRV YTHQSDVWSF GVLMWEIFTL GGSPYPGIPV EELFKLLKEG HRMDKPANCT NELYMMMRDC WHAVPSQRPT FKQLVEDLDR ILTLTTNEEY LDLSQPLEQY SPSYPDTRSS CSSGDDSVFS PDPMPYEPCL PQYPHINGSV KT |
| 24 | FGFR2 IIIb precursor S252W | MVSWGRFICL VVVTMATLSL ARPSFSLVED TTLEPEEPPT KYQISQPEVY VAAPGESLEV RCLLKDAAVI SWTKDGVHLG PNNRTVLIGE YLQIKGATPR DSGLYACTAS RTVDSETWYF MVNVTDAISS GDDEDDTGA EDFVSENSNN KRAPYWTNTE KMEKRLHAVP AANTVKFRCP AGGNPMPTMR WLKNGKEFKQ EHRIGGYKVR NQHWSLIMES VVPSDKGNYT CVVENEYGSI NHTYHLDVVE RWPHRPILQA GLPANASTVV GGDVEFVCKV YSDAQPHIQW IKHVEKNGSK YGPDGLPYLK VLKHSGINSS NAEVLALFNV TEADAGEYIC KVSNYIGQAN QSAWLTVLPK QQAPGREKEI TASPDYLEIA IYCIGVFLIA CMVVTVILCR MKNTTKKPDF SSQPAVHKLT KRIPLRRQVT VSAESSSSMN SNTPLVRITT RLSSTADTPM LAGVSEYELP EDPKWEFPRD KLTLGKPLGE GCFGQVVMAE AVGIDKDKPK EAVTVAVKML KDDATEKDLS DLVSEMEMMK MIGKHKNIIN LLGACTQDGP LYVIVEYASK GNLREYLRAR RPPGMEYSYD INRVPEEQMT FKDLVSCTYQ LARGMEYLAS QKCIHRDLAA RNVLVTENNV MKIADFGLAR DINNIDYYKK TTNGRLPVKW MAPEALFDRV YTHQSDVWSF GVLMWEIFTL GGSPYPGIPV EELFKLLKEG HRMDKPANCT NELYMMMRDC WHAVPSQRPT FKQLVEDLDR ILTLTTNEEY LDLSQPLEQY SPSYPDTRSS CSSGDDSVFS PDPMPYEPCL PQYPHINGSV KT |
| 25 | FGFR2 IIIb precursor P253R | MVSWGRFICL VVVTMATLSL ARPSFSLVED TTLEPEEPPT KYQISQPEVY VAAPGESLEV RCLLKDAAVI SWTKDGVHLG PNNRTVLIGE YLQIKGATPR DSGLYACTAS RTVDSETWYF MVNVTDAISS GDDEDDTGA EDFVSENSNN KRAPYWTNTE KMEKRLHAVP AANTVKFRCP AGGNPMPTMR WLKNGKEFKQ EHRIGGYKVR NQHWSLIMES VVPSDKGNYT CVVENEYGSI NHTYHLDVVE RSRHRPILQA GLPANASTVV GGDVEFVCKV YSDAQPHIQW IKHVEKNGSK YGPDGLPYLK VLKHSGINSS NAEVLALFNV TEADAGEYIC KVSNYIGQAN QSAWLTVLPK QQAPGREKEI TASPDYLEIA IYCIGVFLIA CMVVTVILCR MKNTTKKPDF SSQPAVHKLT KRIPLRRQVT VSAESSSSMN SNTPLVRITT RLSSTADTPM LAGVSEYELP EDPKWEFPRD KLTLGKPLGE GCFGQVVMAE AVGIDKDKPK EAVTVAVKML KDDATEKDLS DLVSEMEMMK MIGKHKNIIN LLGACTQDGP LYVIVEYASK GNLREYLRAR RPPGMEYSYD INRVPEEQMT FKDLVSCTYQ LARGMEYLAS QKCIHRDLAA RNVLVTENNV MKIADFGLAR DINNIDYYKK TTNGRLPVKW MAPEALFDRV YTHQSDVWSF GVLMWEIFTL GGSPYPGIPV EELFKLLKEG |

TABLE 6-continued

Sequences and Descriptions

| SEQ. ID. NO. | Description | Sequence |
|---|---|---|
| | | HRMDKPANCT NELYMMMRDC WHAVPSQRPT FKQLVEDLDR ILTLTTNEEY LDLSQPLEQY SPSYPDTRSS CSSGDDSVFS PDPMPYEPCL PQYPHINGSV KT |

It is to be understood that both the foregoing general and detailed descriptions are exemplary and explanatory only and are not restrictive of the invention as claimed. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of treating a cancer characterized by a ligand dependent activating mutation in FGFR2 in a subject, comprising administering a therapeutically effective amount of an FGFR1 ECD to the subject.

2. The method of claim 1, wherein the cancer is endometrial, gastric, lung, or ovarian cancer.

3. The method of claim 2, wherein the cancer is endometrial cancer.

4. The method of claim 1, wherein the ligand dependent activating mutation comprises at least one substitution, insertion, or deletion in the IgIII domain of the FGFR2 protein.

5. The method of claim 1, wherein the ligand dependent activating mutation comprises at least one substitution, insertion, or deletion in the IgII-IgIII hinge region of the FGFR2 protein.

6. The method of claim 5, wherein the mutation is a point mutation of the serine residue at amino acid position 252 of the FGFR2 protein.

7. The method of claim 5, wherein the mutation is a point mutation of the proline residue at amino acid position 253 of the FGFR2 protein.

8. The method of claim 1, wherein the FGFR1 ECD is an FGFR1 ECD fusion molecule.

9. The method of claim 8, wherein the FGFR1 ECD fusion molecule comprises an Fc polypeptide.

10. The method of claim 1, wherein the FGFR1 ECD comprises the amino acid sequence of any one of SEQ ID NOs: 1 or 3-12.

11. The method of claim 1, wherein the FGFR1 ECD is administered before, after, or substantially contemporaneously with chemotherapy, radiation therapy, biologic therapy, or surgery.

12. A method of administering an FGFR1 ECD to a subject in need thereof, comprising:

(a) determining if tumor cells from the subject express a ligand dependent activating mutation in FGFR2; and
(b) if the tumor cells do express the ligand dependent activating mutation in FGFR2, then administering a therapeutically effective amount of an FGFR1 ECD to the subject.

13. The method of claim 12, wherein the cancer is endometrial, gastric, lung, or ovarian cancer.

14. The method of claim 13, wherein the cancer is endometrial cancer.

15. The method of claim 12, wherein the ligand dependent activating mutation comprises at least one substitution, insertion, or deletion in the IgIII domain of the FGFR2 protein.

16. The method of claim 12, wherein the ligand dependent activating mutation comprises at least one substitution, insertion, or deletion in the IgII-IgIII hinge region of the FGFR2 protein.

17. The method of claim 16, wherein the mutation is a point mutation of the serine residue at amino acid position 252 of the FGFR2 protein.

18. The method of claim 16, wherein the mutation is a point mutation of the proline residue at amino acid position 253 of the FGFR2 protein.

19. The method of claim 12, wherein the FGFR1 ECD is an FGFR1 ECD fusion molecule.

20. The method of claim 19, wherein the FGFR1 ECD fusion molecule comprises an Fc polypeptide.

21. The method of claim 12, wherein the FGFR1 ECD comprises the amino acid sequence of any one of SEQ ID NOs: 1 or 3-12.

22. The method of claim 12, wherein the FGFR1 ECD is administered before, after, or substantially contemporaneously with chemotherapy, radiation therapy, biologic therapy, or surgery.

* * * * *